US012594094B2

(12) United States Patent
Mark et al.

(10) Patent No.: US 12,594,094 B2
(45) Date of Patent: Apr. 7, 2026

(54) SELECTIVELY LOCKABLE HOLDING ARRANGEMENT FOR A SURGICAL ACCESS SYSTEM

(71) Applicant: Stryker Corporation, Portage, MI (US)

(72) Inventors: Joseph L. Mark, Indianapolis, IN (US); Brian C. Dougherty, Terre Haute, IN (US); Chad Lamar, Indianapolis, IN (US)

(73) Assignee: Stryker Corporation, Portage, MI (US)

( * ) Notice: Subject to any disclaimer, the term of this patent is extended or adjusted under 35 U.S.C. 154(b) by 712 days.

(21) Appl. No.: 17/887,204

(22) Filed: Aug. 12, 2022

(65) Prior Publication Data

US 2023/0015301 A1 Jan. 19, 2023

Related U.S. Application Data

(63) Continuation of application No. 16/443,142, filed on Jun. 17, 2019, now Pat. No. 11,413,066, which is a
(Continued)

(51) Int. Cl.
*A61B 17/34* (2006.01)
*A61B 5/055* (2006.01)
(Continued)

(52) U.S. Cl.
CPC .......... *A61B 17/3423* (2013.01); *A61B 5/055* (2013.01); *A61B 17/0218* (2013.01);
(Continued)

(58) Field of Classification Search
CPC . A61B 17/0218; A61B 17/3423; A61B 5/055; A61B 90/50; A61B 34/20; A61B 2090/508; A61B 2017/347
See application file for complete search history.

(56) References Cited

U.S. PATENT DOCUMENTS

| 1,695,009 A | 12/1928 | Cochran |
| 3,690,323 A | 9/1972 | Wortman et al. |

(Continued)

FOREIGN PATENT DOCUMENTS

| RU | 2009124446 A | 1/2011 |
| WO | 2006017507 A1 | 2/2006 |

(Continued)

OTHER PUBLICATIONS

O'Rourke, M.D., et al., "Vycor Medical, Inc.—Business Summary," www.vycormedical.com, 2014, 2 pages.
(Continued)

*Primary Examiner* — Nicholas J Plionis
(74) *Attorney, Agent, or Firm* — Howard & Howard Attorneys PLLC

(57) ABSTRACT

Selectively lockable holding arrangements for a surgical access assembly are disclosed. One holding arrangement includes a body portion, an engagement barrel and a retaining member configured as a hook at a distal end of the body portion. The engagement barrel is position on a proximal end of the body portion and is configured to be selectively rotated about the body portion when operatively connected to a surgical holding arrangement. A rotation brake is mounted on the body section. The rotation brake is selectively operable to lock the engagement barrel against rotation.

16 Claims, 44 Drawing Sheets

Related U.S. Application Data continuation-in-part of application No. 15/070,739, filed on Mar. 15, 2016, now Pat. No. 10,765,450.

(51) Int. Cl.

| | | |
|---|---|---|
| *A61B 17/02* | (2006.01) | |
| *A61B 34/20* | (2016.01) | |
| *A61B 90/00* | (2016.01) | |
| *A61B 90/50* | (2016.01) | |

(52) U.S. Cl.
CPC .............. *A61B 34/20* (2016.02); *A61B 90/50* (2016.02); *A61B 2017/347* (2013.01); *A61B 2090/0811* (2016.02); *A61B 2090/508* (2016.02)

(56) References Cited

U.S. PATENT DOCUMENTS

| | | | |
|---|---|---|---|
| 4,386,602 A | | 6/1983 | Sheldon et al. |
| 4,638,798 A | | 1/1987 | Shelden et al. |
| 5,025,780 A | | 6/1991 | Farley |
| 5,183,464 A | | 2/1993 | Dubrui et al. |
| 5,217,441 A | | 6/1993 | Shichman |
| 5,320,611 A | | 6/1994 | Bonutti et al. |
| 5,431,676 A | | 7/1995 | Dubrul et al. |
| 5,728,046 A | * | 3/1998 | Mayer ............... A61B 17/0293 |
| | | | 600/210 |
| 5,860,996 A | | 1/1999 | Urban et al. |
| 6,047,218 A | | 4/2000 | Whayne et al. |
| 6,129,685 A | | 10/2000 | Howard, III |
| 6,179,826 B1 | | 1/2001 | Aebischer et al. |
| 6,226,548 B1 | | 5/2001 | Foley et al. |
| 6,245,052 B1 | | 6/2001 | Orth et al. |
| 6,280,399 B1 | | 8/2001 | Rossin et al. |
| 6,293,952 B1 | | 9/2001 | Brosens et al. |
| 6,331,180 B1 | | 12/2001 | Cosman et al. |
| 6,374,135 B1 | | 4/2002 | Bucholz |
| 6,416,520 B1 | | 7/2002 | Kynast et al. |
| 6,669,685 B1 | | 12/2003 | Rizoiu et al. |
| 6,942,634 B2 | | 9/2005 | Odland |
| 7,857,271 B2 | | 12/2010 | Lees |
| 9,579,121 B2 | | 2/2017 | Mark et al. |
| 9,655,639 B2 | | 5/2017 | Mark |
| 10,543,057 B2 | | 1/2020 | Mark et al. |
| 10,588,679 B2 | | 3/2020 | Kukla et al. |
| 10,765,450 B2 | * | 9/2020 | Mark .................... A61B 90/50 |
| 2003/0073934 A1 | | 4/2003 | Putz |
| 2003/0191371 A1 | | 10/2003 | Smith et al. |
| 2003/0225416 A1 | * | 12/2003 | Bonvallet ............ A61B 17/025 |
| | | | 606/205 |
| 2004/0024291 A1 | | 2/2004 | Zinkel |
| 2004/0059375 A1 | | 3/2004 | Ginn et al. |
| 2004/0068172 A1 | | 4/2004 | Nowinski et al. |
| 2004/0102804 A1 | | 5/2004 | Chin |
| 2004/0186346 A1 | | 9/2004 | Smith et al. |
| 2004/0215143 A1 | | 10/2004 | Brady et al. |
| 2007/0100211 A1 | | 5/2007 | Selover et al. |
| 2007/0270898 A1 | | 11/2007 | Lillehei |
| 2007/0299459 A1 | | 12/2007 | Way et al. |
| 2008/0306442 A1 | * | 12/2008 | Bardsley ............ A61B 17/3439 |
| | | | 604/164.04 |
| 2009/0043310 A1 | | 2/2009 | Rasmussen |
| 2009/0048622 A1 | | 2/2009 | Wilson |
| 2009/0312611 A1 | | 12/2009 | Mangiardi |
| 2010/0010315 A1 | | 1/2010 | Mangiardi |
| 2011/0034775 A1 | | 2/2011 | Lozman et al. |
| 2012/0029566 A1 | | 2/2012 | Rezach |
| 2012/0253353 A1 | | 10/2012 | Mcbride |
| 2012/0253375 A1 | * | 10/2012 | Mark ................. A61B 17/3421 |
| | | | 606/185 |
| 2015/0374416 A1 | | 12/2015 | Warren et al. |
| 2016/0015374 A1 | | 1/2016 | Gifford et al. |
| 2020/0038058 A1 | | 2/2020 | Mark et al. |
| 2021/0259728 A1 | | 8/2021 | Thomas et al. |

FOREIGN PATENT DOCUMENTS

| | | |
|---|---|---|
| WO | 2006050047 A1 | 5/2006 |
| WO | 2007002251 A1 | 1/2007 |
| WO | 2008066543 A1 | 6/2008 |
| WO | 2008121294 A1 | 10/2008 |

OTHER PUBLICATIONS

PCT International Search Report and Opinion dated Apr. 9, 2013 for PCT/US2012/061568.

PCT International Search Report dated Jun. 20, 2006 for PCT/US05/39185.

Manuel Dujovny, et al., "Brain Retractor Systems," Neurological Research, vol. 37, No. 7, (2010).

O. Barlas, et al., Clincial Article, Stereotractically guided micro-surgical removal of colloid cysts, Acta Neurochir (Wien) (2004).

PCT International Search Report dated Jul. 24, 2014 for PCT/US2014/015755.

* cited by examiner

SELECTIVELY LOCKABLE HOLDING ARRANGEMENT FOR A SURGICAL ACCESS SYSTEM

CROSS-REFERENCE TO RELATED APPLICATIONS

This application is a continuation of U.S. patent application Ser. No. 16/443,142 filed Jun. 17, 2019, now U.S. Pat. No. 11,413,006 issued on Aug. 16, 2022, which is a continuation-in-part of U.S. patent application Ser. No. 15/070,739 filed Mar. 15, 2016, now U.S. Pat. No. 10,765,450 issued on Sep. 8, 2020, the disclosures of which are hereby incorporated in their entirety by reference herein.

TECHNICAL FIELD

The present disclosure relates generally to a holding arrangement for a surgical device for use with delicate and critical tissues, and more specifically to a holding arrangement that may be selectively locked by a rotation brake, as well as methods of accessing and performing surgery using same.

BACKGROUND

Diagnosis and treatment of conditions affecting the brain are among the most difficult and complex problems that face the medical profession. The brain is a complex and delicate soft multi-component tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull and the delicate network and complex interactions that form the neural communication network contained within the brain that define the human body's ability to carry on its functions of speech, sight, hearing, functional mobility, reasoning, emotions, respiration and other metabolic functions, the diagnosis and treatment of brain disorders presents unique challenges not encountered elsewhere in the body.

For example, abnormalities such as intracranial cerebral hematomas (ICH), abscesses, glioblastomas (GB), metastases (mets) and functional diseases manifest themselves in the intraparenchymal subcortical space (i.e., the white matter) of the brain are particularly challenging to access, let alone treat. The ventricles of the brain contain eloquent communication structures (neural network) which are located in the subcortical space, called fiber tracts and fascicles. Thus, traditionally, unless the ICH, GB, and/or mets were considered anything but "superficial," such conditions have been considered challenging to access, simply because getting to the abnormality ICH, GB and/or mets are considered just as damaging as letting the condition take its course. Similarly, tissue abnormalities such as tumors, cysts and fibrous membrane growths which manifest within the intraventricular space of the brain are considered challenging to safely access and often inoperable, due to their locations within the brain.

In order to assist in diagnosis and subsequent treatment of brain disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MRI), Diffusion Tensor Imaging (DTI) and Navigation systems (instrument position tracking systems). These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including fiber tracts and fascicles. If an abnormality is identified through the use of one or more imaging modalities and/or techniques, it may be necessary or desirable to biopsy or remove the abnormality.

Once a course of action has been determined based upon one or more imaging techniques, a surgical treatment may be necessary or desired. In order to operate surgically on the brain, access must be obtained through the skull and delicate brain tissue containing blood vessels and nerves that can be adversely affected by even slight disturbances. Therefore, great care must be taken in operating on the brain so as not to disturb delicate blood vessels and nerves to prevent adverse consequences resulting from a surgical intervention.

Traditionally, accessing abnormalities which manifest in deeper spaces within the brain has meant a need for a surgery that creates a highly invasive approach. In some instances, in order to obtain access to target tissue, a substantial portion of the skull is removed and entire sections of the brain are retracted to obtain access. For example, surgical brain retractors are used to pull apart or spread delicate brain tissue, which can leave pressure marks from lateral edges of the retractor. In some instances, a complication known as "retraction injury" may occur due to use of brain retractors. Of course, such techniques are not appropriate for all situations, and not all patients are able to tolerate and recover from such invasive techniques.

It is also known to access certain portions of the brain by creating a burr hole craniotomy, but only limited surgical techniques may be performed through such smaller openings. In addition, some techniques have been developed to enter through the nasal passages, opening an access hole through the occipital bone to remove tumors located, for example, in the area of the pituitary.

A significant advance in brain surgery is stereotactic surgery involving a stereotactic frame correlated to stereotactic X-ray images to guide a navigational system probe or other surgical instrument through an opening formed in the skull through brain tissue to a target lesion or other body. A related advance is frameless image guidance, in which an image of the surgical instrument is superimposed on a pre-operative image to demonstrate the location of the instrument to the surgeon and trajectory of further movement of the probe or instrument.

In recent years, surgical access systems have been developed to provide access to previously difficult to access areas. One such prior art system is shown in FIGS. 1A-1C. System 10 includes a retractor 20 and an introducer 40. Introducer 40 includes a cone-shaped distal end 42 with an opening 52 therein (best seen in FIG. 1C). The cone-shaped distal end is configured to be a generally blunt, flat surface. With introducer 40 positioned within retractor 10, system 10 is inserted into brain tissue, thereby pushing brain tissue away while providing access to an area of interest. Once system 10 is delivered to the area of interest, retractor 10 is rigidly fixed in position. More specifically, retractor 10 is fixed in space with the use of a standard or conventional neurosurgical fixation device. Once, retractor 10 is fixed in place, introducer 40 is then removed from retractor 10, while leaving retractor 10 in its fixed place, thereby creating a pathway through the brain tissue.

While access system 10 may provide a manner to access certain brain tissue, the blunt shaped distal end may cause transient or even permanent deformation and trauma of delicate tissue structures which can manifest itself in temporary or permanent neurological deficits after surgical cytoreduction due to damage of blood vessels, cranial nerves, fiber tracts and fascicles. Opening 52 may also cause coring of tissue, also leading to damage of the tissues and structures as introducer 40 is pushed through tissue. Further, by rigidly fixing the placement of retractor 10, manipulation of retractor 10 is impeded and requires constant attention by loosening and retightening to re-position for even micro-movement of the retractor 10, thereby lengthening procedure time.

Notwithstanding the foregoing advances in imaging technology and both frame and frameless stereotactic image guidance techniques, there remains a need for improved surgical techniques and apparatus for operating on brain tissue, including mechanisms for holding the surgical access system in place that allows for effective visualization, but allows some selective movement of the surgical access system, as needed.

BRIEF DESCRIPTION OF THE DRAWINGS

Exemplary embodiments of the present disclosure will now be described in greater detail with reference to the attached figures, in which.

DETAILED DESCRIPTION

Figure 1A:
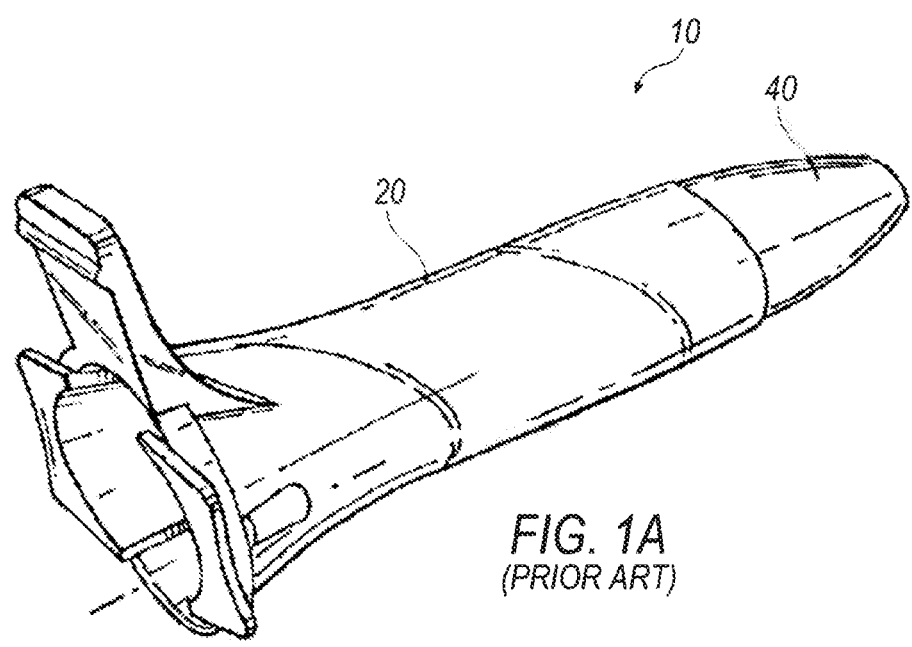
FIGS. 1A-1C illustrate a prior art surgical access system.
Figure 1B:
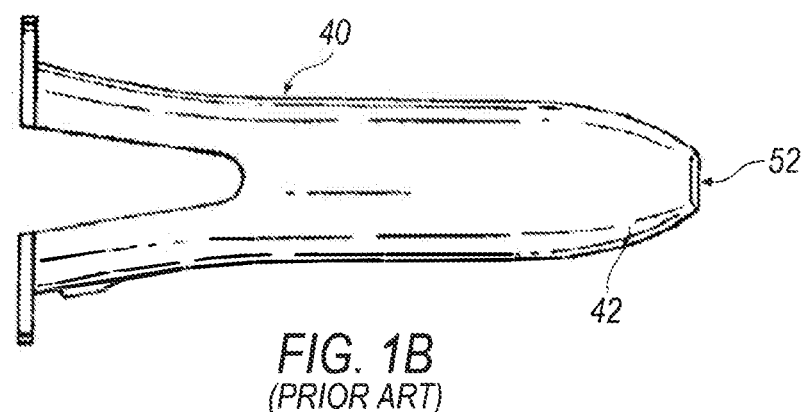

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is surgical access assembly, various components for use in same, and a method of using the surgical access assembly. The components disclosed herein provide surgeons with an enhanced ability to minimize trauma to the patient, while providing efficient improved minimally invasive surgical techniques, such as, for example, during intracranial surgical techniques. The components disclosed herein may further be used for application of targeted and effective treatment regimens.

Figure 2:
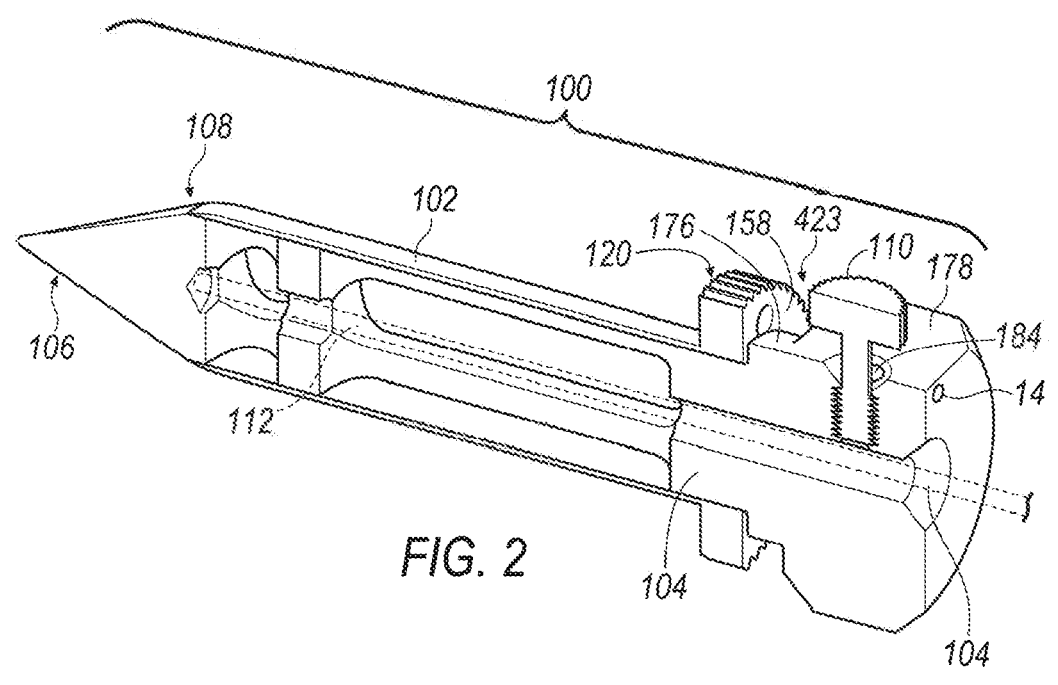
FIG. 2 is a perspective cross-sectional view of an exemplary arrangement of a surgical access assembly.

Referring to FIG. 2, a perspective cross-sectional view of a surgical access assembly 100 is shown. In one exemplary arrangement, surgical access assembly 100 comprises a hollow outer sheath 102 and a selectively removable obturator 104. As best seen in FIG. 2, obturator 104 is configured with a length that is longer than a length of outer sheath 102 such that a distal end 106 of obturator 104 protrudes a predetermined distance from a distal end 108 outer sheath 102, as will be discussed below in greater detail.

A locking member 110 may also be provided. Locking member 100 is configured to operatively retain a separate navigation member 112 (shown in phantom) within obturator 104, as will be discussed in greater detail below. A retaining member 114 may be secured within a portion of obturator 104 to prevent locking member 110 from being completely disengaged from obturator 104.

Figure 3:
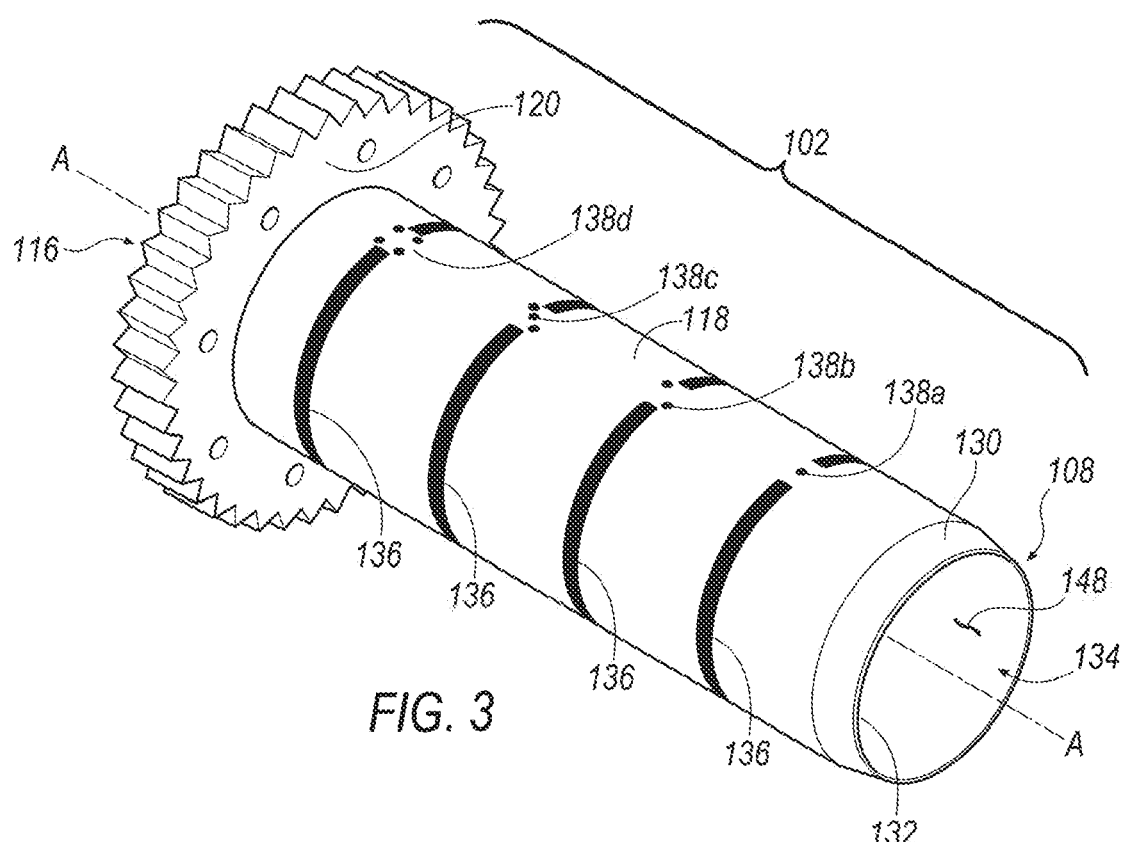
FIG. 3 is a perspective view of an outer sheath of the surgical access assembly of FIG. 2.
Figures 4A, 4B, 4C, 5:
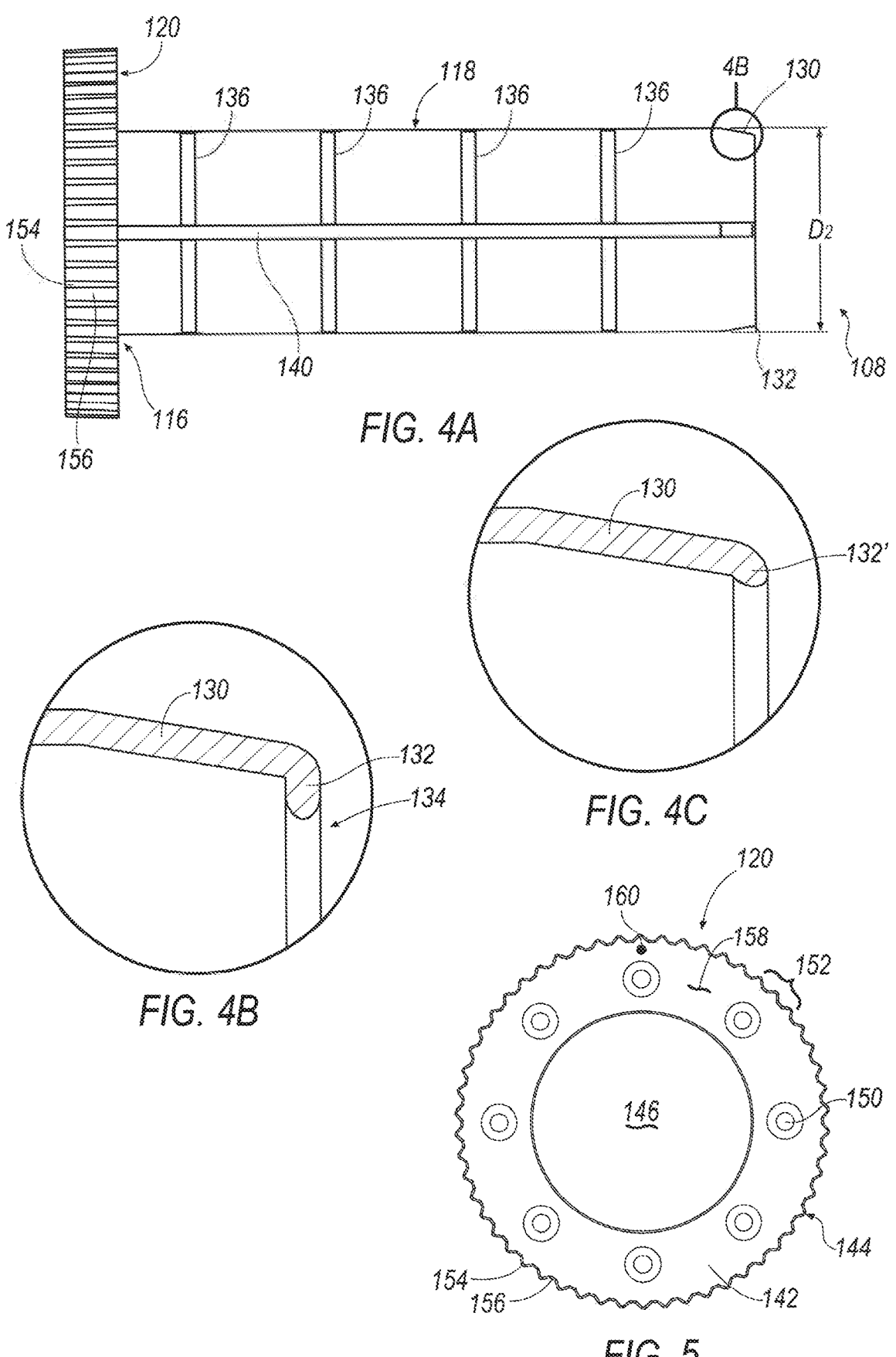
FIG. 4A is a side elevational view of the outer sheath of FIG. 3.
FIG. 4B is an enlarged cross-sectional view of a portion of the distal end of the outer sheath of FIG. 4A.
FIG. 4C is an enlarged cross-sectional view of a portion of an alternative embodiment of the distal end of the outer sheath of FIG. 4A.
FIG. 5 is an end view of outer sheath of FIG. 3.

Referring now to FIGS. 3-5, outer sheath 102 will be described in greater detail. Outer sheath 102 is defined by distal end 108 and a proximal end 116 and includes a generally hollow body portion 118 and a grip portion 120. In one exemplary arrangement, grip portion 120 is configured as a ring, as illustrated in the drawings. However, it is understood that grip portion 120 need not be configured as a ring. For ease of explanation, grip portion 120 will be referred to hereinafter as grip ring 120. Grip ring 120 is fixedly secured to body portion 118 at proximal end 116. In one exemplary arrangement, body portion 118 is constructed of a clear biocompatible material that permits viewing of normal tissue, abnormal tissue, as well as critical structures that are disposed outside of body portion 118 when outer sheath 102 is disposed within such tissue. In one exemplary arrangement, outer sheath 102 is constructed of polycarbonate, though other biocompatible materials may be employed, including resins.

In one exemplary configuration, an imaging mechanism may be incorporated into outer sheath 102 that would permit visualization of tumors, vessels, fiber tracks, fascicles and even healthy tissue, in real-time. Indeed, as will be explained in further detail below, the imaging mechanism will enable physiological functional imaging to provide information about the characteristics of the cortical fiber tracks to be visible, thereby enabling a user to separate and park such fibers on either side of outer sheath 102 rather than cutting, stretching and potentially damaging such fibers while gaining access to a desired location within the brain. Further, as will be explained in further detail below, the imaging mechanism may also enable the surgeon to have real-time information about the fiber tract and fascicle location, after placement of outer sheath 104, and during abnormality resection procedure therethrough. In addition to white matter tract imaging, mapping of the characteristics of the cerebral blood flow may be obtained.

In one exemplary embodiment, the imaging mechanism may be an ultrasound probe incorporated into outer sheath 102. For example, outer sheath 102 may be provided with one or more channels within the wall that defines outer sheath 102 that are configured with one or more small diameter ultrasound probes. In another arrangement, a single ultrasound probe that is configured to be received within outer sheath 102 may be provided. In yet another embodiment, a low field Mill probe may be selectively placed in outer sheath 102 to provide enhanced imaging. In yet another embodiment a low field Mill imaging coil may be molded into or bonded into outer sheath 102. In still another exemplary arrangement, the probe may be an optical coherent tomography (OCT) imaging or spectroscopy.

In another exemplary arrangement, as will be explained in further detail below, outer sheath 102 may also be (or alternatively be) provided navigational capabilities that permit a user to "read" the location of outer shaft 102 after placement at an area of interest, as well as update the location of outer sheath 102 during a procedure. In one exemplary arrangement, an RFID chip or sensor that is configured to be tracked by a navigation system may be incorporated into outer sheath 102. For example, an RFID chip or sensor may be permanently attached to outer sheath 102, for example, by impregnating or molding the RFID chip or sensor therein. In other exemplary arrangements, a temporary sensor or chip may be incorporated into or attached to outer sheath 102. For example, outer sheath 102 may be provided with one or more channels within the wall that defines outer sheath 102. An RFID chip and/or sensor may be positioned within the channels.

Distal end 108 of outer sheath 102 may be configured with a tapered portion 130 that extends towards a center axis A-A of outer sheath 102 to a distal edge 132 that surrounds an opening 134 in distal end 108 of outer sheath 102. Tapered portion 130 serves to ease the transition between outer sheath 102 and a distal tip portion 172, without drag, trauma or coring of tissue from a diameter that defines a body portion 168 of obturator 104 to a diameter that defines body portion 118 of outer sheath 102. In one exemplary configuration, distal end 108 may be configured with a radius or other configuration so as to create a smooth/atraumatic transition of the brain tissue when surgical access assembly 100 is inserted into the brain.

Figure 1C:
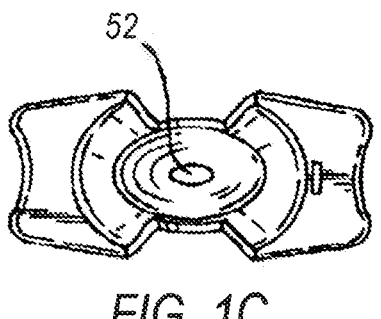

For example, as best seen in FIG. 4B, distal edge 132 is configured so as to be non-sharpened and radiused. In one exemplary arrangement, distal edge 132 is configured as a 0.3 mm diameter radiused rim. Tapered portion 130 and radiused distal tip 132 cooperates with obturator 104 to atraumatically move tissue, as well as various structures within the brain, including white matter, away from outer sheath 102 without cutting tissue or such structures. Indeed, unlike prior art devices that include either a blunt tip distal end or a tapered leading edge such as that shown in FIG. 1C, radiused distal tip 132 cooperates with tapered portion 130 and obturator 104 to prevent bruising and damage to various tissue. More specifically, this configuration facilitates entry of outer sheath 102 into delicate tissue, but without cutting such delicate tissue. Insertion of surgical access assembly 100 will be explained in further detail below.

Body portion 118 may further be provided with a plurality of spaced apart indicators 136. Indicators 136 generally extend about the circumference of body portion 118 and each may further incorporate a secondary indicator 138 that visually illustrates a predetermined location on body portion 118, as shown in FIG. 3. While FIG. 3 illustrates four indicators 136, it is understood that body portion 118 may be provided in a variety of lengths and that any number of indicators 136 may be provided. Body portion 118 may also be provided with a longitudinal indicator 140. More specifically, as best seen in FIG. 4A, longitudinal indicator 140 extends from proximal end 116 to distal end 108. Indicators 136, 138 and 140 may be printed onto either an internal or external surface of body portion 118 with an imaging visible ink such as, for example ink containing fluro-deoxyglucose (FDG), Technicium 99, Gadolinium, titanium dust, barium sulfate, a combination of the above or other suitable imaging material. Indicators 136 and 138 provide a reference point for the operator of system 100, as structures may be visible through body portion 118. Indicator 136, 138 and 140 may also be configured to be visible under MM, CT, PET, or any other suitable imaging modality to enable easy identification of areas of interest. In one alternative embodiment, indicators 136, 138 and/or 140 may be etched or printed onto body portion 118, either on the internal or external surface of body portion 118.

Details of grip ring 120 are best seen in FIG. 5. Grip ring 120 is generally configured as a flange member 142 defined by an outer periphery 144 and an inner opening 146. Inner opening 146 may be sized to generally correspond to the diameter of a lumen 148 defined by body portion 118. Outer periphery 144 is sized to have a diameter that is larger than lumen 148 of body portion 26. Flange member 142 may further be provided with one or more small openings 150 that are disposed therein. In one exemplary arrangement, a plurality of small openings 150 are provided that are spaced generally equi-distantly about inner opening 146. Small openings 150 will be described in further detail below. Outer periphery 144 may further be provided with a textured surface 152 to provide for ease of gripping outer sheath 102. For example, in one exemplary arrangement, textured surface 152 comprises a plurality of alternating ridges 154 and grooves 156. However, it is understood that other textured surfaces may be employed.

Disposed on a proximal end surface 158 of flange member 142, an alignment feature 160 may be employed. Alignment feature 160 is used to indicate the location of longitudinal indicator 140 when outer sheath 102 is positioned within the brain. Alignment feature 160 will be discussed below in greater detail.

Figure 6A:
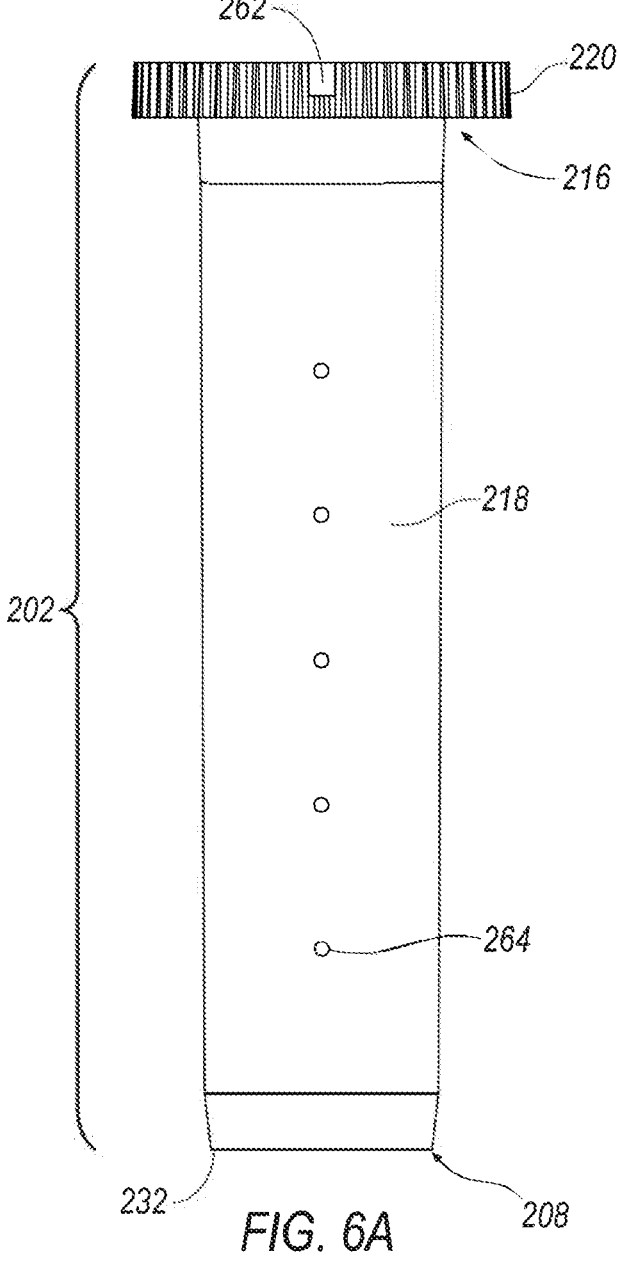
FIG. 6A is an elevational view of an alternative embodiment of an outer sheath.
Figure 6B:
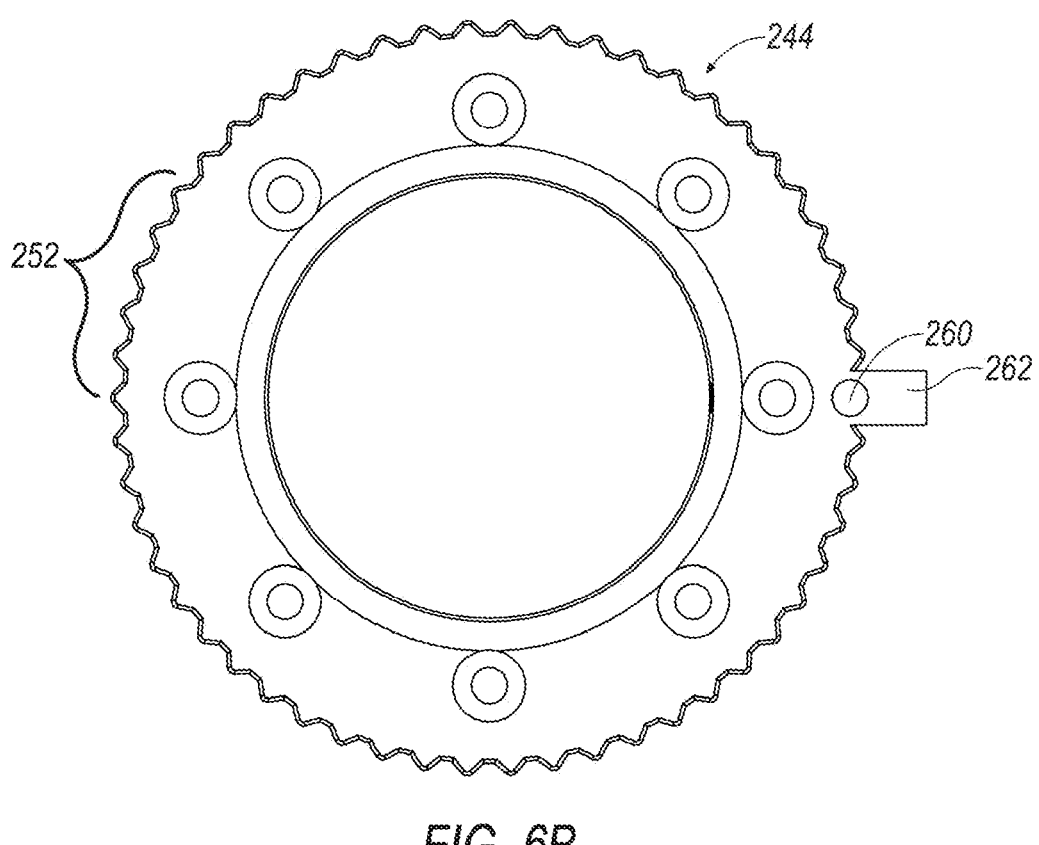
FIG. 6B is an end view of the outer sheath of FIG. 6A.

An alternative embodiment of outer sheath 202 is shown in FIGS. 6A-6B. Outer sheath 202 is similar to outer sheath 102 in that it is defined by a distal end 208, a proximal end 216 and a body portion 218. A distal edge 232 is generally configured to be similar as distal tip 132. A grip ring 220 is fixedly secured to body portion 218. Grip ring 220 may also include a textured surface 252.

Grip ring 220 further includes a locating member 262. Locating member 262 is configured to operatively connect an illumination ring (as described in co-pending U.S. patent application Ser. No. 13/444,722, the contents of which are incorporated by reference) to outer sheath 102. As may be seen, in one exemplary configuration, locating member 262 extends outwardly from outer periphery 244 of grip ring 220. Locating member 262 may also serve as an alignment feature for indicating the location of longitudinal indicator 240. Alternatively, a separate alignment feature 260 may be provided. For example, in FIG. 6B, alignment feature 260 is positioned adjacent locating member 262.

Body portion 218 may also be provided with indicators 34, 36, and 38 to assist in locating outer sheath 202 in operation. However, in another alternative arrangement, body portion 218 may be provided with indicators 264 that produce a signal void or minimal artifact under certain imaging modalities. In one specific arrangement, indicators 264 may be configured as small holes that are spaced apart at predetermined distances, as shown in FIG. 6A. In yet another alternative arrangement, indicators 264 may be configured as non-through divots. In still a further alternative arrangement, indicators 264 may be configured as a longitudinal groove (not shown) on either the internal or external surface of body portion 218.

Referring to FIGS. 7-10, obturator 104 will now be described. Obturator 104 is defined by distal end 106, a proximal end 166, a body portion 168 and a handle portion 170. Distal end 106 is configured with a generally conical shaped distal tip portion 172 that tapers to a tip member 174 to provide atraumatic dilation of tissue. In one exemplary arrangement, tip portion 172 tapers toward a closed tip member 174 so as to prevent coring of tissue as obturator 104 is inserted into the brain.

There are a number of variables that play the selection of the angle α that defines the taper of tip portion 172. These variables include the size of an outer diameter D1 of obturator 104, the desired length that distal tip portion 172 extends from body portion 168, and the desired offset for a distal tip of navigation member 112 and tip member 174. More specifically, it is contemplated that surgical access assembly 100 will be provided as part of a kit that may include multiple sized outer sheaths 102 and obturators 104, to provide the surgeon with a choice of different diameter sizes and lengths so as to provide flexibility for accessing areas of interest within the brain. However, to insure that the distal tip 174 is determinable regardless of which size diameter D1 of obturator 104 is used, taper angle α may be selectively adjusted. For embodiments that utilize navigation member 112 that positions a distal end thereof at a set position within obturator 104 (as will be explained in further detail below), to maintain an identical offset length between the distal end of navigation member 112 and distal tip 174 in different diameter D1 sized obturators 104, taper angle α will need to be increased, as diameter D1 increases.

For example, if diameter D1 of obturator 104 is 13.5 mm, an exemplary angle α may be 45.5° to provide effective atraumatic dilation, as well as a determinable distal tip 174 location. However, if diameter D1 of obturator 104 is 15.5 mm, an exemplary angle α' may be 52.8°.

Figure 8A:
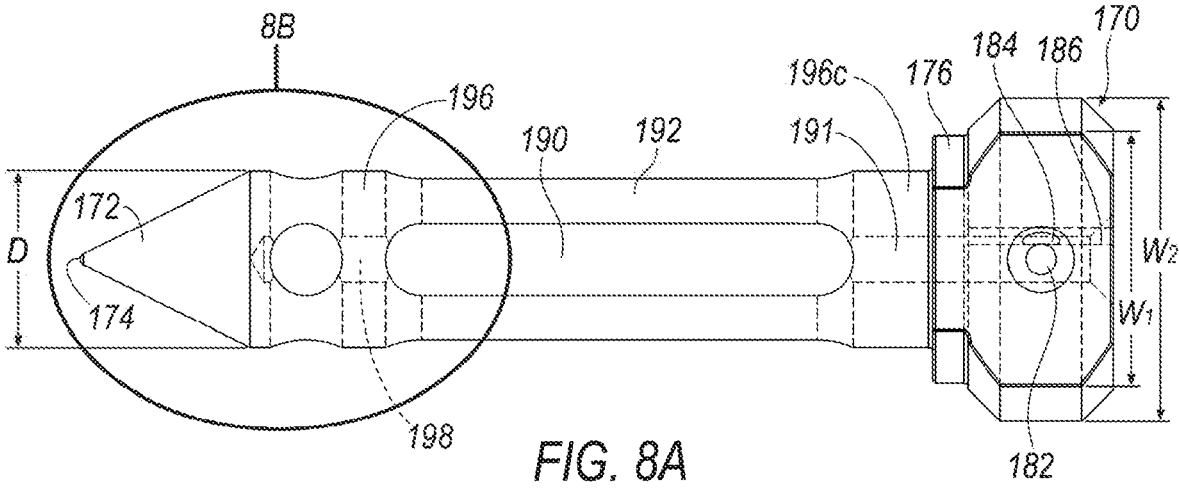
FIG. 8A is a top view of the obturator assembly of FIG. 7A.
Figure 8B:
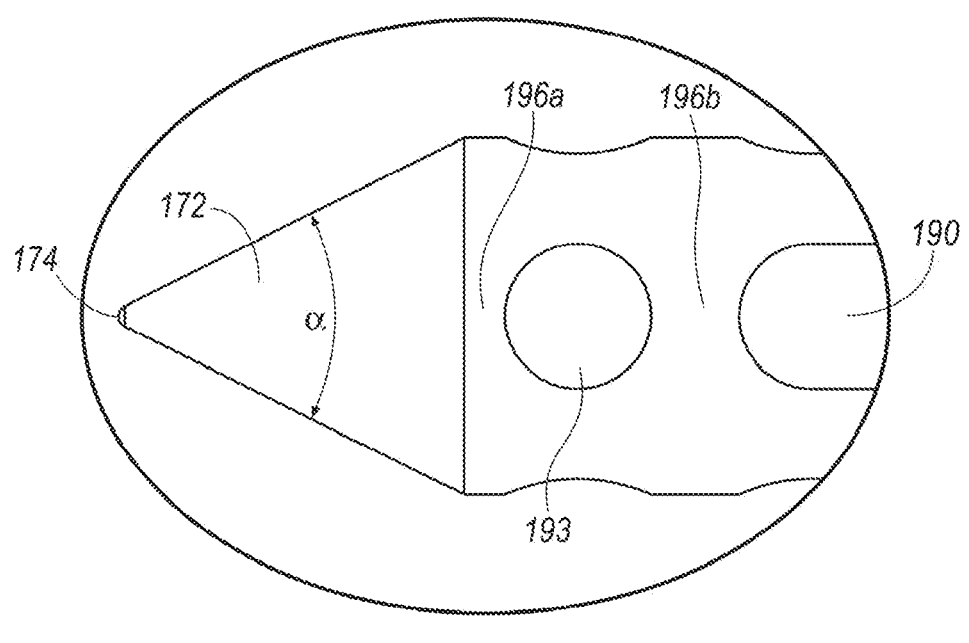
FIG. 8B is an enlarged view of a distal end of the obturator assembly taken from area 8B of FIG. 8A.
Figure 8C:
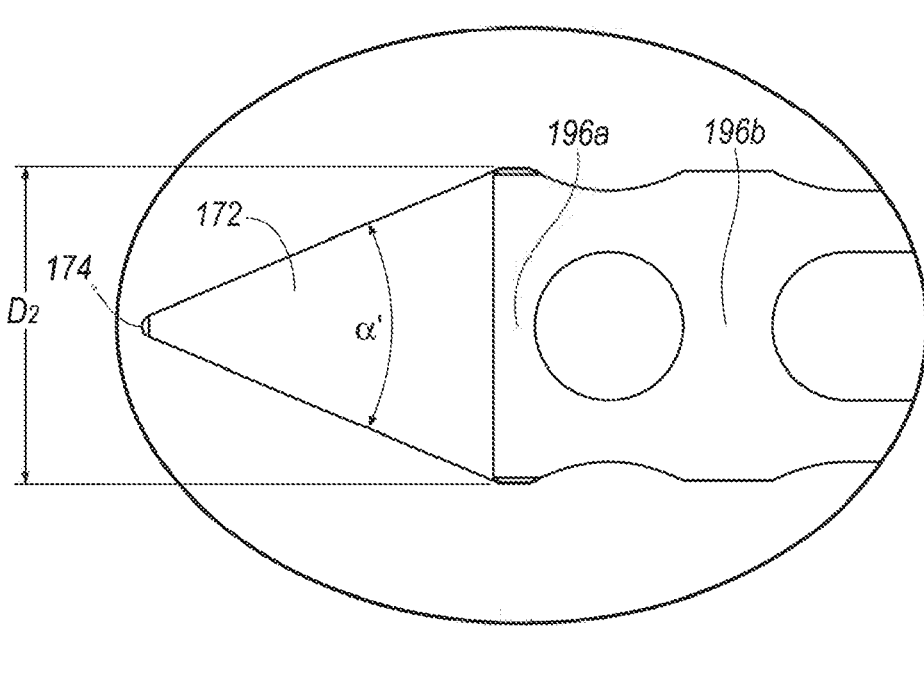
FIG. 8C is an alternative embodiment of the distal end of the obturator assembly taken from area 8B of FIG. 8A.

As best seen in FIG. 8B, distal tip 174 is configured to be radiused such that tip member 174 is rounded, and neither blunt, nor sharp. More specifically, tip member 174 is configured so as not to have any flat portions which during insertion can stretch or even tear the delicate tissues such as the vessels, fiber tracts and fascicles found in the brain. Further, because tip member 174 is closed, damage of such delicate tissues and fascicles are also avoided. In one exemplary embodiment, tip member 174 is configured with a 0.5 mm radius. As will be explained in further detail below, the configuration of tip member 174 is designed to gently displace and move the tissue into which it is inserted; i.e., atraumatically dilate the tissue to allow for introduction in to an intra-fascicular and para-fascicular manner, as opposed to cutting tissue as surgical access assembly 100 is inserted into the tissue.

Figure 9A:
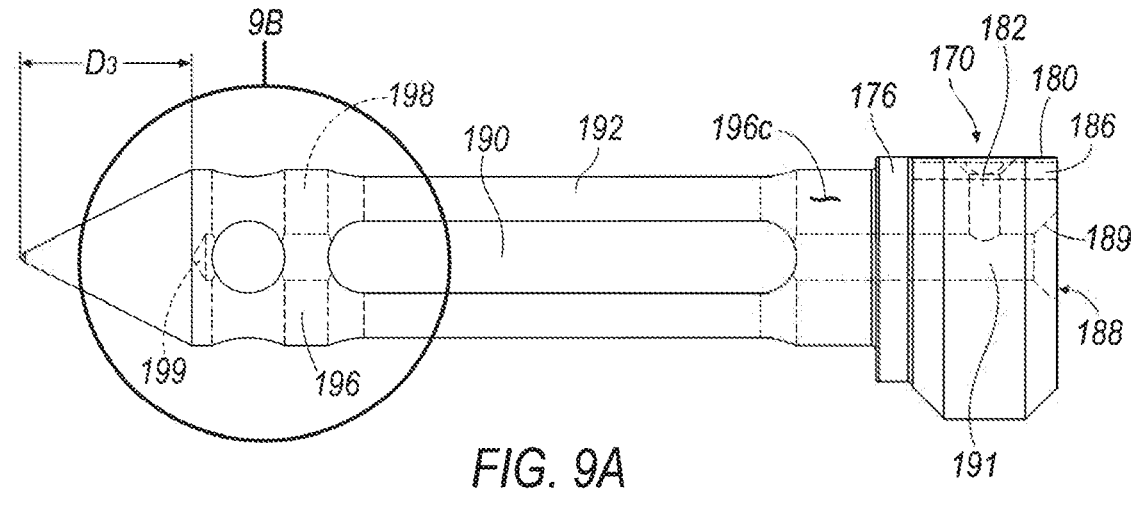
FIG. 9A is a side elevational view of the obturator assembly of FIG. 7A.

Handle portion 170 is positioned at proximal end 166 of obturator 104. As best seen in FIGS. 7B, 8A and 9A, handle portion 170 comprises a stop member 176 and a grip member 178. Stop member 176 is positioned distally of grip member 178 and, as best seen in FIG. 8A, is configured to have a width W1 that is greater than a diameter D1 of body portion 168, as well as a diameter D2 of outer sheath 102 (shown in FIG. 4A). Grip member 178 is configured with a width W2 that is greater than the width W1 of stop member 176, thereby providing a step-like configuration. Stop member 176 further defines an engagement surface 177 that is axially spaced from a distal surface 179 of grip member 178.

Figure 7A:
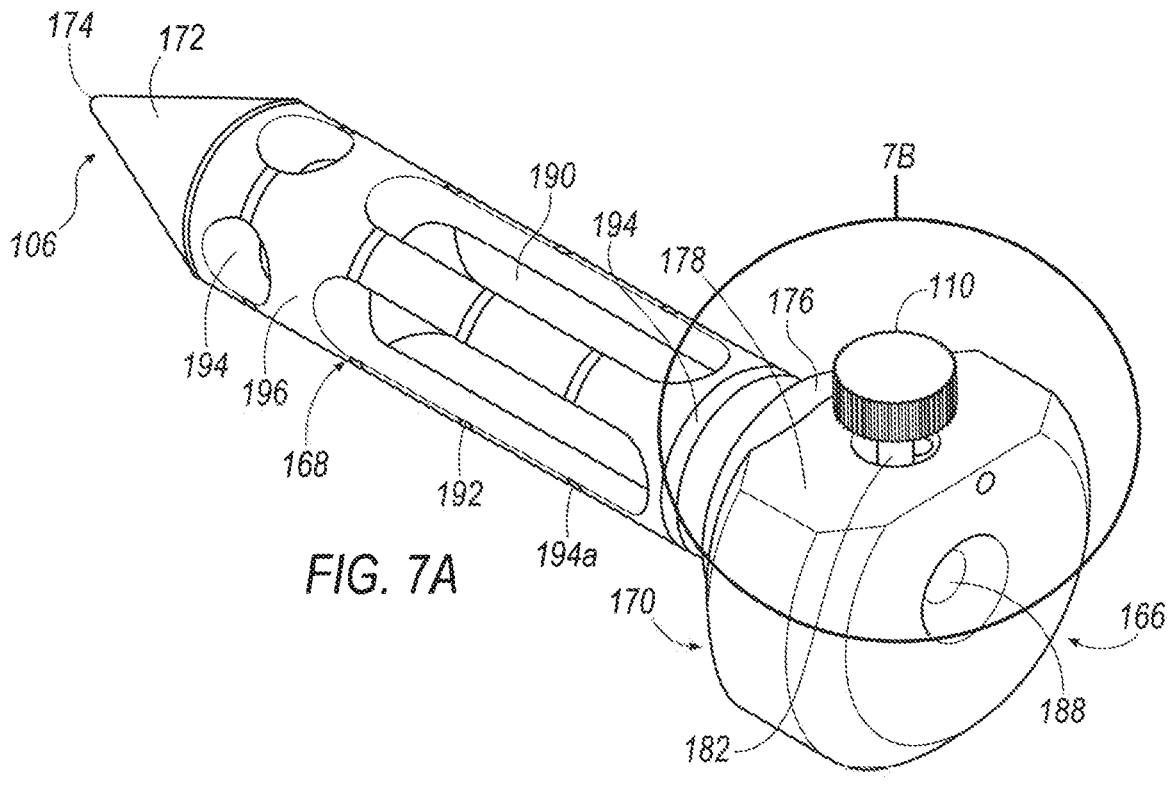
FIG. 7A is a perspective view of an obturator assembly of the surgical access assembly of FIG. 2.
Figure 7B:
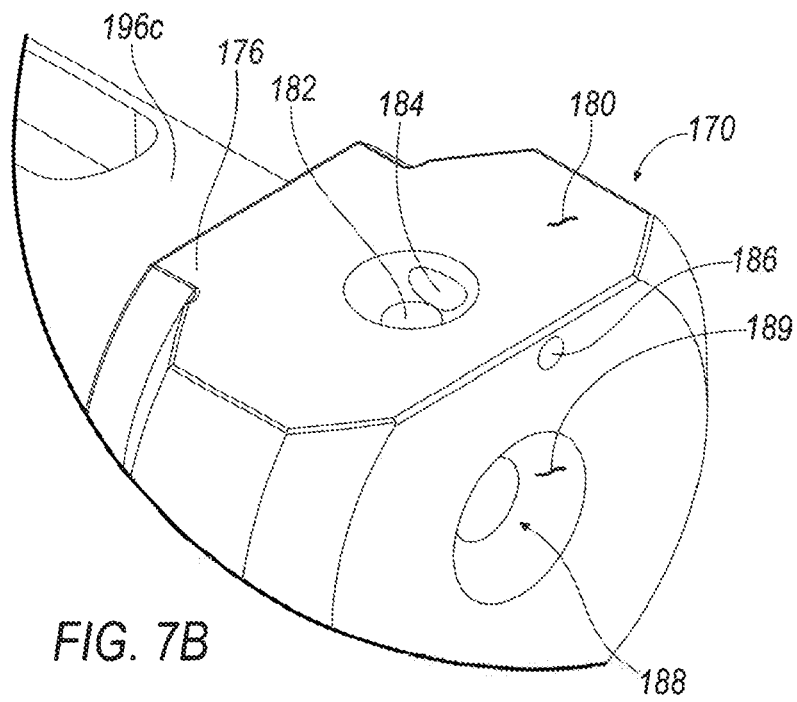
FIG. 7B is an enlarged view of an end face of the obturator assembly taken from area 7B of FIG. 7A.
Figure 10:
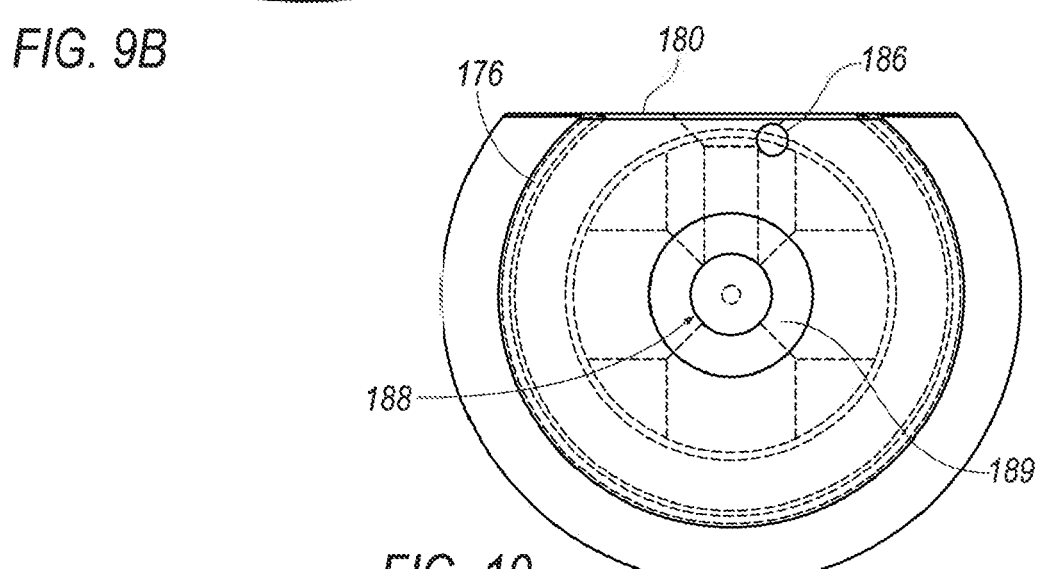
FIG. 10 is an end view of the obturator assembly of FIG. 7A.

In one exemplary arrangement, handle portion 170 is configured with a generally planar surface 180, as best seen in FIGS. 7A-7B and FIG. 10. Planar surface 180 is configured with a receiving aperture 182 that is configured to receive locking member 110. In one exemplary arrangement, receiving aperture 182 is threaded. As best seen in FIGS. 2, 7B, and 8A, disposed within receiving aperture 182 is an engagement opening 184. Engagement opening 184 is in communication with a channel 186 (seen in phantom in FIGS. 8A and 9A) that extends at least partially thorough handle portion 170. After locking member 110 is at least partially engaged within receiving aperture 182, retaining member 114 (FIG. 2) is positioned within channel 186. Because engagement opening 184 opens into receiving aperture 182, a portion of retaining member 114 extends across a portion of receiving aperture 182 such that locking member 110 is prevented from being entirely withdrawn from receiving aperture 182. For example, locking member 110 is illustrated as having threads that cooperate with corresponding internal threads in receiving aperture 182. Retaining member 114 is positioned within channel 186 so as to extend above the threads of locking member 110 such as locking member 110 is being removed from receiving aperture 182, threads come into contact retaining member

114, thereby preventing complete removal of locking member 110 from handle portion 170.

An access opening 188 is formed through proximal end 166. Access opening 188 extends through handle portion 170. In one exemplary arrangement, access opening 188 may be provided with an inwardly extending chamfer 189 that tapers toward access opening 188. Chamfer 189 provides a self-directing feature for inserting navigation member 112 into access opening 188. Access opening 188 is in communication with a first channel segment 191 that extends through handle portion 170 and into body portion 168.

Figure 8D:
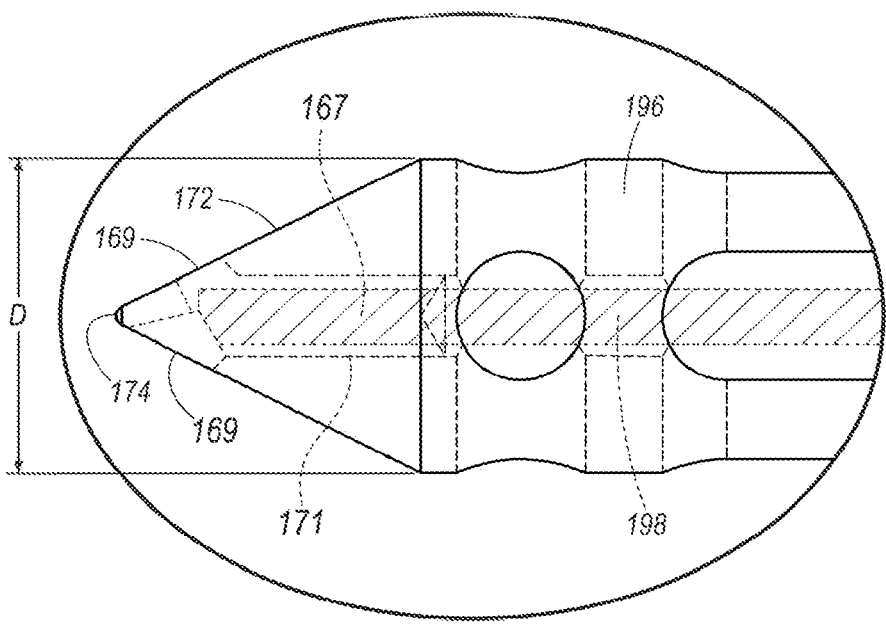
FIG. 8D is an alternative embodiment of the distal end of the obturator assembly taken from area 8B of FIG. 8A.

As seen in FIG. 8D, obturator 104 may further be configured to receive a viewing member 167 operatively connected thereto. More specifically, conical tip portion 172 may be configured with one or more viewing windows 169 that are oriented to be flush with the surface of conical tip portion 172. Viewing windows 169 are in communication with a viewing member channel 171 that may selectively receive a viewing member such as, for example, a fiber optic cable or an ultrasound probe. The viewing member may be in addition to the use of navigation member, or in place thereof. The viewing member permits the surgeon to observe, in real-time (i.e., during insertion), surrounding tissue and eloquent tissue structures so as to minimize trauma during insertion.

Body portion 168 extends between distal end 106 and proximal end 166. Body portion 168 includes one or more elongated void areas 190. Void areas 190 serve to reduce weight of obturator 104, thereby making obturator 104 easier to manipulate during surgical procedures. Void areas 190 also facilitate sterilization of obturator 104 by moisture retention within body portion 168 of obturator 104. Further, void areas 190 also provide venting, thereby preventing a vacuum from being generated as obturator 104 is being withdrawn from outer sheath 102 during operation.

Void areas 190 are separated by web portions 192 that extend axially through a portion of the length of body portion 168. Disposed on web portions 192 of body portion 168 are one or more indicators 194. Indicators 194 may include spaced apart hash marks (designated as 194A) that cooperate with an imaging modality to provide information, in real-time, concerning the location of obturator 104 relative to various tissue, critical structures, and fascicles within the brain, while obturator 104 is positioned within tissue. Indicators 194 also assist with providing information to regarding the relative positions between obturator 104 and outer sheath 102. Indicators 194 produce a signal void or minimal artifact under certain imaging modalities.

Body portion 168 may further include one or more cross webs 196. Cross webs 196 are oriented transverse to web portions 192 and connect web portions 192 together. In one exemplary arrangement, body portion 168 includes at least one cross web 196 that operatively defines the outer diameter D2 of body portion 168. Diameter D2 is sized to fit within lumen 148 of outer sheath 102 such that obturator 104 and outer sheath 102 may be selectively slid relative to one another. However, diameter D2 is also sized to minimize or even eliminate any gaps between an inner surface of outer sheath 102 and an outer surface of obturator 104. In the exemplary arrangement shown in FIG. 7-9, three cross webs 196A, 196B and 196C are provided. A first cross web 196A is connected to distal tip portion 172, while second cross web 196B is spaced proximally from first cross web 196A and separated by a void area 193. Third cross web 196C is separated from second cross web 196B by void areas 192 and is positioned distal from first stop member 176 of handle portion 170. Cross webs 196 serve to provide for structural integrity of obturator 104, as well as improved rigidity.

In one exemplary arrangement, one or more of cross webs 196 may further be provided with an annular compensating protuberance 197 to accommodate for slight manufacturing variations of the diameter of lumen 148 of outer sheath 102. For example, as it is contemplated that outer sheath 102 may be a component that is molded from a resin, a process which may produce such slight manufacturing variations. Compensating protuberance 197 extends slightly radially outwardly from an outer surface of obturator 104 and cooperates with lumen 148 of outer sheath 102 to create a friction fit between the outer surface of obturator 104 and lumen 148, due to the slight flexibility of the resin of outer sheath 102. Use of compensating protuberance 197 thereby reducing the need for maintaining a high dimensional tolerance of outer sheath 102 in production.

Figure 9B:
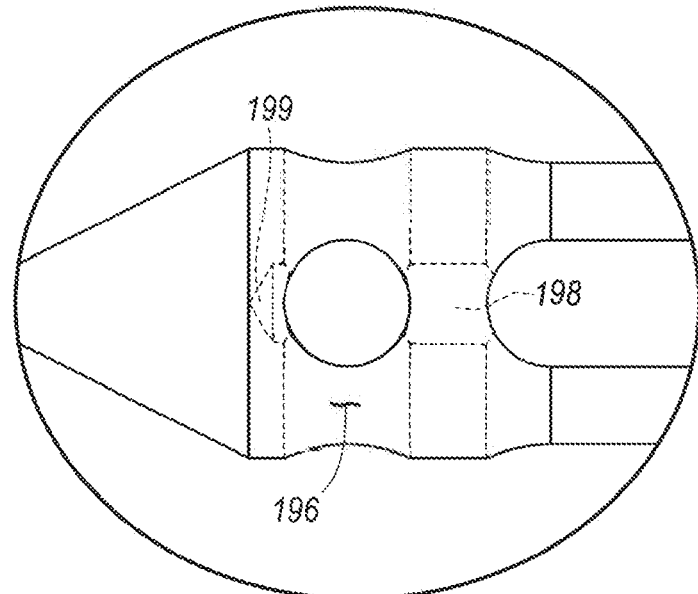
FIG. 9B is an enlarged view of a portion of the obturator assembly taken from area 9B of FIG. 9A.

In one embodiment, cross web 196B is provided with a second channel segment 198 (shown in phantom) that extends there through. Second channel segment 198 is axially aligned with first channel segment 191 and is configured to selectively receive navigation member 112. In one exemplary arrangement, disposed in first cross web 196A is an inwardly extending depression 199, as best seen in FIG. 9B. Depression 199 is configured in such a manner so as to align a distal tip of navigation member 112 with distal end 108 of outer sheath 102, when outer sheath 102 is assembled to obturator 104.

Figure 11A:
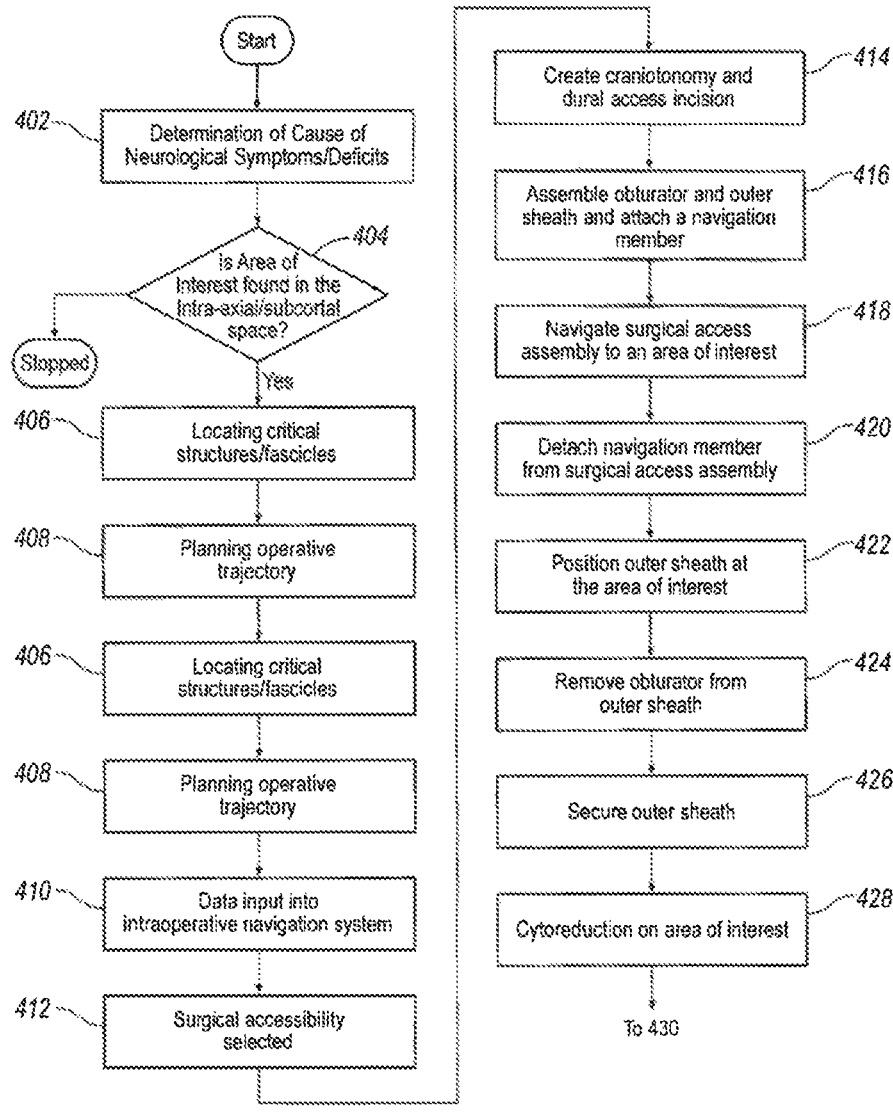
FIGS. 11A and 11B are a flow chart illustrating a process flow using the surgical access assembly.
Figure 11B:
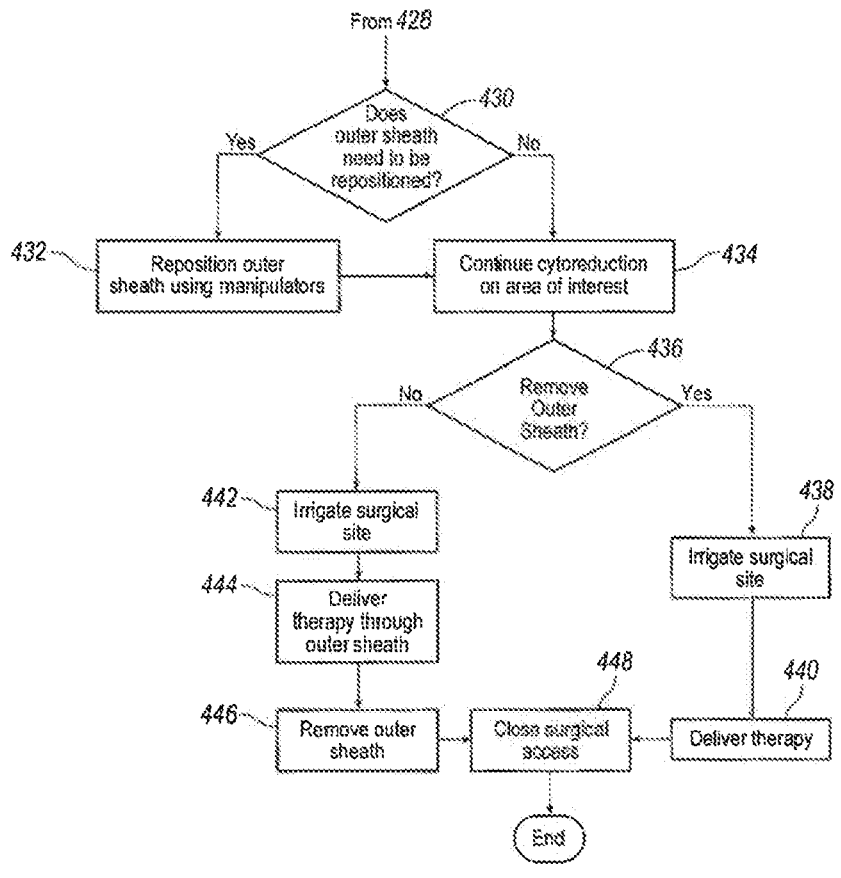

Operation of surgical access assembly will be described in connection with a process flow 400 illustrated FIGS. 11A and 11B. Generally speaking, before any surgical procedure is decided upon, a patient will first present with symptoms or deficits requiring evaluation. Thus, the start of process flow 400 begins with a surgeon making a determination 402 of the cause of such neurological symptoms/deficits. Such a determination may be made through use of a variety of imaging modalities, including, but not limited to, MRI or CT imaging. The process then proceeds to step 404.

If the determination from step 402 finds that a brain condition is found, such as a tumor or hematoma, an additional determination is required. More specifically, a location of the brain condition is determined in step 404. If the imaging determines that an area of interest is located in the intra-axial/subcortical space, the process flow continues to step 406. However, if a brain condition is located in other, more easily accessible areas of the brain, the process flow stops.

Figure 12A:
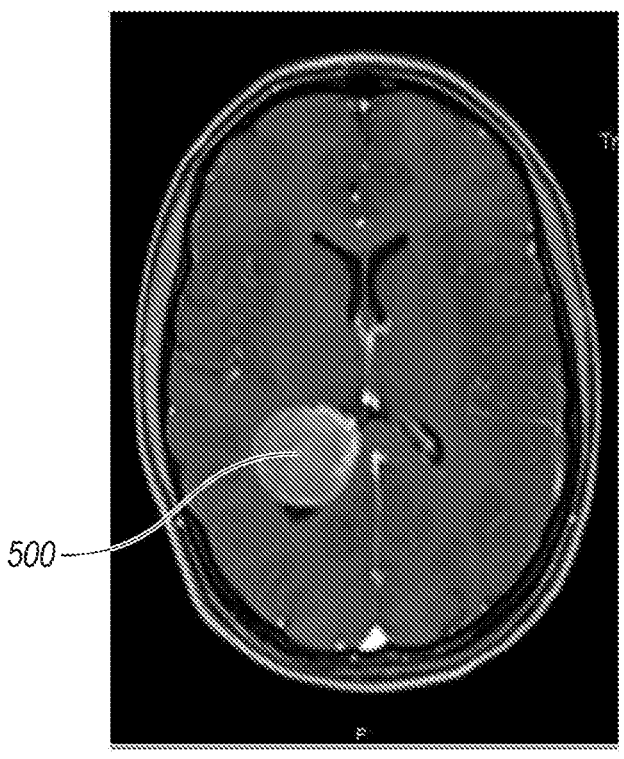
FIGS. 12A-12B are images of a brain illustrating an area of interest, taken using an imaging modality.
Figure 12B:
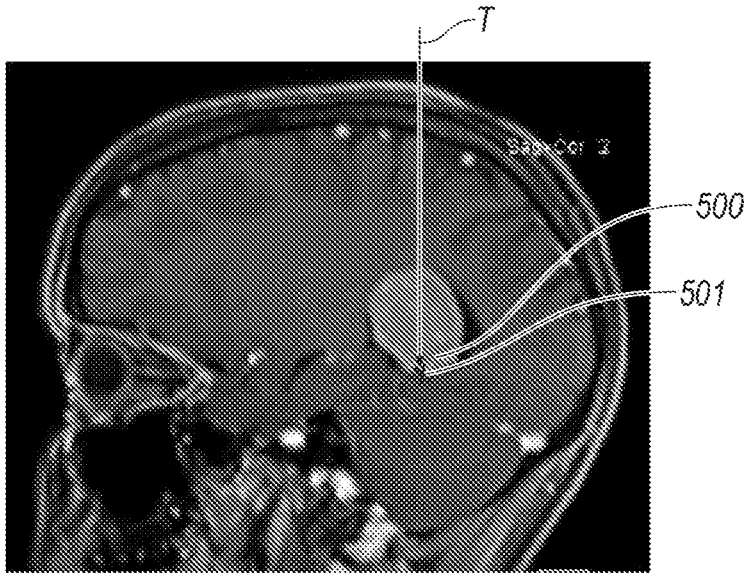

As discussed above, any suitable imaging modality may be utilized to determine if a brain condition exists, and if so, where that brain condition is located. FIGS. 12A and 12B illustrate examples of imaging results from an MM. More specifically, an area of interest 500, in this case a tumor, may be seen deep in the subcoritcal space.

Once area of interest 500 is located, at step 406 an additional imaging sequence is employed to determine the location of eloquent structures such as vessels and fiber tracts and the associated fascicles so as to plan the safest access route to the area of interest. Exemplary arrangements for accomplishing this step include CT-Angiography and MM with Diffusion Tensor Imaging (DTI) sequences. DTI allows for the determination of directionality as well as the magnitude of water diffusion along the communication "wiring" pathways called fiber tracts and fascicles. This kind of MRI imaging can provide imaging to allow for the estimation of potential damage to nerve fibers that connect the areas of the brain which can be affected by a stroke, for example, to brain regions that are distant from it, and can also be used to visualize white matter fibers in the brain and can map (trace image) subtle changes in the white matter associated with diseases such as multiple sclerosis and epilepsy, as well as assessing diseases where the brain's wiring is abnormal, such as schizophrenia, as well as tumor involvement.

Diffusion Tensor Tractography (DTT) may also be used. DTT allows for noninvasive racking of neuronal fiber projections in a living human brain. White matter fiber trajectories are reconstructed throughout the brain by tracking the direction of fastest diffusion, which is assumed to correspond to the longitudinal axis of the tract. Diffusion tensor tractography provides insight into white matter integrity, fiber connectivity, surgical planning, and patients' prognosis. Once the imaging information has been analyzed, the process then proceeds to step 408.

Figure 13:
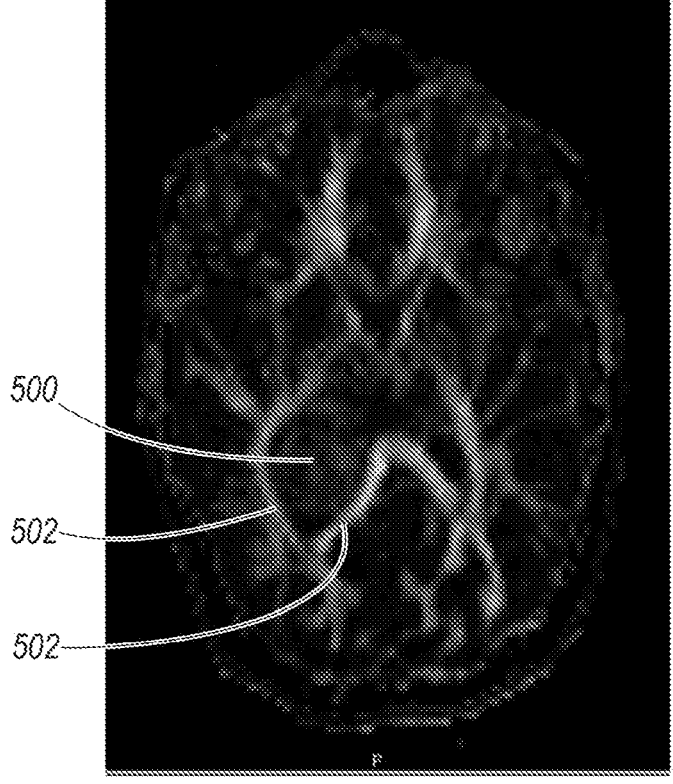
FIG. 13 is an image taken of the brain shown in FIGS. 12A-12B, illustrating various critical structures, such as fiber tracts and fascicles of the brain.

Referring to FIG. 13, an example of DTI imaging of the brain shown in FIGS. 12A and 12B is depicted. A map of fascicles and other vessels are illustrated in FIG. 13, including major vessels 502 that are shown spread around area of interest 500. Such images provide the surgeon with valuable information about potential avenues for access tracts to area of interest 500.

In step 408, a plan for the operative trajectory is developed. More specifically, imaging information is used to plan (either manually or with software) the access tract/pathway to achieve fiber tract involvement during access to the area of interest. In evaluating fiber tract involvement from a potential access tract/pathway, consideration of fiber tract importance may be based on an individual patient's occupational and personal needs and/or preference. Once a pathway has been planned, the process proceeds to step 410.

In step 410, image data from the MRI/DTI and CT/CTA image sequence obtained during step 406 is input into an intraoperative navigation system. Intraoperative navigation systems may be used to provide direct visualization of area of interest 500 in real time, as surgical access system 100 is being positioned within the brain. The method then proceeds to step 412.

Once the procedure has been planned and the image data has been uploaded to a navigational system, step 412 requires that the appropriate sized surgical access assembly 100 is selected. First the appropriate size of a craniotomy must be determined. Further, the present disclosure contemplates that different diameter and length sizes of surgical access assembly 100 may be employed, the size depending on the particular location of area of interest 500. Accordingly, step 412 requires that the surgeon select the appropriate length and diameter of surgical access system 100 to be used, based on the physical and location characteristics of the area of interest 500. Once surgical access assembly 100 is selected, the process proceeds to step 414.

In step 414, the surgeon creates the craniotomy and Dural access incision. The process then proceeds to step 416.

In step 416, the obturator 104 is inserted into outer sheath 102 until grip ring 120 abuts first stop member 176, as shown in, for example FIG. 2. Navigation member 112 is then operatively connected to obturator 104.

As discussed above, various types of navigation members 112 may be employed with surgical access assembly 100. In one exemplary configuration, navigation member 112 is configured as a probe (as shown in FIG. 2). In this configuration, navigation member 112 is inserted through access opening 188 of grip member 178 until a distal tip 417 of navigation member 112 is deposited into depression 199 (see FIG. 9B). Depression 199 is formed so that distal tip 471 of navigation member 112 is positioned within the same plane as distal tip 132 of outer sheath 102, when obturator 102 and outer sheath 104 are assembled together as shown in FIG. 2. Locking member 110 may be tightened to fixedly retain navigation member 112 within obturator 102. A portion of navigation member 112 will extend proximally from grip member 178 and will be operatively connected to a navigation system that includes a screen that visually illustrates the information obtained from the imaging sequences, along with the trajectory of surgical access system 100. Thus, with the navigation member 112 operatively connected to a navigation system, the position of distal tip 132 of outer sheath may be indicated, in real time, while surgical access system 100 is being navigated within a body.

In another configuration, the software operating the navigation system may further be provided with an offset dimension that corresponds to a distance D3 between distal tip 174 of obturator 104 and distal tip 132 of outer sheath. In this arrangement, a dotted line may appear on the navigation screen that indicates where distal tip 174 of obturator 104 is located, in real-time.

Navigation member 112 may further be provided with image guidance position indicators, such as an array of reflectors of the type use in connection with optical image guidance systems. The infrared reflectors used with such a system are mounted to a handle of a probe-like navigation member 112 in a customary triangular configuration calibrated to identify the tool to the image guidance system. Such imaging systems are available, for example Medtronic Surgical Navigation Technologies (Denver, Colo.), Stryker (Kalamazoo, Mich.), and Radionics (Burlington Mass.).

Typically, the positioning of the indicators is calibrated such that the image guidance system can project an image of the tool onto a display of images of the patient's brain, such as MRI images used to plan surgery. Thus, as discussed above, as surgical access system 100 is inserted, the surgeon can see the relative position of system 100 relative to the structures of the brain as reflected on images, and particularly with respect to the target tissue.

Other guidance systems, such as magnetic or electromagnetic or radio transmitting systems may also be used, and the illustration of infrared reflectors and discussion of optical image guidance systems are exemplary only and are not intended to be limiting. In addition, while the exemplary method has been described in connection with superimposing an image of surgical access system 100 onto a pre-operative image, it is contemplated that real-time imaging capability may be utilized and that the image of surgical access system 100 may then be shown in relation to the surrounding tissue structures on a real time image.

In another exemplary configuration, an RFID chip may be embedded in obturator 104 that operatively communicates information to a navigation system or other surgical system about the specific attributes, such as, but not limited to, length and diameter. This information may be used to facilitate placement with the navigation system or other systems for information display or trajectory and location calculations during placement of obturator 104. Other navigational arrangements are contemplated, such as those disclosed in co-pending U.S. patent application Ser. No. 13/444,722, the contents of which are incorporated herein by reference.

Once surgical access assembly 100 is assembled and operatively connected to a navigational system, the process then proceeds to step 418, in which surgical access assembly 100 is navigated to area of interest 500. In one exemplary arrangement, distal tip 178 of obturator 104 is directed to a furthermost outer margin of area of interest 500. More specifically, referring to FIG. 12B, for example, surgical access assembly 100 is directed along a trajectory T that extends through area of interest 500 to a location 501 that may be positioned within the margins of area of interest 500 or even slightly beyond the margin.

Due to the tapered configuration and closed, radiused distal tip 174 of obturator 104, as well as the radiused distal tip 132 of outer sheath 102, as surgical access assembly 100 is inserted into the brain and navigated to area of interest 500, tissue is gently pushed to either side of surgical access assembly 100, so as to atraumatically dilate tissue, while minimizing trauma to the tissue. Further, because surgical access assembly 100 is operatively connected to navigation member 112, as surgical access assembly 100 is being inserted into the brain tissue, navigation member 112 may cooperate with an imaging modality to providing real-time information concerning fiber tact in trajectory T, thereby allowing the surgeon to minimize fiber tract compromise or damage during insertion of surgical access assembly 100. Once surgical access assembly 100 is positioned at area of interest 500, the process proceeds to step 420.

As step 420, navigation member 112 removed from or detached from surgical access assembly 100. The process then proceeds to step 422.

Figures 14A, 14B:
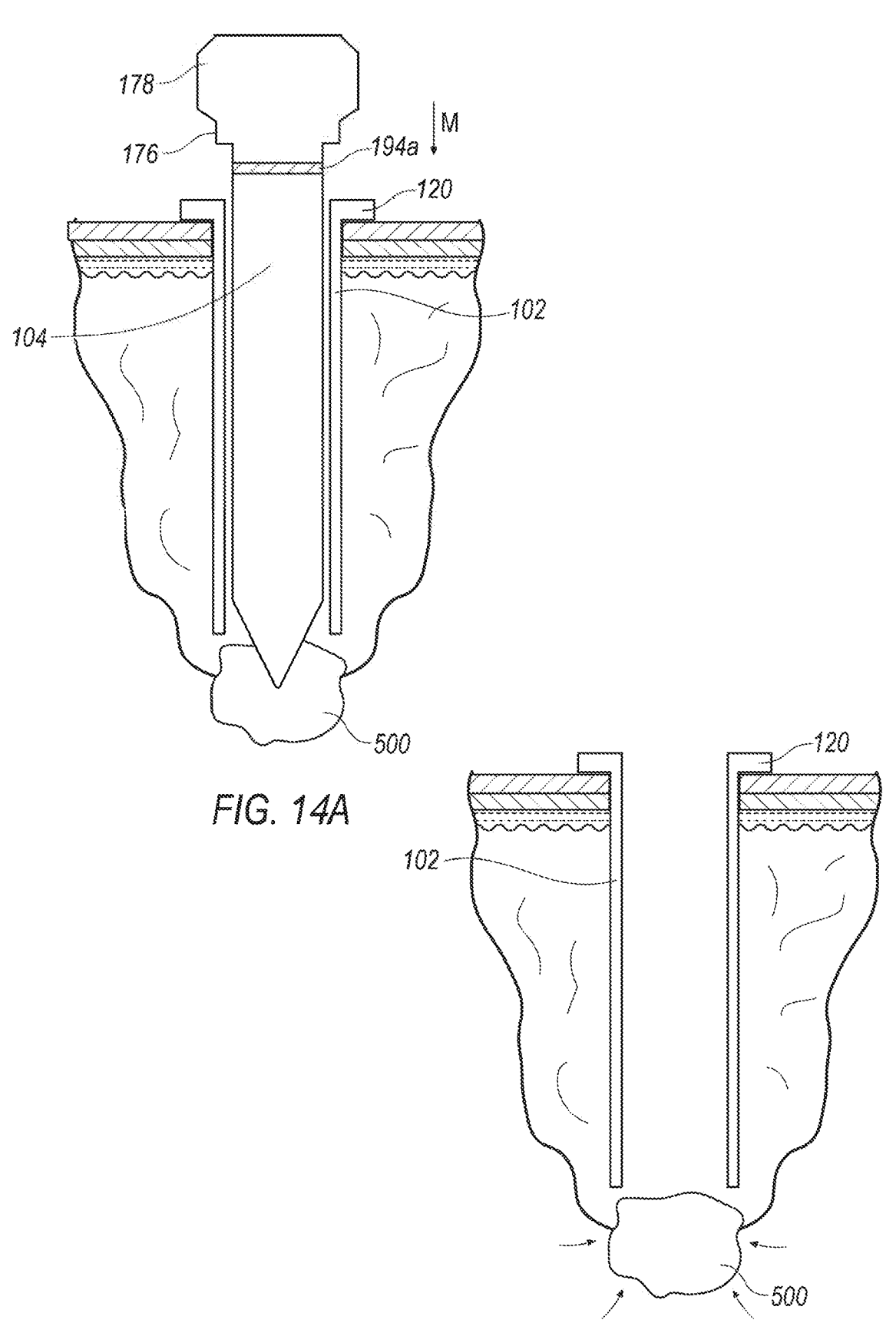
FIG. 14A is an elevational view of the surgical access system, while the obturator is being withdrawn from the outer sheath.
FIG. 14B is an elevational view of the surgical access system with the outer sheath in place within the brain.

Once navigation member 112 is removed, outer sheath 102 is then operatively positioned with respect to area of interest 500. More specifically, as shown in FIG. 14A, outer sheath 102 is decanted with respect to obturator 104 such that distal end 108 of outer sheath 102 is moved toward distal end 106 of obturator 104, as indicated by arrow M. This action is accomplished by grasping grip ring 120 with one hand while maintaining obturator 104 stationary, such, for example, grasping grip member 178 with another hand. Grip ring 120 may be gently rotated and/or swiveled with respect to a central axis of obturator 104 to enable outer sheath 102 to be moved distally with respect to obturator 104. First stop member 176 aids in gripping and manipulating outer sheath 102, in that a gap 423 (see FIG. 2) is created between end surface 158 and a distal end surface of grip member 178. Outer sheath 102 is decanted until grip ring 120 aligns with indicator 194A (see FIG. 7A). Indicator 194A is spaced from first stop member 176 a distance that generally corresponds to the length of distal tip portion 172 of obturator 104. Accordingly, when grip ring 120 is aligned with indicator 194A, distal end 108 of outer sheath 102 is aligned tip member 174 of obturator 104. Moreover, outer sheath 102 is positioned within area of interest 500. In one exemplary arrangement, the outer sheath 102 is decanted such that it is positioned with the grip ring 120 is spaced away from a surface S a distance that permits a holding member (as discussed in further detail below) to retain the outer sheath 102 in position. The process then proceeds to step 424.

In step 424, once outer sheath 102 is appropriately positioned, obturator 104 is then removed from outer sheath 102, as shown in FIG. 14B. More specifically, outer sheath 102 is maintained to be relatively stationary at area of interest 500, and obturator 104 is moved in a proximal direction until fully removed from outer sheath 102. This action results in outer sheath 102 forming a pathway to area of interest 500; a pathway that not only circumvents the need to cross the blood brain barrier for the delivery of therapy, but also provides direct access to the area of interest within the patient. Once outer sheath 102 is placed in its desired location, the process then proceeds to step 426.

In step 426, outer sheath 102 is then secured in place so as to prevent cranial pressure or general manipulation of instruments passing in and out of the sheath 102 from pushing or dislocating outer sheath 102 out of the brain tissue. In one exemplary arrangement, a securing member may be utilized with small openings 150 on grip ring 120 to temporarily secure outer sheath 102. However, the securing member may be secured so as to permit a limited degree of movement, as will be discussed below, so as to result in a floating system that permits selective repositioning. Suitable securing members include, but are not limited to, bridle sutures, flexible bands with retaining hooks, or even repositionable retractor arms. Additional alternative securing arrangements are disclosed below. Once outer sheath 102 is secured, the process then proceeds to step 428.

In step 428, debulking area of interest 500 may be conducted. Traditionally, a patient is given medication, such as, for example, Mannitol, before an intracranial operation to reduce intracranial pressure (ICP) of the brain prior to the surgery. Indeed, ICP is often experienced by patients due to the natural response of the craniotiomy and/or the present of an abnormality within the brain. The present inventors have found that it may be advantageous to omit or minimize the use of medication for reducing ICP. More specifically, by not reducing ICP, because the brain tends to occupy the available space within the skull, after obturator 104 is removed from outer sheath 102, the target tissue may have a tendency to flow into, and present itself into the open distal end 108 of outer sheath 102, due to the cranial pressure. Area of interest 500 may actually move into outer sheath 102 on its own, thereby assisting in the delivery and minimizing manipulation required of outer sheath 102 during the process.

It is contemplated that a wide range of surgical devices may be inserted into outer sheath 102 to remove tissue abnormalities. In one exemplary arrangement, it is contemplated that outer sheath 102 may have an inner diameter up to approximately 20 mm, to allow multiple instruments, such as graspers, dissectors, scissors, cautery and suction instruments to be inserted through outer sheath 102 to perform surgery.

Figure 15:
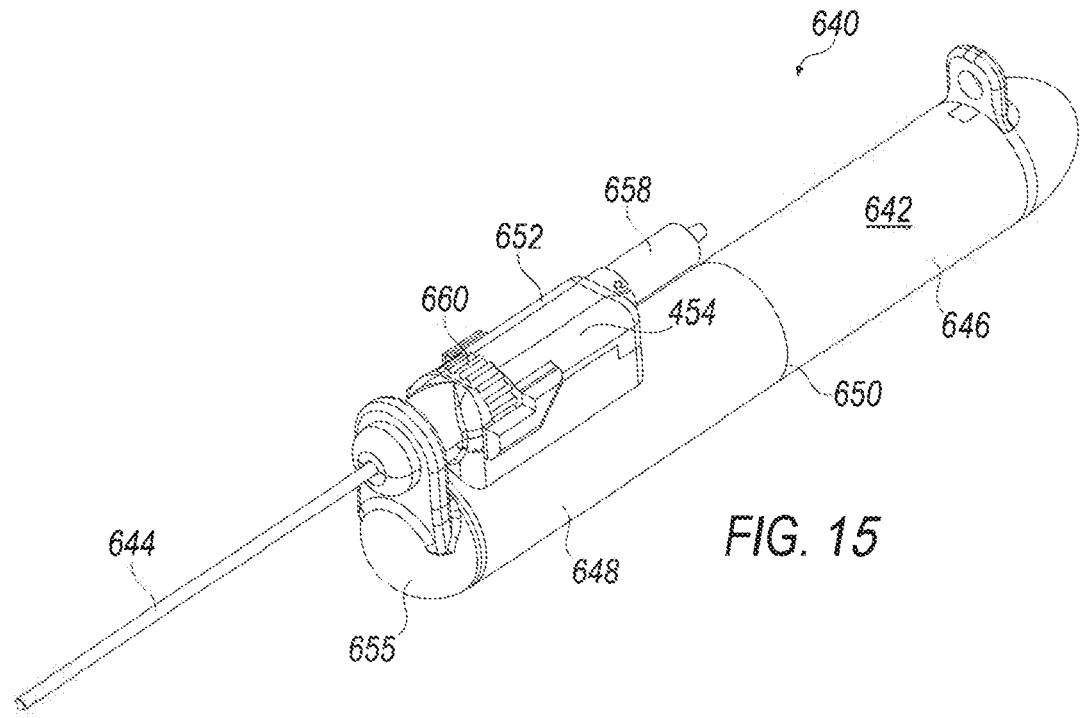
FIG. 15 is a perspective view of an exemplary surgical device used for cytoreduction.

One exemplary surgical device that may be used is the NICO MYRIAD® manufactured and distributed by Nico Corporation of Indianapolis, Indiana. Referring to FIG. 15, an exemplary surgical cutting device 640 is shown, such as that disclosed in co-pending, and co-owned with the assignee of the present application, U.S. patent application Ser. No. 12/389,447, the contents of which are incorporated by reference in its entirety. Surgical cutting device 640 includes a handpiece 642 and a cutting element that includes an outer cannula 644 and an inner cannula (not shown). In one exemplary configuration, handpiece 642 is configured with a generally cylindrical shape. Handpiece 642 may be sized and shaped to be grasped with a single hand. Handpiece 642 also includes a lower housing 650 comprising a proximal section 646 and a distal section 648. A front housing section 655 may be connected to a cam housing positioned in distal section 648. An upper housing 652 is also provided. The cutting element is mounted to upper housing 652 and may be fluidly connected to a tissue collector 658. In one exemplary arrangement, tissue collector 658 may be operatively connected directly to upper housing 652. Alternatively, tissue collector 658 may be remotely connected to the cutting element by appropriate tubing. A vacuum line (not shown) may be connected to a proximal end of tissue collector 658 to direct tissue into the cutting element, as well as to deliver severed tissue to tissue collector 658. A rotation dial 660 for selectively rotating the outer cannula 644 with respect to handpiece 642 is also mounted to upper housing 652, to provide controlled cutting action.

Use of surgical device 640 is advantageous in that space is limited to effectuate tissue debulking, such that use of traditional surgical scissors may be challenging, especially when other instruments are inserted into outer sheath 102 simultaneously. Moreover, fibrosity of a tumor may present challenges for the use traditional suction debulking devices. Traditional graspers operate by tearing tissue of interest. However, the tearing action may become problematic if vessels or fascicles are too close to the tissue being torn in that such vessels or fascicles may also be torn.

In step 428, as area of interest 500 is cytoreductively debulked, it may become necessary to reposition or move outer sheath 102. If repositioning is necessary, the process moves to step 432. To that end, in one exemplary arrangement, one or more manipulation members may be provided. Examples of manipulation members and their operation are described in co-pending U.S. patent application Ser. No. 13/444,722 the contents of which are incorporated by reference in its entirety. After outer sheath 102 has been repositioned, or if repositioning of outer sheath 102 is not necessary, the process moves to step 434, and cytoreduction of area of interest 500 continues.

Figures 16A, 16B, 16C, 16D:
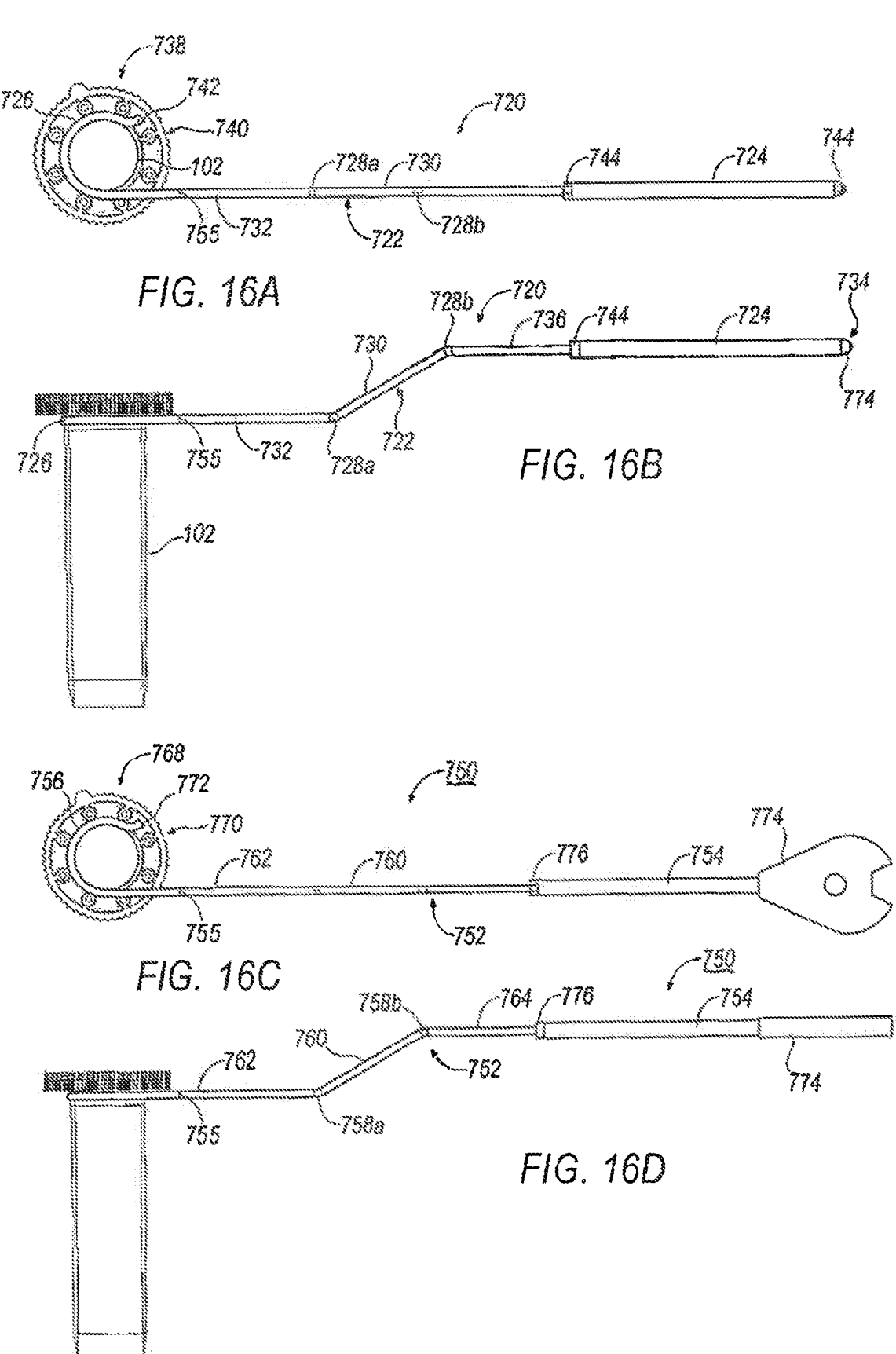
FIG. 16A is top view of the outer sheath operatively connected to a first exemplary arrangement of a holding arrangement therefore.
FIG. 16B is an elevational view of the outer sheath and holding arrangement of FIG. 16A.
FIG. 16C is a top view of the outer sheath operatively connected to a second exemplary arrangement of a holding arrangement therefore.
FIG. 16D is an elevational view of the outer sheath and holding arrangement of FIG. 16C.

Referring to FIGS. 16A-16D, other alternative arrangements for holding outer sheath 102 during a procedure are shown. More specifically, FIGS. 16A-16B illustrate a holding arrangement 720 that may be used with a Greenberg retractor assembly. Holding arrangement 720 comprises body portion 722, an engagement barrel 724, and a retaining member 726.

Body portion 722 may be configured as a relatively thin shaft. In one exemplary arrangement, body portion 722 includes at least two bend points 728a and 728b that are separated by a section of shaft 730. Bend point 728a is positioned proximal of a distal end of body portion 722, defining a retaining section 732. Bend point 728b is positioned proximal of shaft section 730. Bend point 728b and a proximal end 734 cooperate to define a proximal shaft section 736. Bend points 728a and 728b serve to axially space retaining section 732 from proximal section 734. In one arrangement, as shown in FIG. 16B, shaft section 730 is disposed at an approximately 45° angle. In another exemplary arrangement (not shown), shaft section 730 may be oriented at an approximately 90° angle. It is also contemplated that shaft section 730 may be deposed at other angles. In some exemplary arrangements, bend points 728a, 728b may be eliminated such that retaining section 732 and proximal section 736 are arranged along a common axis. Retaining section 732, shaft section 730 and proximal section 736 may be integrally formed together, or constructed as separate elements that are connected together.

Retaining section 732 terminates at its distal end 738 in retaining member 726. As best seen in FIG. 16A, retaining member 726 is configured as a shepherd's hook that is configured to curve back toward retaining section 732, but defining a gap 740 between an end 742 of retaining member 726 and retaining section 732. In one exemplary arrangement the end 742 is bent slightly backward in a direction away from gap 740. Retaining member 726 may be integrally formed with retaining section 732, or formed as a separate component that connects with retaining section 732. Retaining member 726 is configured similar to a spring clip such that retaining member 726 snaps partially around outer sheath 102. In one exemplary arrangement, the retaining member 726 is configured to extend around greater than 50% of the outer circumference of the outer sheath 102 to positively retain and support the outer sheath 102.

Mounted on proximal section 736 is engagement barrel 724. Engagement barrel 724 is configured for selectively rotation about proximal section 736. In one exemplary arrangement, on either end of engagement barrel 724, stop members/ferrules 744 are disposed. The stop members/ferrule 744 are fixedly connected to the proximal section 736 of the body portion 722. Moreover, the proximal section 736 of body portion 722 extends through the stop members/ferrules 744 and the engagement barrel 724. In operation, engagement barrel 724 is positioned within Greenberg adapter and clamped thereto. Stop members 744 serve to prevent gross lateral movement of the holding arrangement during operation. However, due to the configuration of engagement barrel 724 and placement of stop members 744, engagement barrel 724 is permitted to be clamped anywhere along the engagement barrel, thereby providing flexibility in the positioning of holding arrangement. Moreover, because engagement barrel 724 is configured to selectively rotate about proximal section 736, outer sheath 102 may be selectively pivoted along the Y direction to a desired position. Further, because retaining member 726 is configured as a shepherd's hook with the gap 740, outer sheath 102 may be pivoted in the X direction. Thus holding arrangement 720 allows for selective positioning of outer sheath 102, even after clamped to the adapter.

An alternative holding arrangement 750 is shown in FIGS. 16C-16D. Holding arrangement 750 is configured to be used with a Sugita adapter (not shown). Holding arrangement 750 is similar to holding arrangement 720 comprises body portion 752, an engagement barrel 754, and a retaining member 756.

Body portion 752 may be configured as a relatively thin shaft and may include one or more bend points 758a-758b. Like holding arrangement 720, bend points 758a, 758b serve to axially offset a retaining section 762 from a proximal section 764. A shaft section 760 is positioned between bend points 758a, 758b.

Retaining section 762 terminates at its distal end 768 in retaining member 756. As best seen in FIG. 19E, retaining member 756 is configured as a shepherd's hook that is configured to curve back toward retaining section 762, but defining a gap 770 between an end 772 of retaining member 756 and retaining section 762. Retaining member 756 may be integrally formed with retaining section 762, or formed as a separate component that connects with retaining section 762. Retaining member 756 is configured similar to a spring clip such that retaining member 756 snaps partially around outer sheath 102.

Mounted on proximal section 764 is engagement barrel 754. Engagement barrel 754 is configured for selectively rotation about proximal section 764. A mounting member 774 is fixedly secured to engagement barrel 754. Mounting member 774 is configured to be received within a Sugita clamp mechanism. In one exemplary arrangement, on a distal end of engagement barrel 754, a stop member 776 is disposed. In operation, engagement barrel 754 is positioned within the Sugita adapter and clamped thereto. Stop member 776 serves to prevent engagement barrel 754 from being unintentionally extracted from the Sugita adapter. However, due to the configuration of engagement barrel 754 and placement of the stop member 776, engagement barrel 754 is permitted to move a predetermined amount in a linear fashion. Moreover, because engagement barrel 754 is configured to selectively rotate about proximal section 764, outer sheath 102 may be selectively pivoted along the Y direction to a desired position. Further, because retaining member 756 is configured as a shepherd's hook with the gap 770, outer sheath 102 may be pivoted in the X direction. Thus holding arrangement 750 allows for selective positioning of outer sheath 102.

Figure 35A:
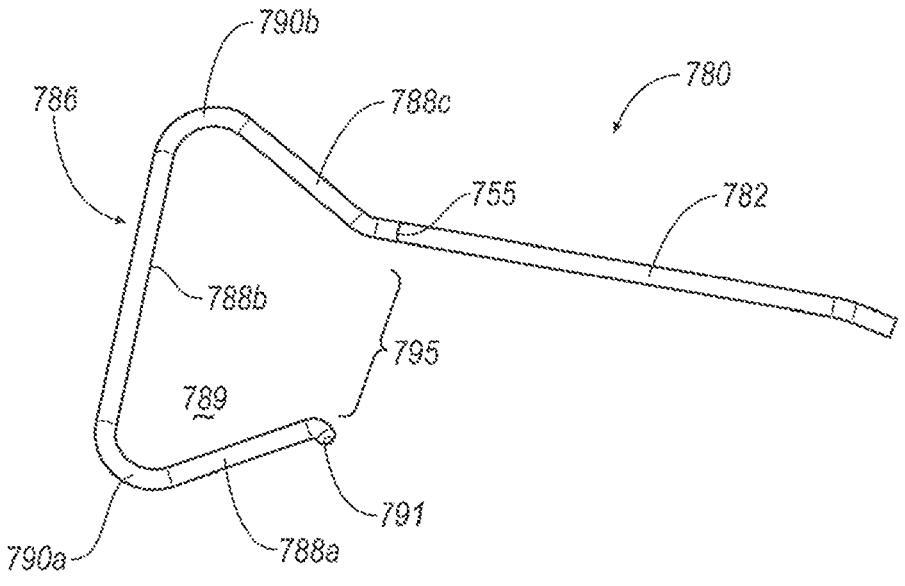
FIG. 35A is a perspective view of an alternative shape of a retaining member that may be used with either of the holding arrangements shown in FIGS. 16A-16D.
Figure 35B:
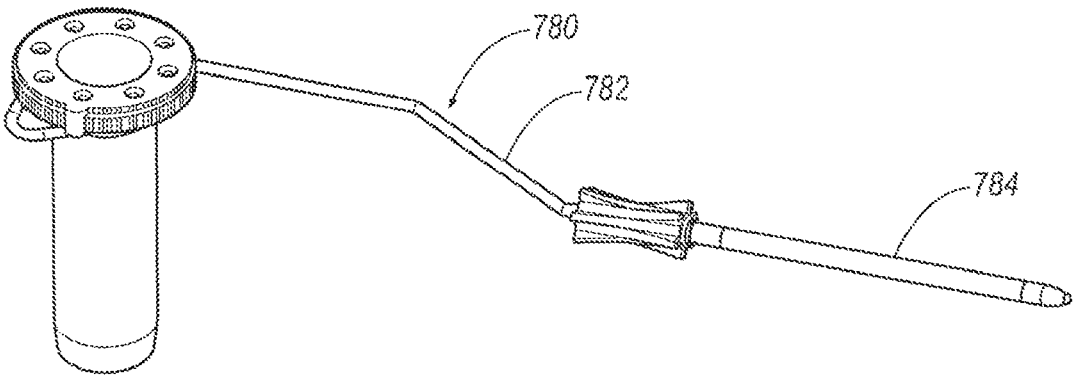
FIG. 35B is a perspective view of the rotational brake of FIG. 20 engaged on the holding arrangement of FIG. 35A.
Figure 36:
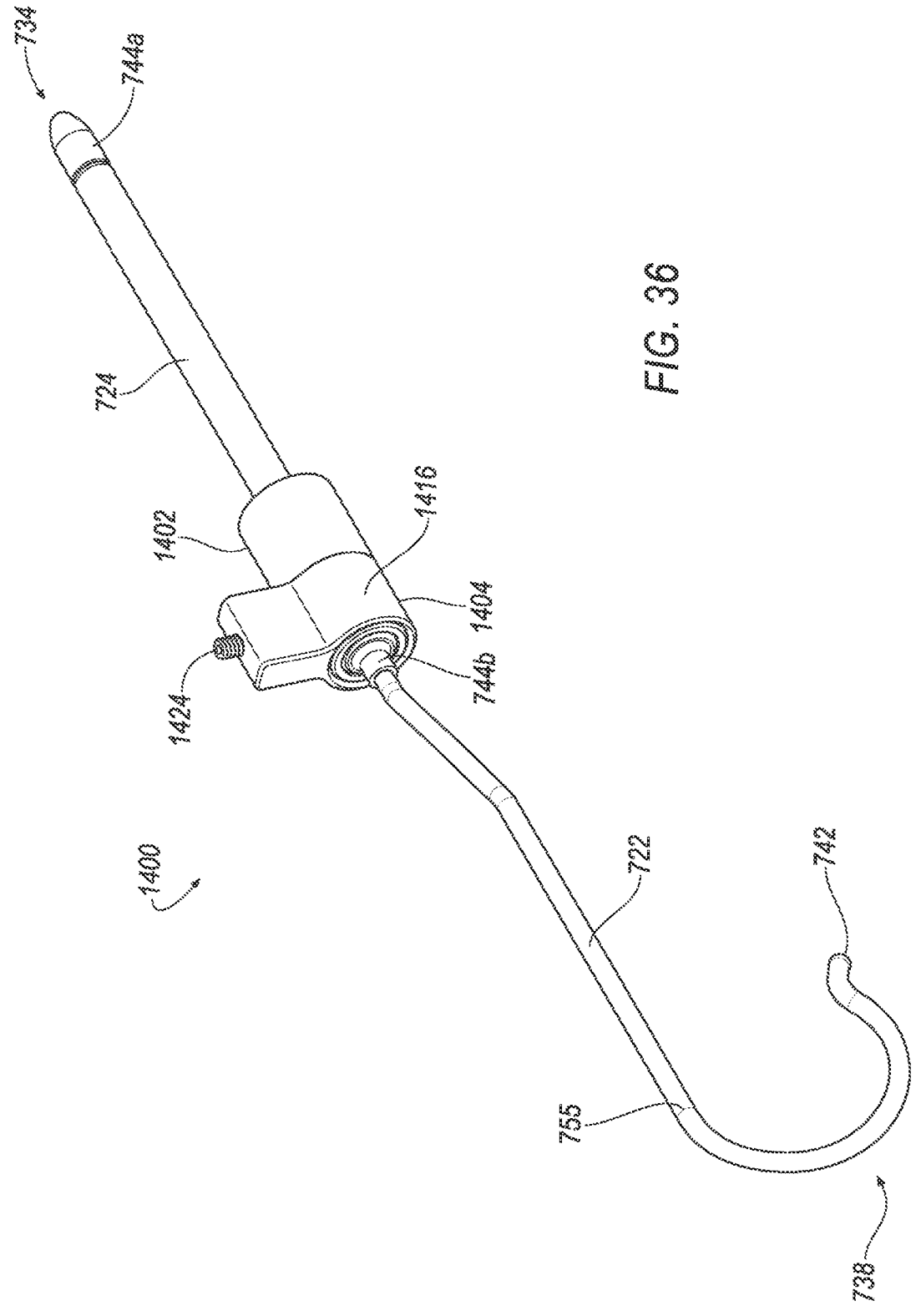
Figure 37:
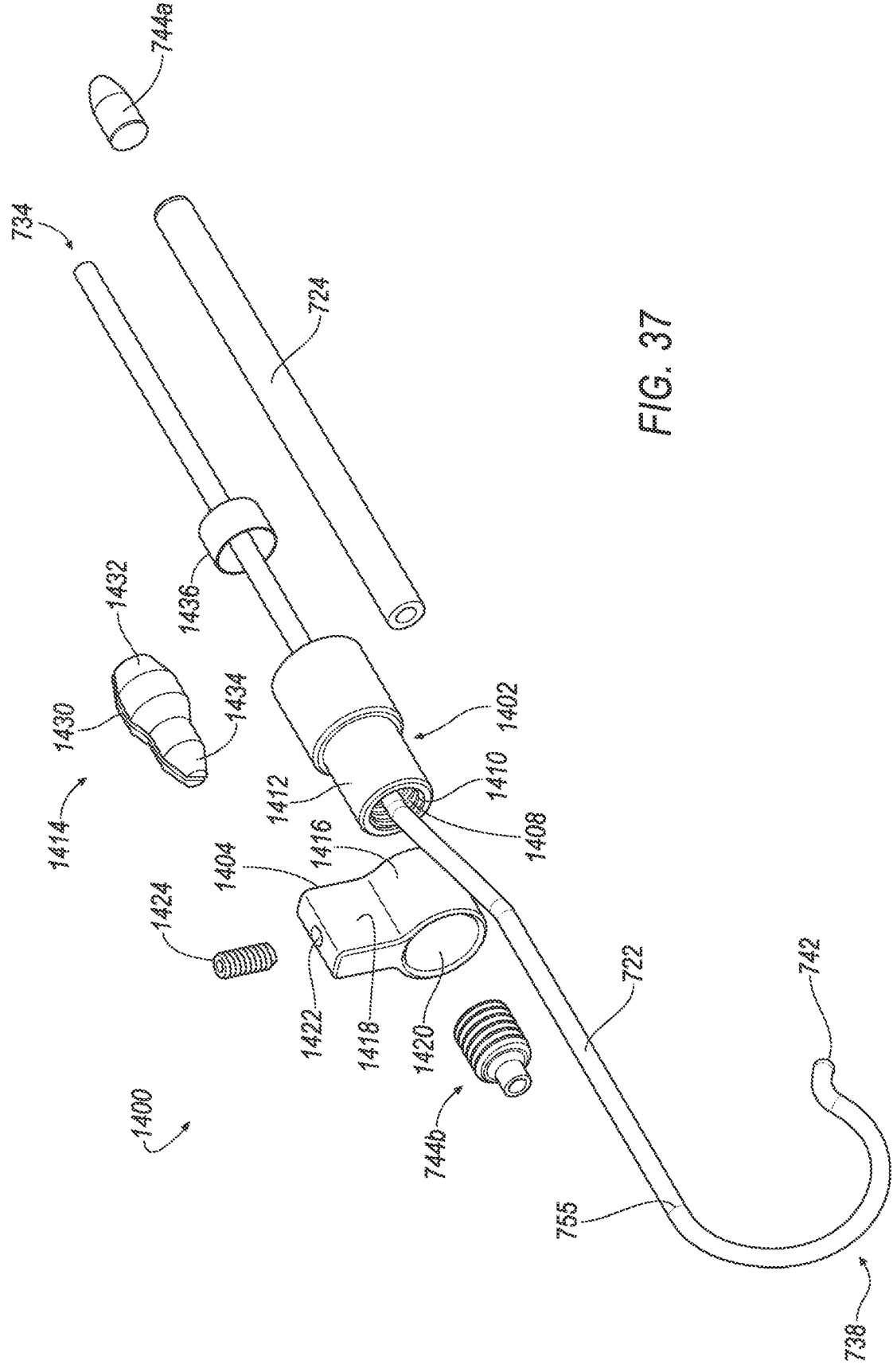
Figure 38:
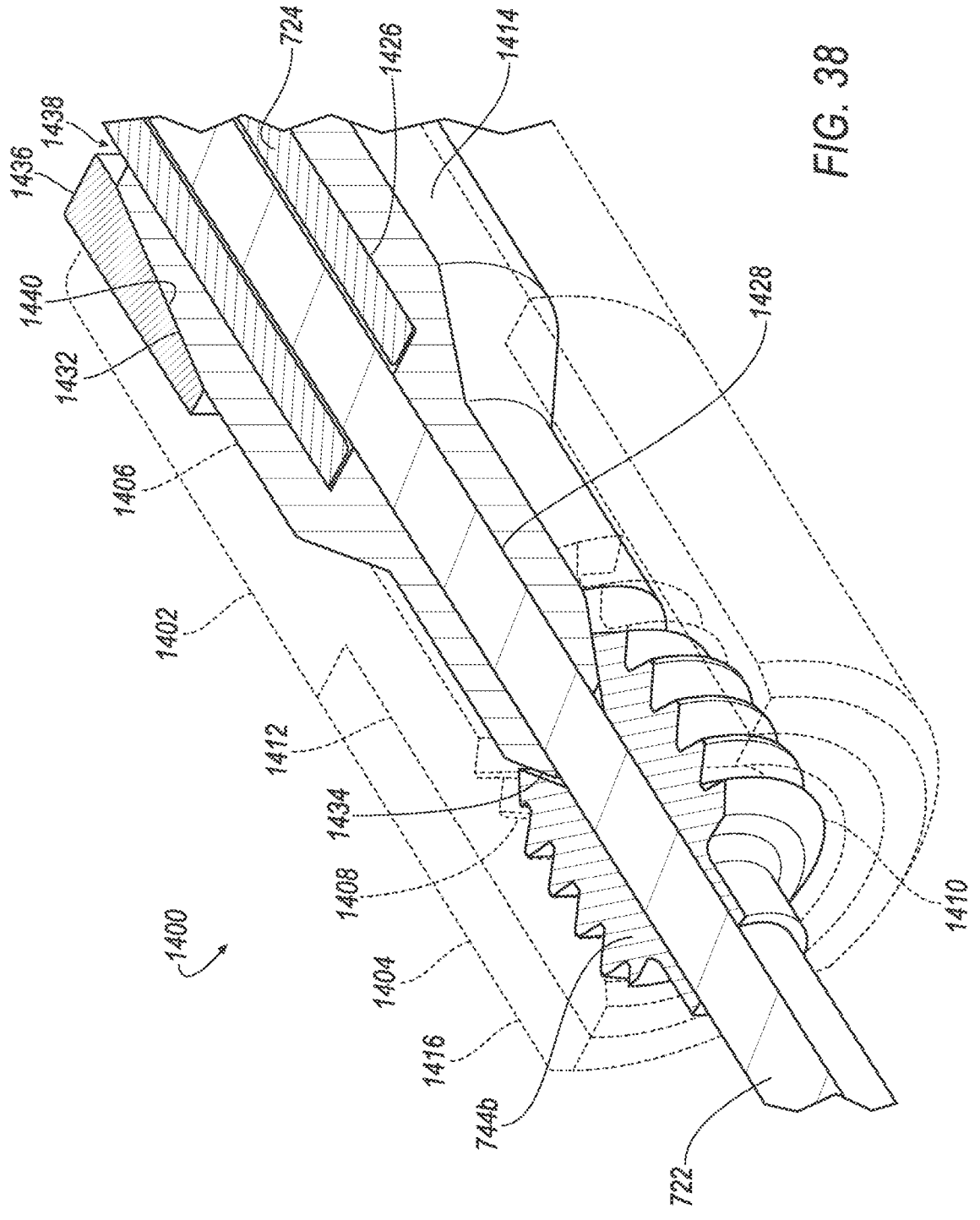
Figures 39A, 39B:
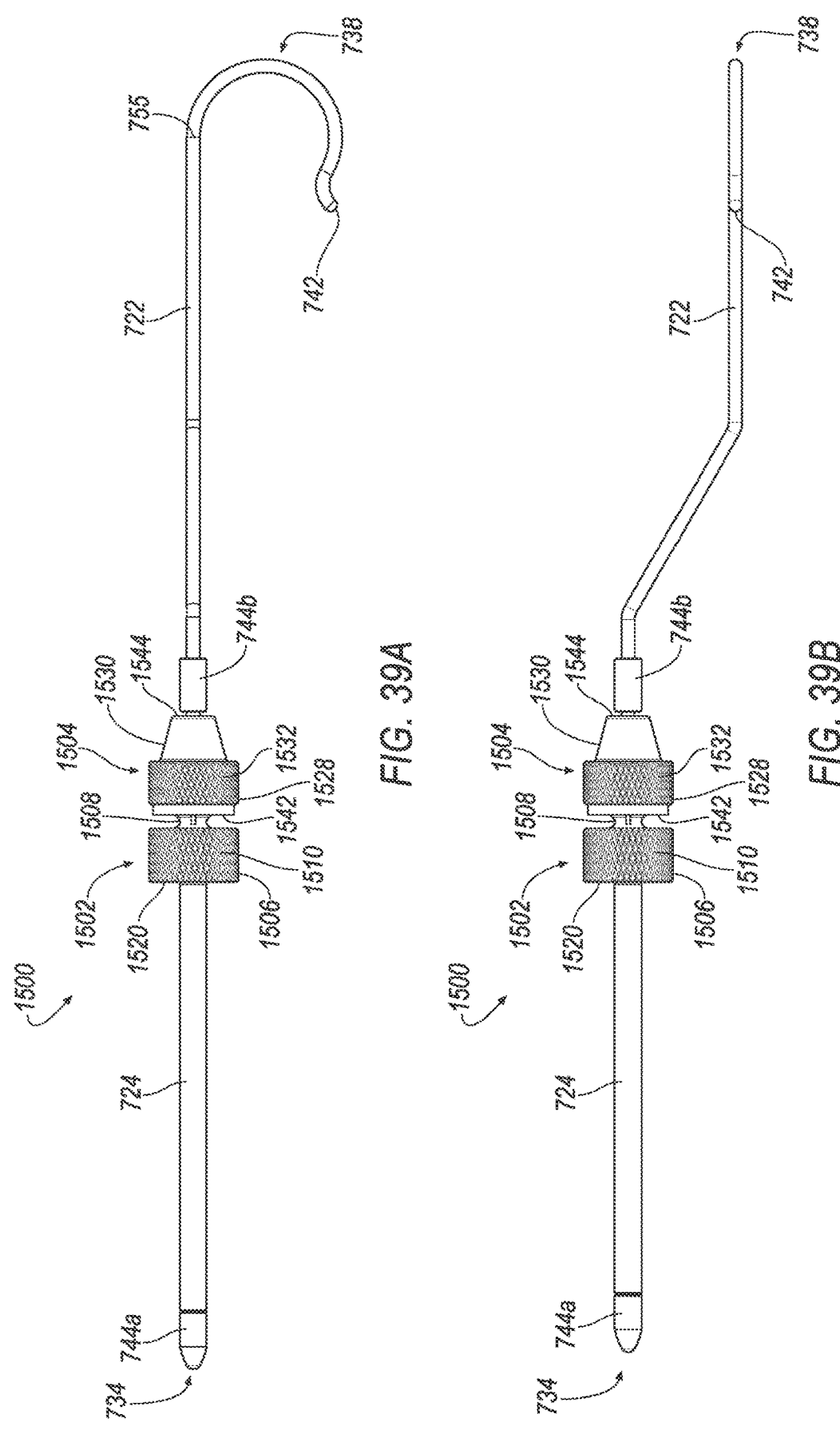
Figure 40:
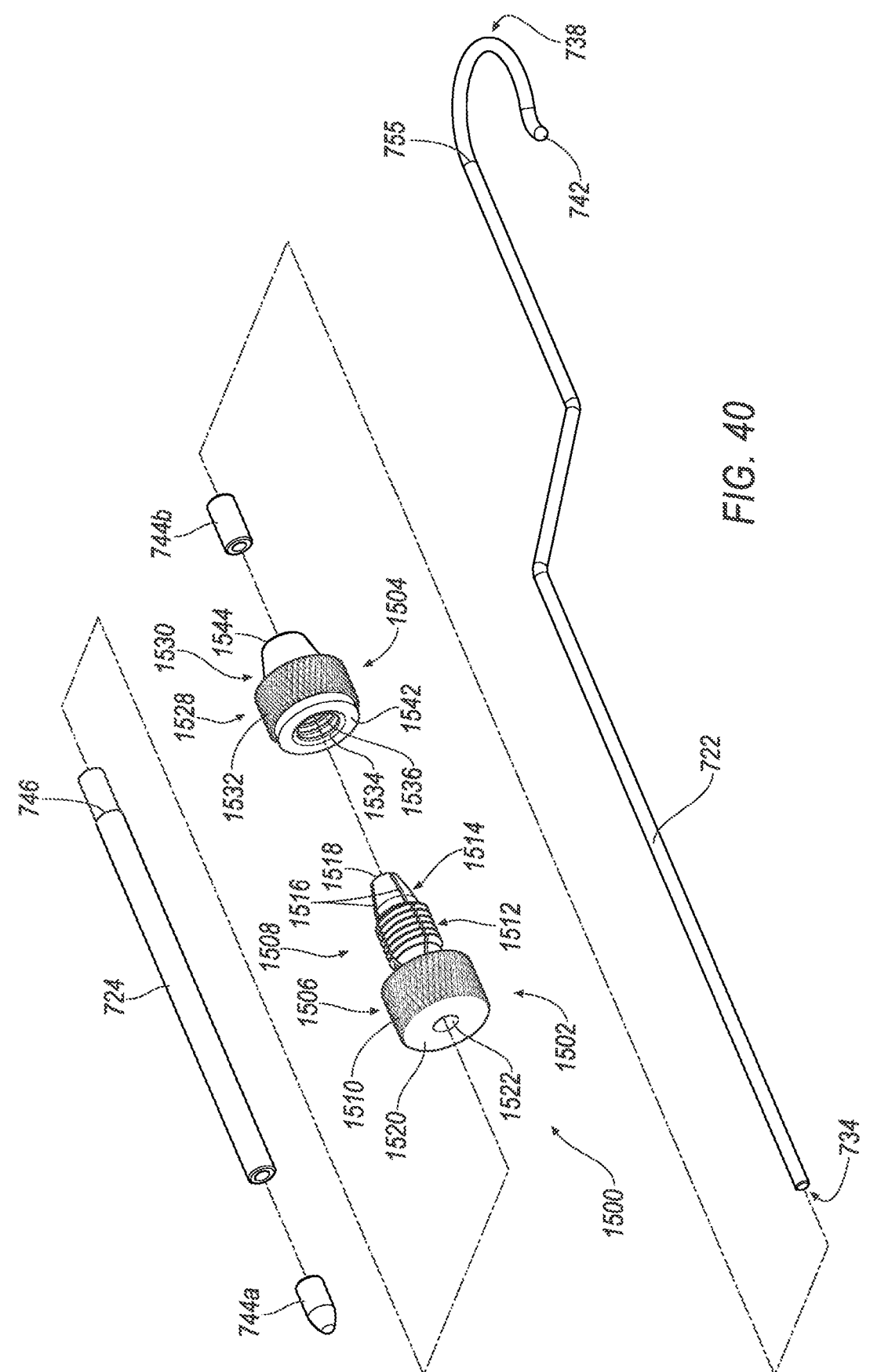
Figure 41:
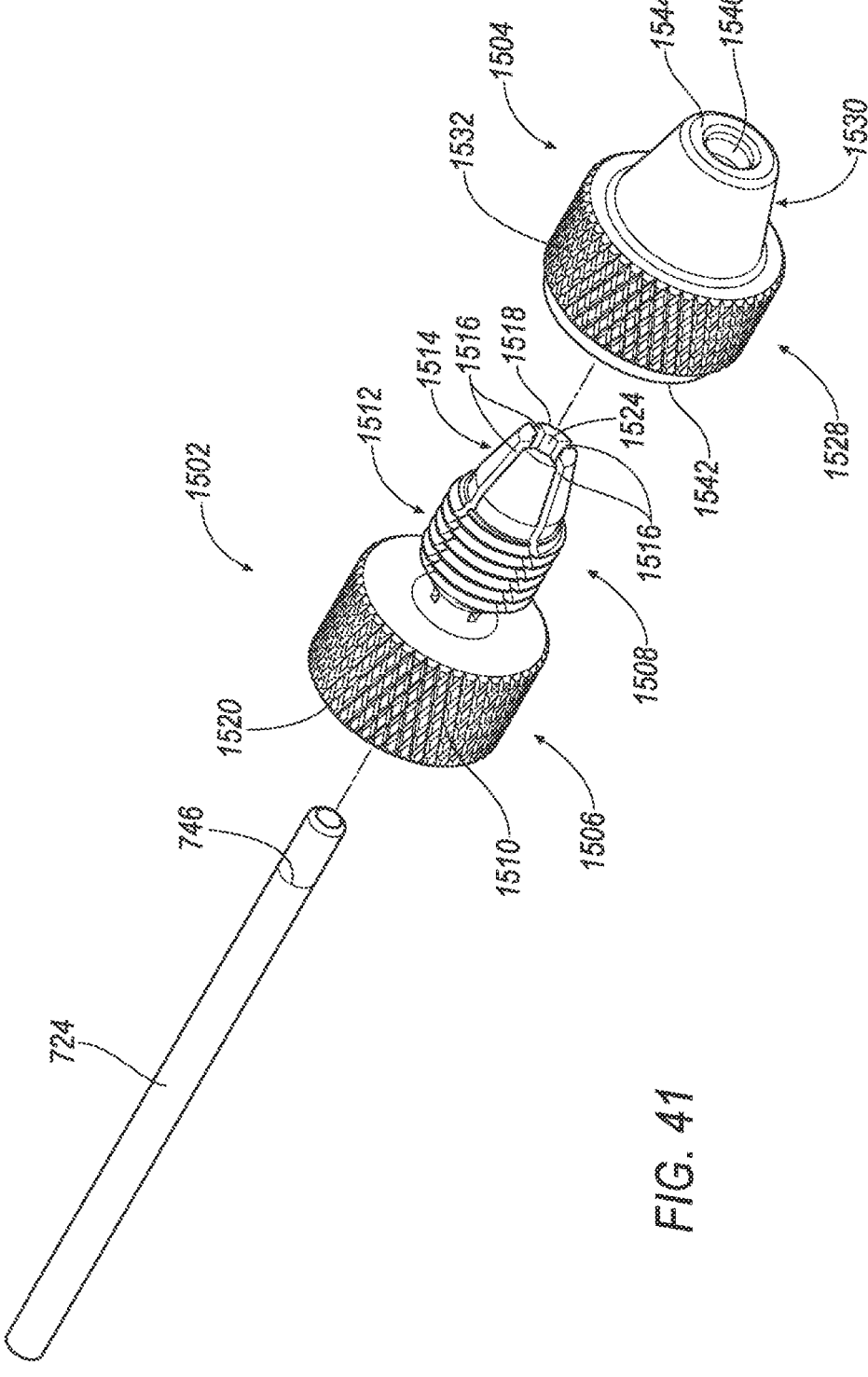
Figure 42:
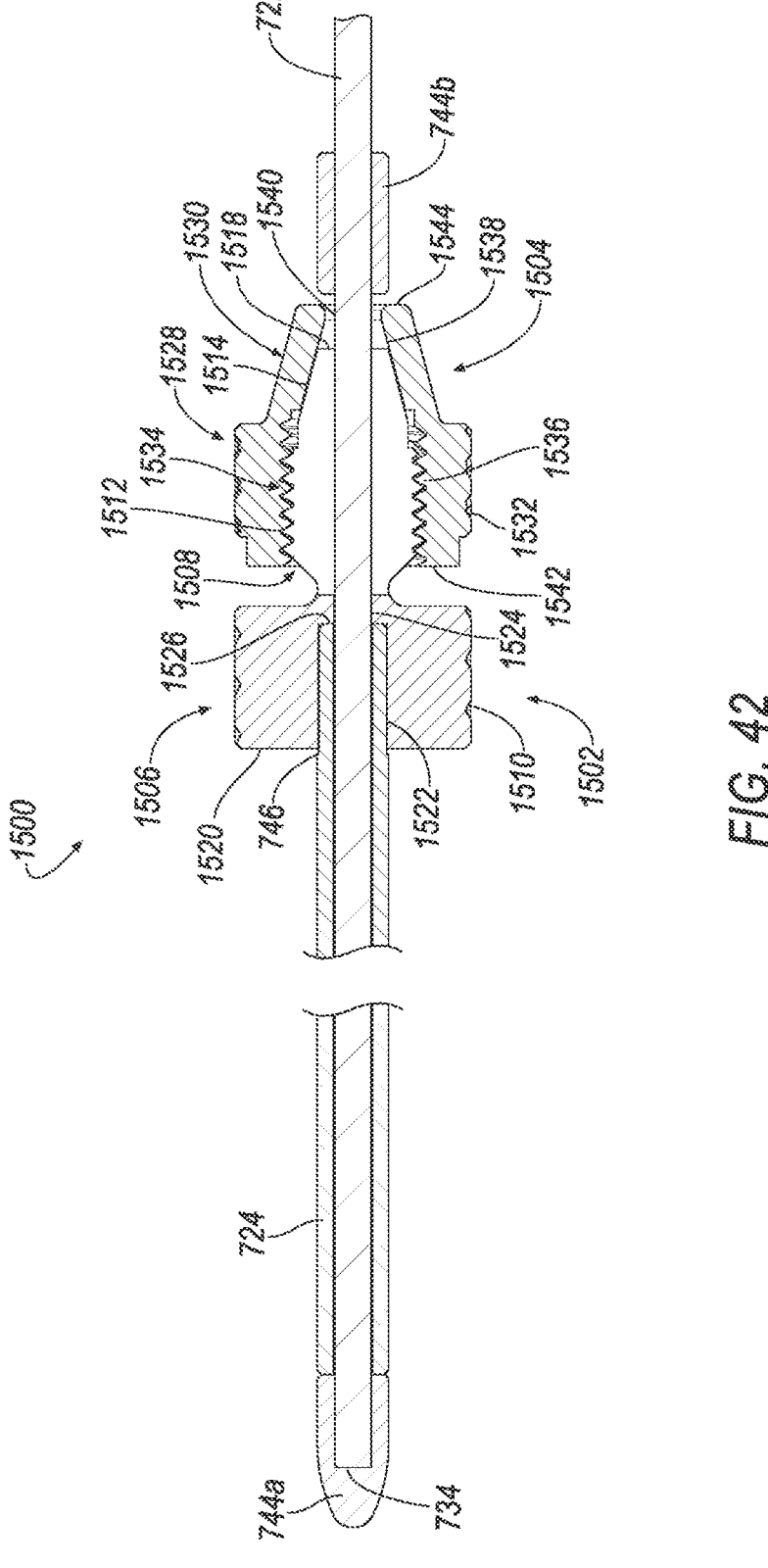
Figure 43A:
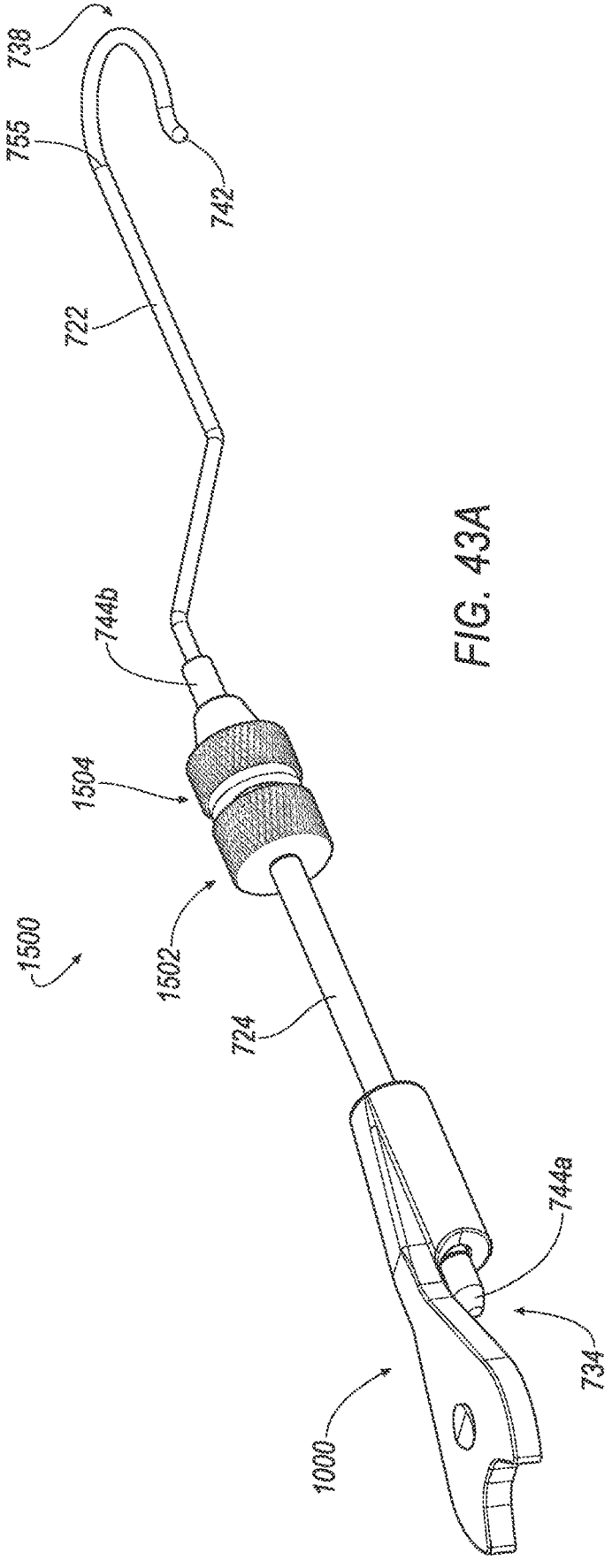
Figure 43B:
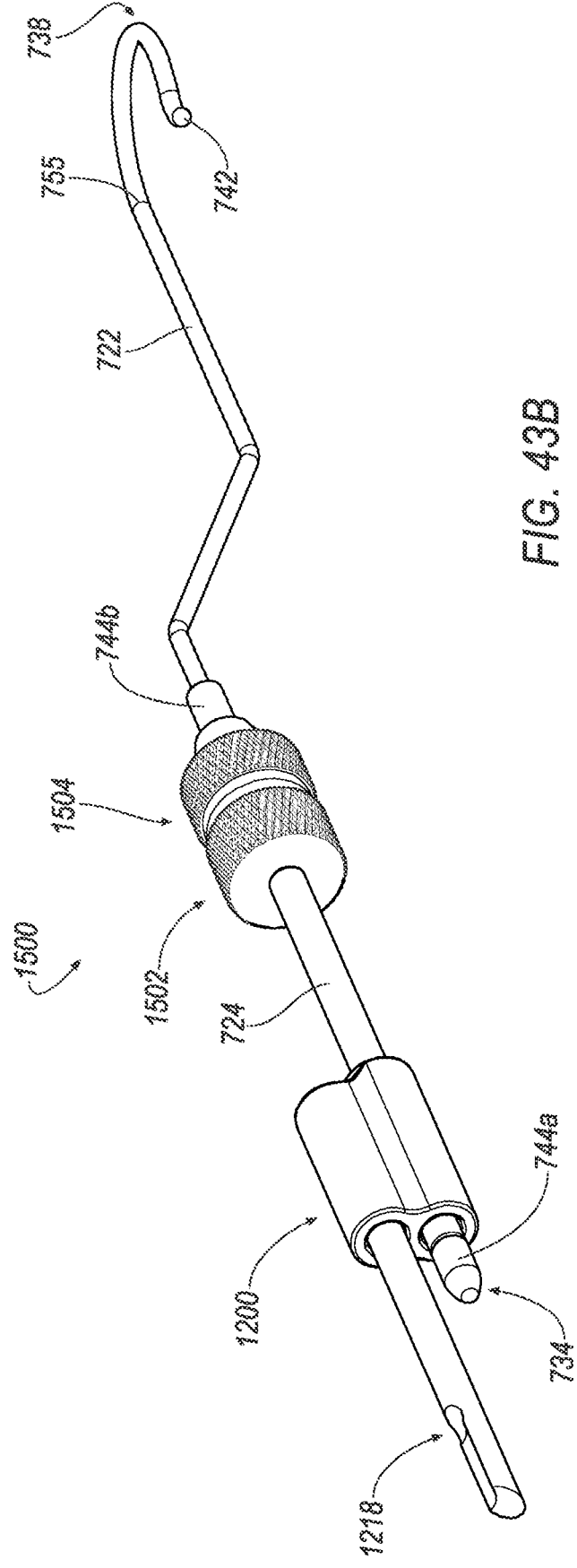

Referring to FIG. 35A, a partial view of an alternative holding arrangement 780 is shown. Holding arrangement 780 is similar to holding arrangements 720 and 750 in that all include a body portion 722/752 that is connected to a retaining member 786. As shown in FIG. 35B, the body portion 782 is connected to an engagement barrel 785. The retaining member 786 has a generally triangular shape defined by first, second and third segments 788a, 788b, and 788c. An outwardly extending lip 791 is positioned adjacent the first segment 788a. Curved sections 790a and 790b join first and second and second and third segments together and define a triangular shaped cavity 789. An opening 795 provides access to the cavity 789.

In operation, the outer sheath 102 is directed into the cavity 789 through the opening 795. Due the three contact points created by the curved section 790a, 790b and the lip 791, the holding arrangement 780 is able to accommodate outer sheaths 102 of varying diameters with a single profile.

Once a desired position of holding arrangements 720 and/or 750 has been achieved, it may be beneficial to "lock" the holding arrangement 720 and/or 750 against rotation. More specifically, it may be beneficial to provide a rotation brake to selectively lock the engagement barrel 724/754 against rotation.

Figure 17:
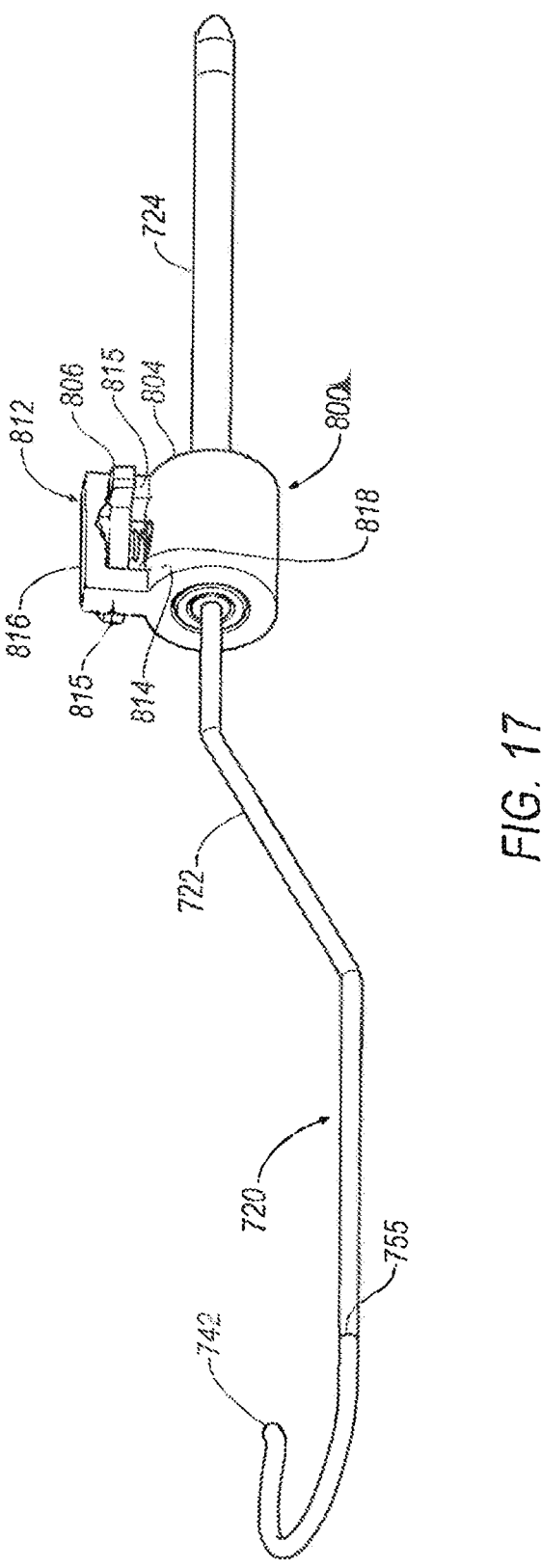
FIG. 17 is a perspective view of the holding arrangement of FIG. 16A with a rotational brake thereon.

Referring to FIGS. 17-19, a first exemplary arrangement of a rotation brake 800 is illustrated. While rotation brake 800 is illustrated as being used with holding arrangement 720, it is understood that rotation brake 800 may also be used with holding arrangement 750, as well.

Rotation brake 800 comprises a sleeve element 802 that is disposed within a brake housing 804 and a selectively turnable brake lever 806. The sleeve element 802 is defined by a channel 808 that is sized to receive stop members/ferrules 744 therein. The sleeve element 802 is further defined by a length that is longer than the stop member/ferrule 744. When assembled, the sleeve element 802 is positioned over stop member/ferrule 744a such that a portion of the sleeve element 802 overlies a portion of the engagement barrel 724. The portion of the sleeve element 802 that is positioned over stop member/ferrule 744a is fixedly secure to the stop member/ferrule 744a such that the sleeve element 802 moves with the body portion 722. However, the sleeve element 802 is not fixedly connected to the engagement barrel 724.

The sleeve element 802 is disposed within a mounting channel 810 disposed within the brake housing 804. In one embodiment, the sleeve element 802 is fixed to the stop member/ferrule 744a. Brake housing 804 is fixedly connected to the engagement barrel 724. In another exemplary arrangement, the sleeve element 802 is fixedly mounted within the channel 810. In one particular arrangement, the mounting channel 810 may be configured to receive the sleeve element 802 in a snap-fit arrangement. Other manners of fixing the sleeve element 802 within the mounting channel 810 of the brake housing 804 are also contemplated. A brake guard 812 extends outwardly from an outer surface 814 of the brake housing 804. The brake guard 812 is defined by a pair of outwardly extending arms 815 that are joined together by a leg 816. The leg 816 and arms 815 cooperate to define a clearance 818 for the brake lever 806.

Figure 18A:
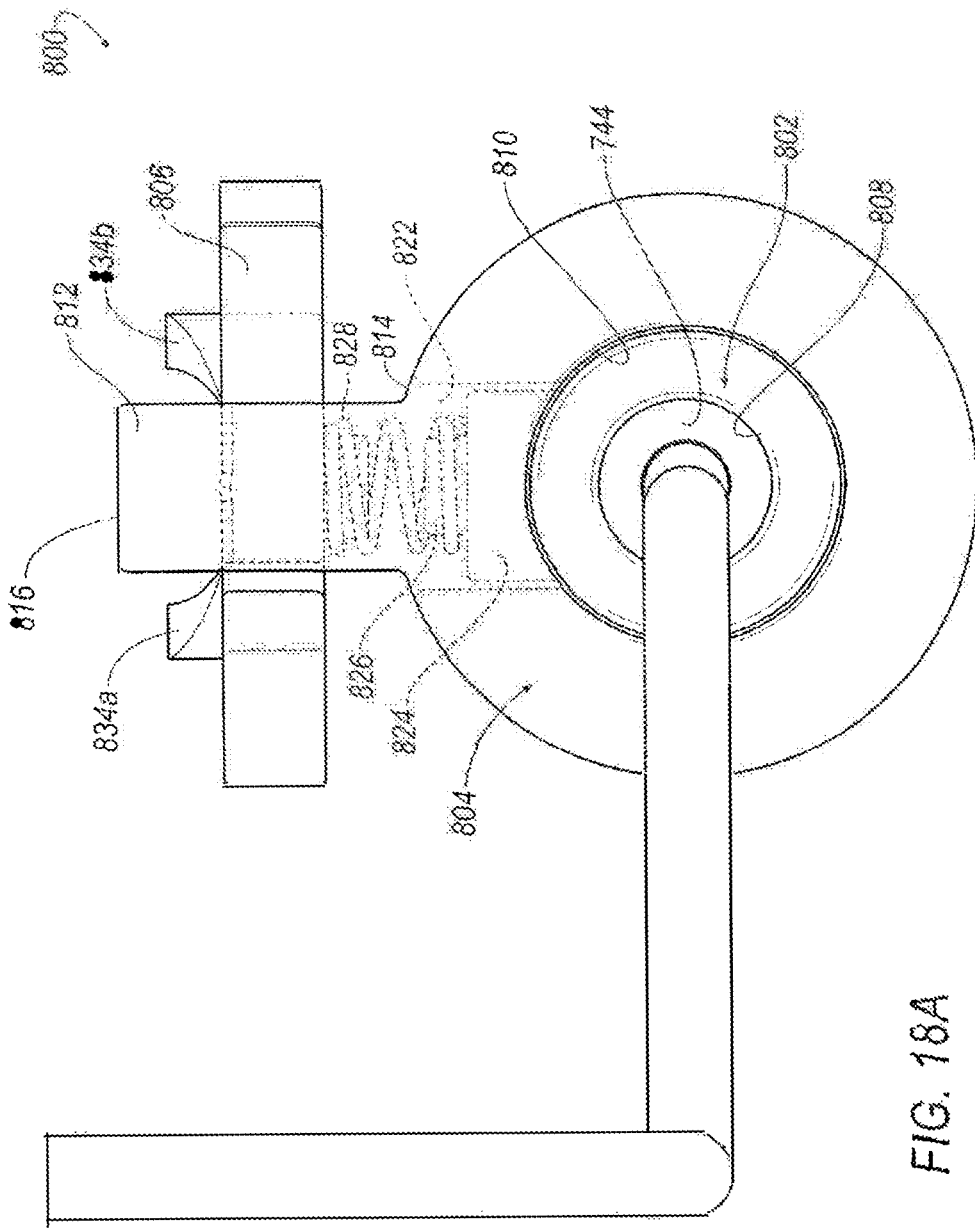
FIG. 18A is a side partial cross-sectional end view of the rotational brake of FIG. 17 in an unlocked position.
Figure 18B:
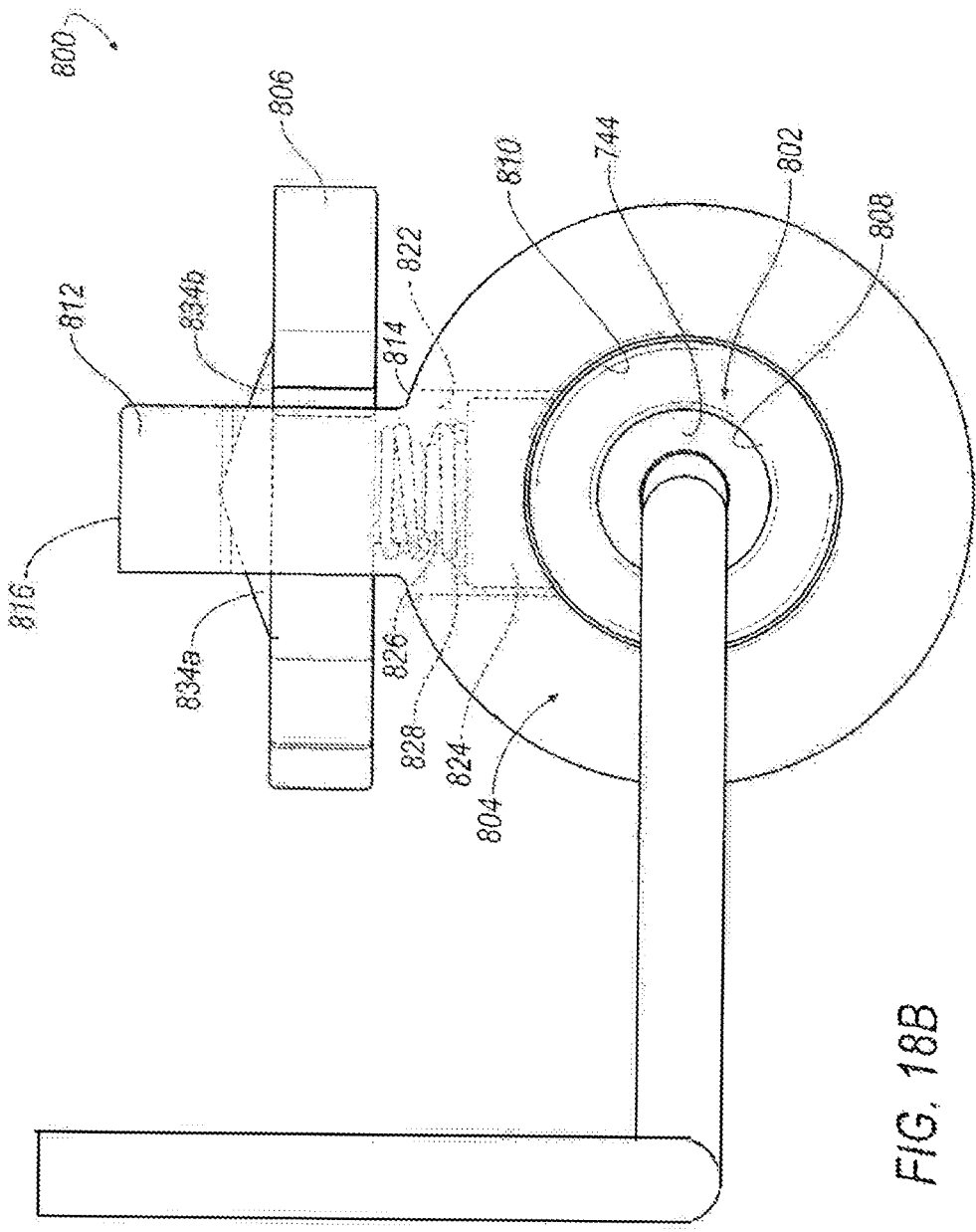
FIG. 18B is a side partial cross-sectional end view of the rotational brake of FIG. 17 in a locked position.

As best seen in FIGS. 18A and 18B, diametrically opposed to the leg 816 is an opening 820 that extends through the sidewall of the brake housing 804. The opening 820 is in communication with a stopper channel 822. The stopper channel 822 opens into the mounting channel 810. A stopper 824 is positioned within the stopper channel 822 and includes a spring mount 826. One end of a biasing member 828 is positioned on the spring mount 826.

The opposite end of the biasing member 828 is connected to the brake lever 806. In one exemplary arrangement, the brake lever 806 has a main body section 830 and opposing finger tabs 832 extending outwardly therefrom. Disposed on a top surface of the main body section 830 are sloped members 834a, 834b. A groove 836 is disposed between the sloped members 834a, 834b.

Figures 19A, 19B:
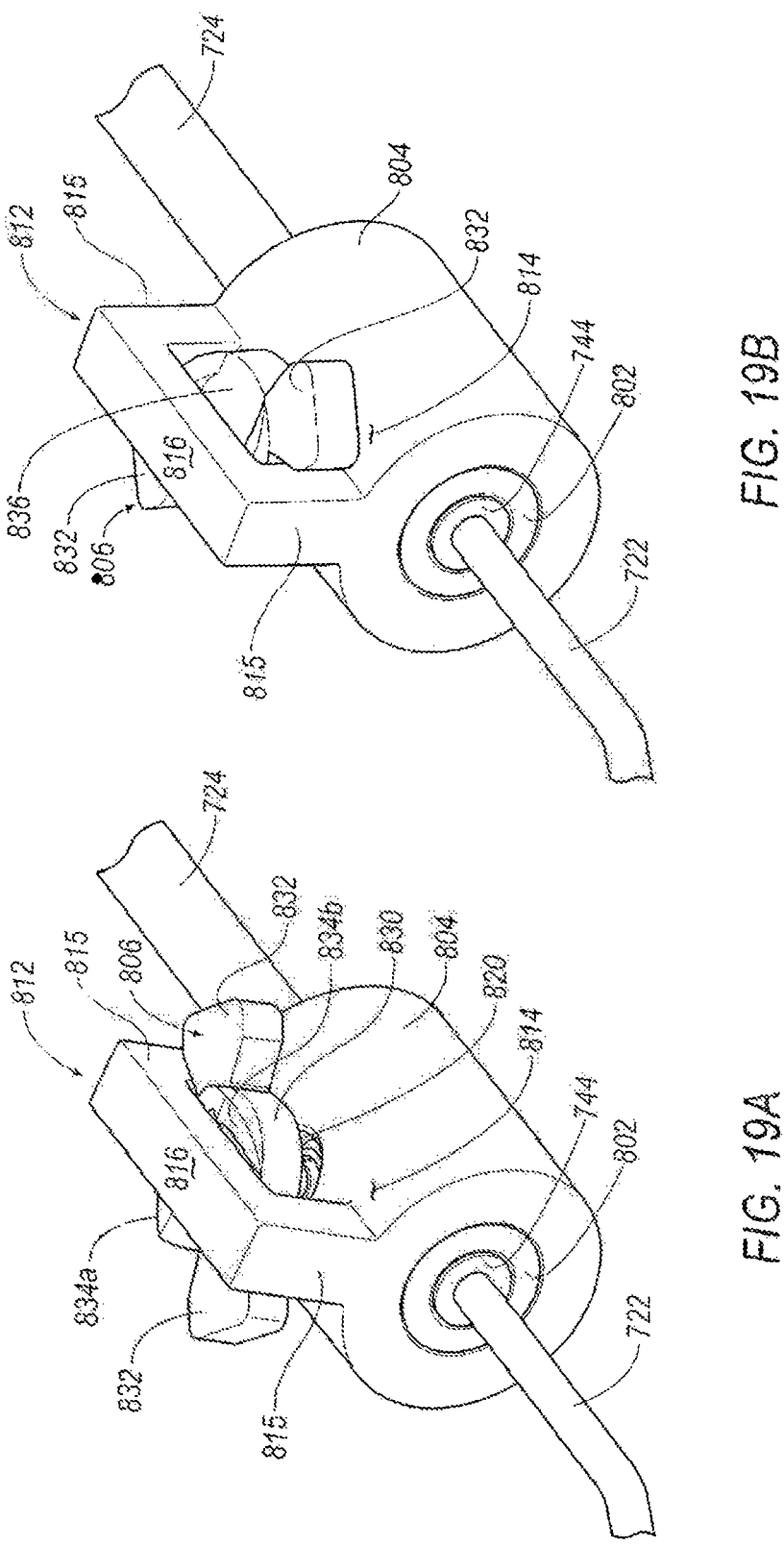
FIG. 19A is a top perspective view of the rotational brake of FIG. 17 in an unlocked position.
FIG. 19B is a top perspective view of the rotational bake of FIG. 17 in a locked position.

In operation, when the groove 836 is positioned to substantially align with the leg 816 the biasing member 828 is in an unlocked position (shown in FIGS. 18A and 19A). In the unlocked position, the biasing member 828 is in its extended position and the stopper 824 is not frictionally engaged against the sleeve element 802. To transition the rotation brake 800 into a locked position (shown in FIGS. 18B and 19B), the finger tabs 832 are rotated causing the sloped members 834a, 834b to engage against the leg 816. As the finger tabs 832 are rotated, the sloped members 834a, 834b cause the brake lever 806 to move downwardly in the clearance 818, against the biasing member 828 so as to push the stopper into frictional engagement with the sleeve element 802, which is engaged with the engagement barrel 724. In this position, the engagement barrel 724 is prevented from rotating.

Figure 20:
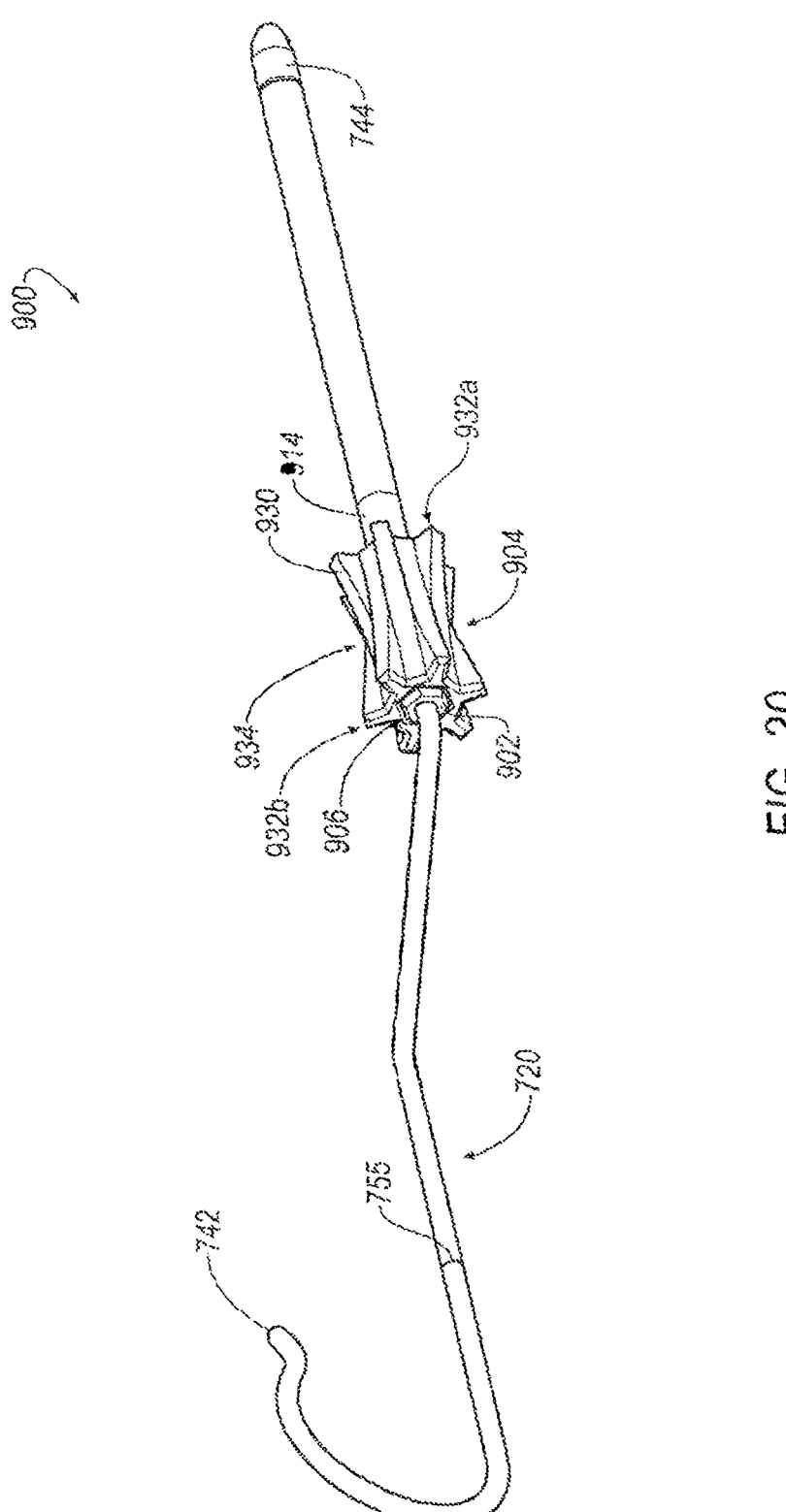
FIG. 20 is a perspective view of the holding arrangement of FIG. 16A with an alternative rotational brake thereon.

An alternative rotation brake 900 is illustrated in FIGS. 20-21. While rotation brake 900 is illustrated as being used with holding arrangement 720, it is understood that rotation brake 900 may also be used with holding arrangement 750, as well.

Figure 21A:
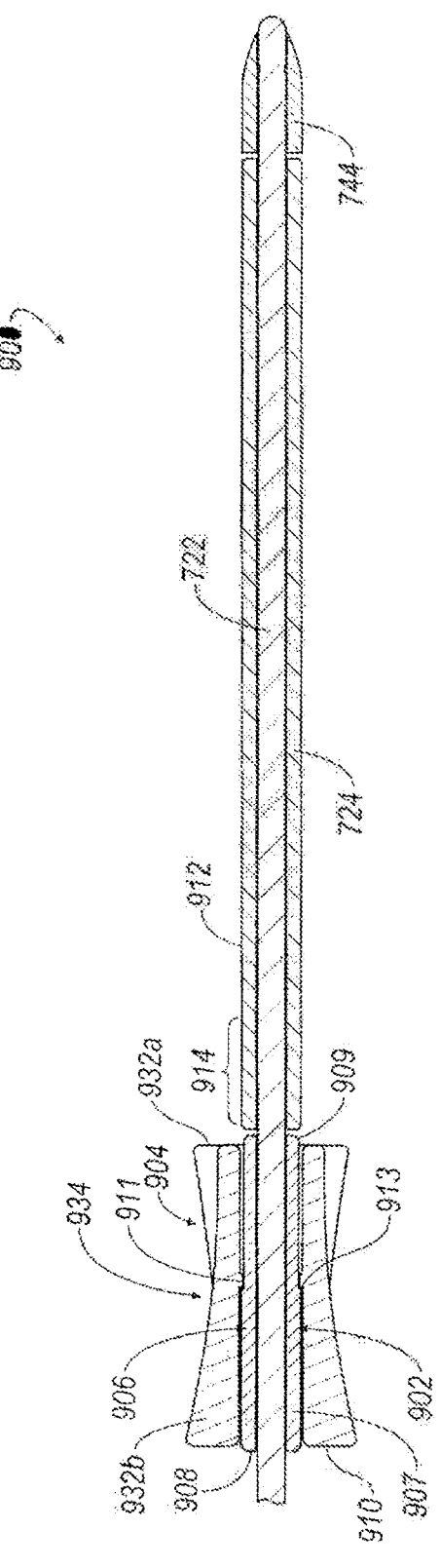
FIG. 21A is a cross-sectional view of the rotational brake of FIG. 20 and a portion of the holding arrangement in an unlocked position.

Rotation brake 900 comprises on one end a shaped stopper ferrule 902 and a stopper/ferrule 744 on the other end. Shaped ferrule 902 is affixed to the body section 722 of the holding arrangement 720, distal of the engagement barrel 724. A slider element 904 is disposed over the shaped ferrule 902. As best may be seen in FIG. 20, slider element 904 includes a channel 906 extending therethrough. In one exemplary arrangement, the channel 906 is shaped to be complementary to the shaped ferrule 902. In this matter, the slider element 904 is keyed to move across the shaped ferrule 902, as well as being positively engaged to the shaped ferrule 902. In one exemplary arrangement, the shaped ferrule 902 has a hex shape, with the channel 906 of the slider element 904 also having a hex shape. In one exemplary arrangement, the shaped ferrule 902 includes a distal section 907 and a proximal section 909. The outside diameter (OD) of the distal section 907 is slightly larger than the outside diameter OD' of the proximal section 909. The channel 906 has an inside diameter that is generally the size of the outside diameter (OD) of the distal section 907 such that the distal section 907 of the shaped ferrule 902 may be received within the channel 906. However, to prevent the slider element 904 from extending past a distal edge 908 of the shaped ferrule 902, the channel 906 may further include one or more stoppers 911. The stopper(s) 911 are configured to contact a lip 913 on the shaped ferrule 902, where the distal section 907 and proximal section 909 meet. In one exemplary arrangement, the stopper 911 is in the form of an annular ring, as best seen in FIG. 21A, although other configurations are contemplated. The stopper 911 serves as a positive stop to prevent the distal end 910 of the slider element 904 from sliding past the distal edge 908 of the shaped ferrule 902.

Figure 21B:
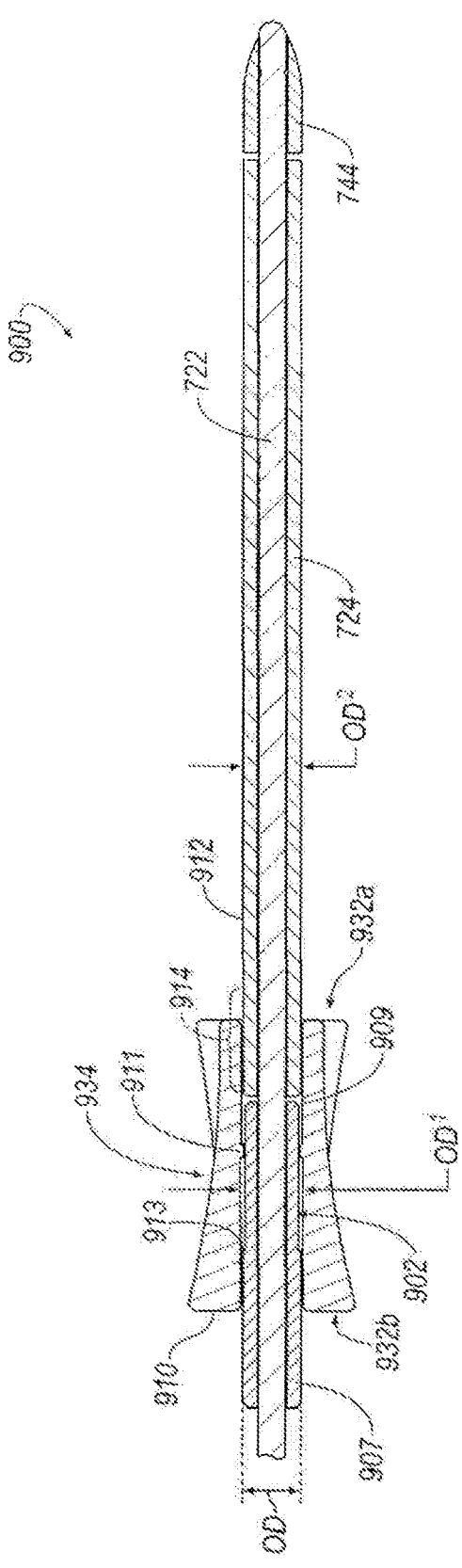
FIG. 21B is a cross-sectional view of the rotational brake of FIG. 20 and a portion of the holding arrangement in a locked position.

The engagement barrel 724 is defied by an outside diameter (OD²). The OD² generally corresponds to the outside diameter of the distal section 907 of the shaped ferrule 902 such that the slider element 904 may slide over a portion of the engagement barrel 724. In one exemplary arrangement, at least a portion of an outside surface 912 of the engagement barrel 724 defines a textured section 914 (best seen in FIG. 20). In one exemplary arrangement, textured section 914 is created by knurling, although other means for providing the textured section 914 is contemplated. As seen in FIG. 21B, the slider element 904 is configured to slide over the textures section 914 such that the channel 906, the inside diameter of the slider element 904 frictionally engages the textured section 912, while having part of the channel 906 keyed to the shaped ferrule 902. When in this position, the engagement barrel 724 is "locked" such that the engagement barrel 724 may not be rotated about the body portion 720, thereby preventing the body portion 720 from rotational movement. To facilitate easy positioning of the slider element 904, the outer surface of the slider element 904 may be textured to allow for ease of one finger manipulation. In one exemplary arrangement, the outer surface of the slider element 904 may include a series of alternating ridges 930. The slider element 904 may further have a contour whereby the proximal and distal ends 932a, 932b flare outwardly, to create a finger cradle 934 within the center for easy gripping.

Figures 22, 23A:
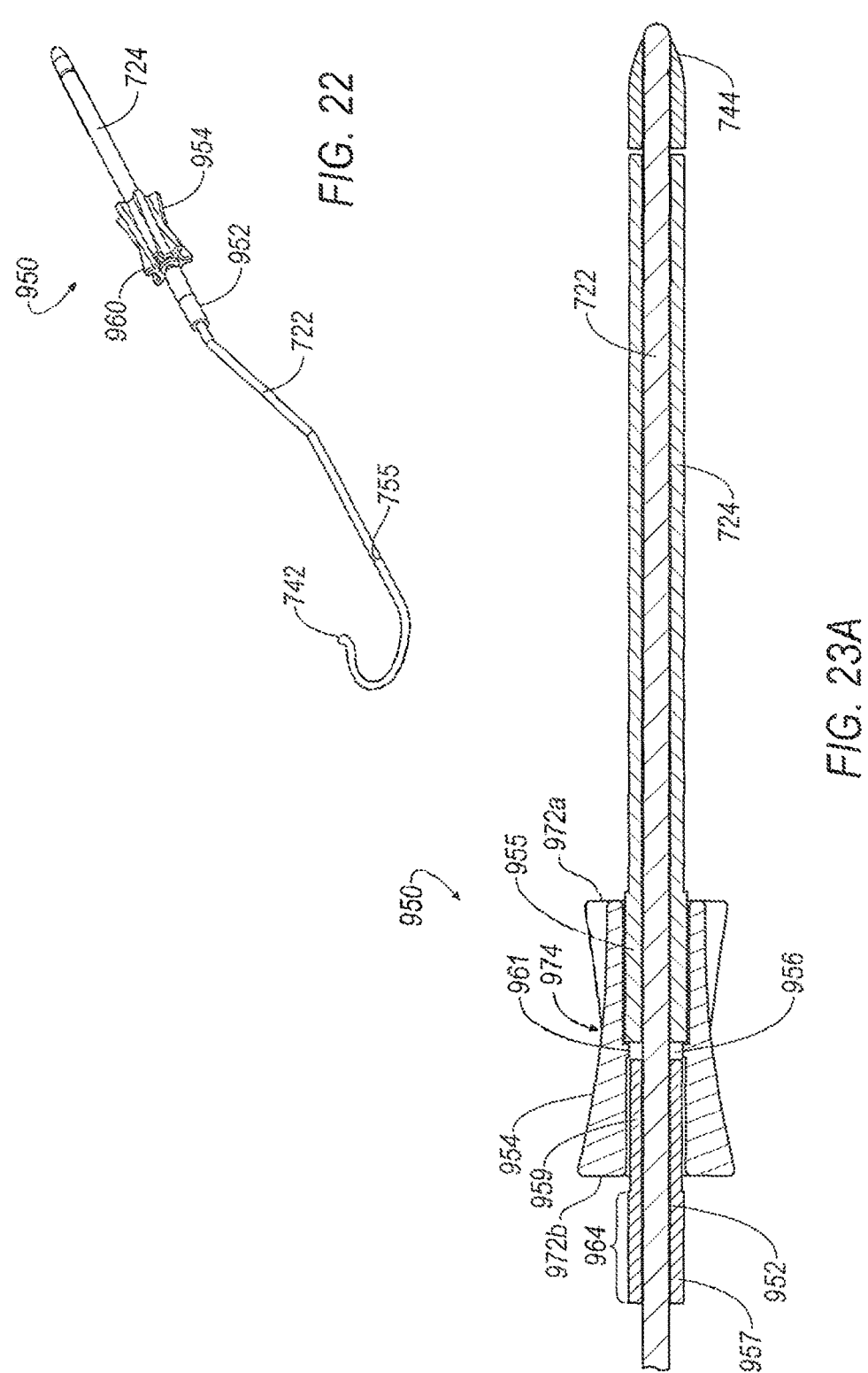
FIG. 22 is a perspective view of the holding arrangement of FIG. 16A with a further alternative rotational brake thereon.
FIG. 23A is a cross-sectional view of the rotational brake of FIG. 22 and a portion of the holding arrangement in an alternative unlocked position.
Figure 23B:
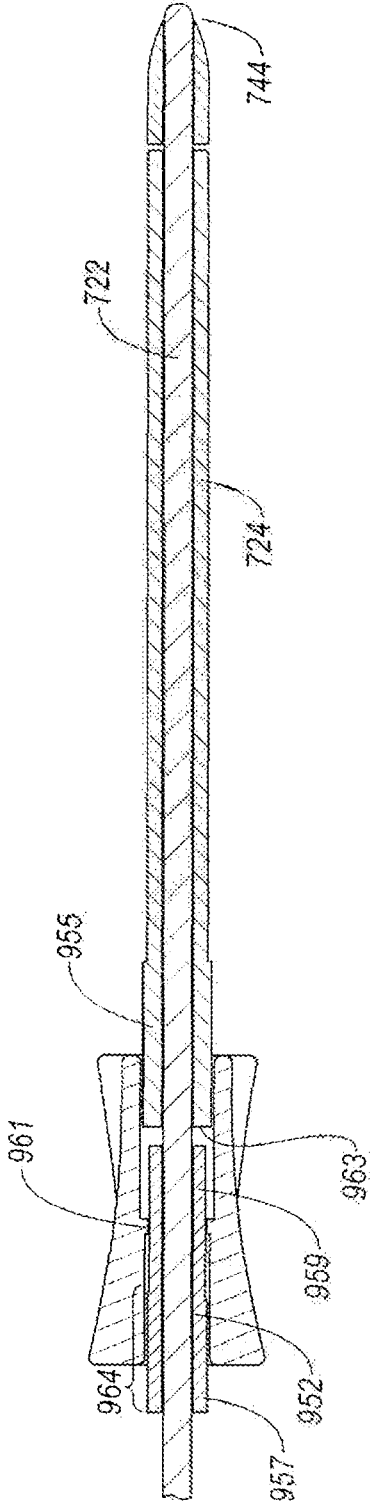
FIG. 23B is a cross-sectional view of the rotational brake of FIG. 22 and a portion of the holding arrangement in an alternative locked position.

Yet another alternative arrangement of a rotation brake 950 is shown in FIGS. 22-23. While rotation brake 950 is illustrated as being used with holding arrangement 720, it is understood that rotation brake 950 may also be used with holding arrangement 750, as well.

Rotation brake 950 is similar to rotation brake 900. More specifically, rotation brake 950 comprises an elongated ferrule 952 instead of stopper/ferrule 744. Elongated ferrule 952 is affixed to the body section 722 of the holding arrangement 720, distal of the engagement barrel 724. A slider element 954 is disposed over the elongated ferrule 952. The slider element 954 includes a channel 956 extending therethrough. In one exemplary arrangement, the channel 956 is shaped to be complementary to a shaped distal section 955 of the engagement barrel 724. In this matter, the slider element 954 is keyed to move across the shaped section 955 of the engagement barrel 724, as well as being positively engaged to the engagement barrel 724. For example, in one exemplary arrangement, the channel 956 of the slider element 954 and the shaped section 955 of the engagement barrel 724 is a splined connection.

In one exemplary arrangement, the shaped section 955 has a hex shape, with the channel 956 of the slider element 954 also having a hex shape. In one exemplary arrangement, the channel 956 has an inside diameter that is generally the size of the outside diameter OD of the shaped section 955 such that the shaped section 955 of the engagement barrel 724 may be received within the channel 956. However, to prevent the slider element 954 from extending past a proximal edge 958 of the shaped section 955, the channel 956 may further include one or more stoppers 961. The stopper(s) 961 is configured to contact a distal edge 963 of the shaped section 955. In one exemplary arrangement, the stopper 961 is in the form of an annular ring, as best seen in FIG. 22A, although other configurations are contemplated. The stopper 961 serves as a positive stop to prevent the proximal end 960 of the slider element 954 from sliding past the proximal edge 958 of the shaped section 955 of the engagement barrel 724.

The elongated ferrule 952 includes a distal section 957 and a proximal section 959. The outside surface 962 of the distal section 957 defines a textured section 964 (best seen in FIG. 22). In one exemplary arrangement, textured section 964 is created by knurling, although other means for providing the textured section 964 is contemplated. As seen in FIG. 22B, the slider element 954 is configured to slide over the textured section 964 such that the channel 956 of the slider element 954 frictionally engages the textured section 964, while having part of the channel 956 keyed to the shaped section 955 of the engagement barrel 724. When in this position, the engagement barrel 724 is "locked" with the elongated ferrule 952 such that the engagement barrel 724 may not be rotated about the body portion 720, thereby preventing the body portion 720 from being repositioned.

To facilitate easy positioning of the slider element 954, the outer surface of the slider element 954 may be textured to allow for ease of one finger manipulation. In one exemplary arrangement, the outer surface of the slider element 954 may include a series of alternating ridges 960. The slider element 954 may further have a contour whereby the proximal and distal ends 972a, 972b flare outwardly, to create a finger cradle 974 within the center for easy gripping.

Figures 24, 25:
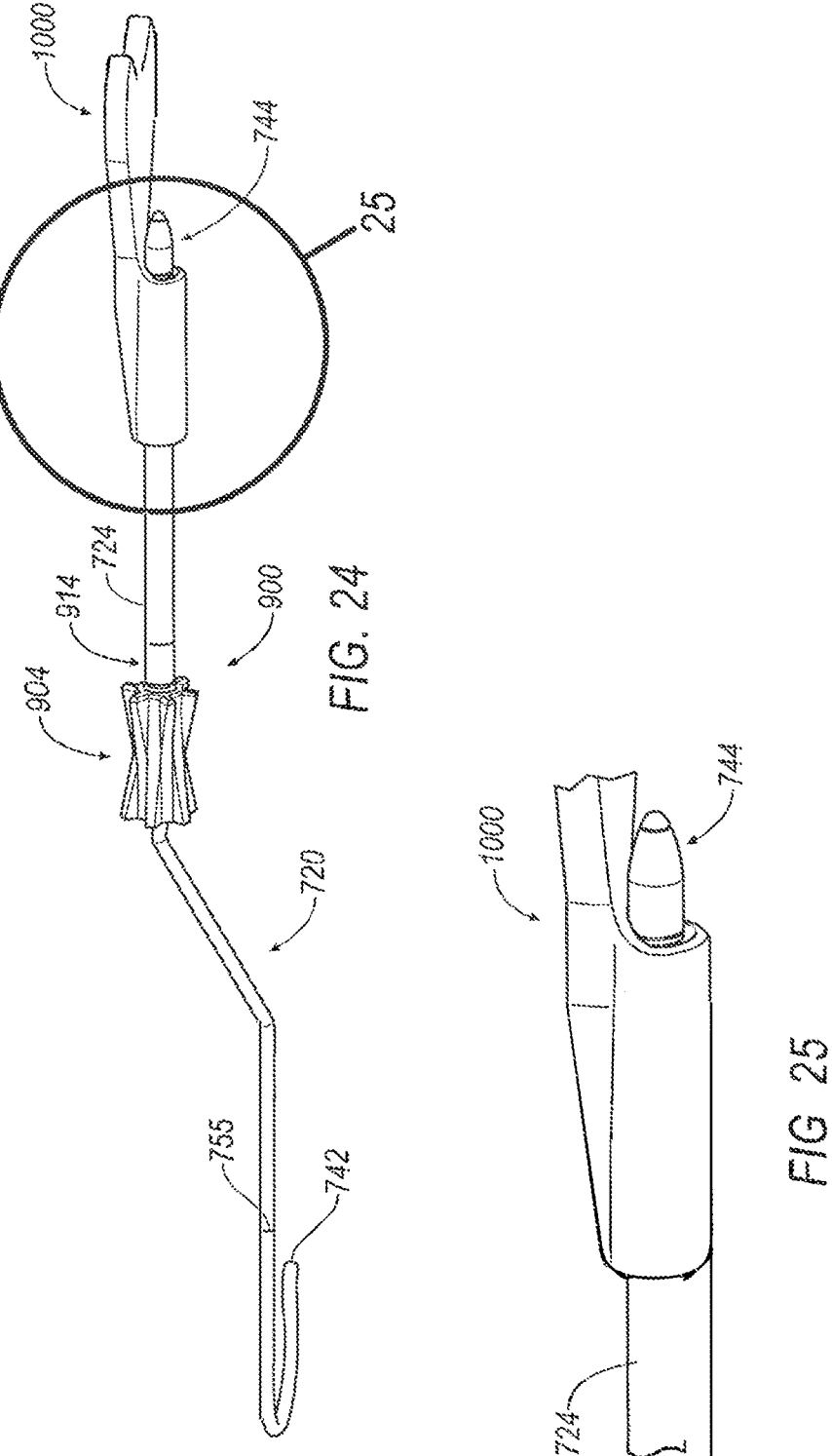
FIG. 24 is a perspective view of the rotational brake of FIGS. 20-21 with a Sugita adapter assembly.
FIG. 25 is an enlarged view of encircled area 25 of FIG. 24.
Figures 26A, 26B, 26C, 26D:
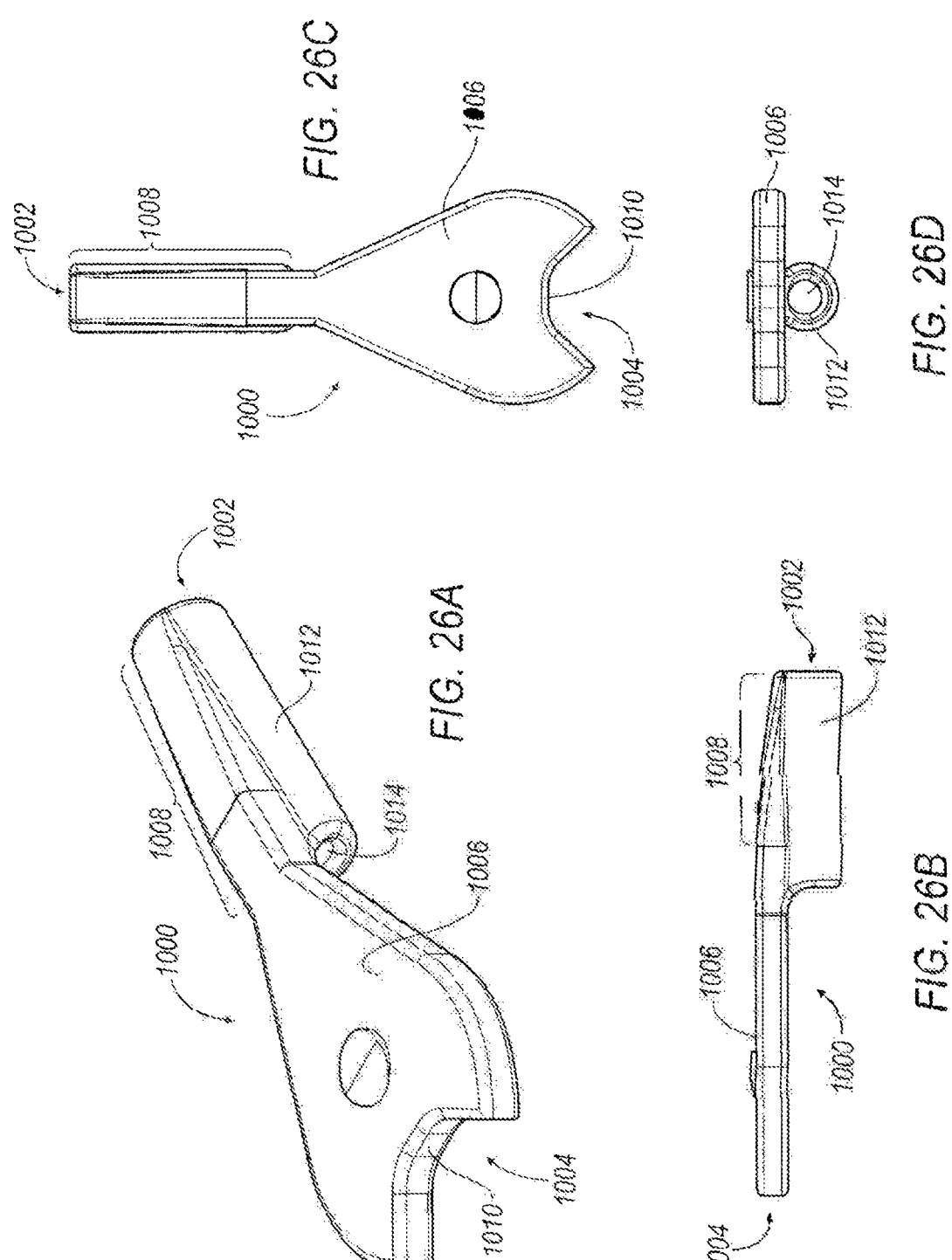
FIG. 26A is a perspective view of the Sugita adapter assembly.
FIG. 26B is a side elevational view of the Sugita adapter assembly of FIG. 26A.
FIG. 26C is a top plan view of the Sugita adapter assembly of FIG. 26A.
FIG. 26D is a front end view of the Sugita adapter assembly of FIG. 26A.

Referring to FIGS. 24-26, rotation brake 900 is shown with a Sugita adapter 1000 that is configured to attach to a Sugita Halo system. As best seen in FIGS. 26A-26D, the Sugita adapter 1000 is defined by a distal end 1002 and a proximal end 1004. A body portion 1006 and a mounting area 1008 is disposed therebetween. The mounting area 1008 extends from the distal end 1002 to the body portion 1006. The body portion 1006 flares outwardly toward the proximal end 1004. A connection groove 1010 is formed on the proximal end 1004. Connected to the mounting area 1008 is a mounting sleeve 1012. Mounting sleeve 1012 includes a mounting channel 1014 therethrough.

In operation, a proximal end of the engagement barrel 724 is inserted into the mounting sleeve 1012 of the Sugita adapter 1000 such that the Sugita adapter 1000 is fixedly connected to the engagement barrel 724. The ferrule 744 is secured to the distal end of body portion 722 to secure the Sugita adapter 1000 to the engagement barrel 724. When the slider element 904 (or slider element 954) is engaged with the engagement barrel 724, the engagement barrel 724 will be prevented from rotating about the body portion 722.

Figures 27, 28:
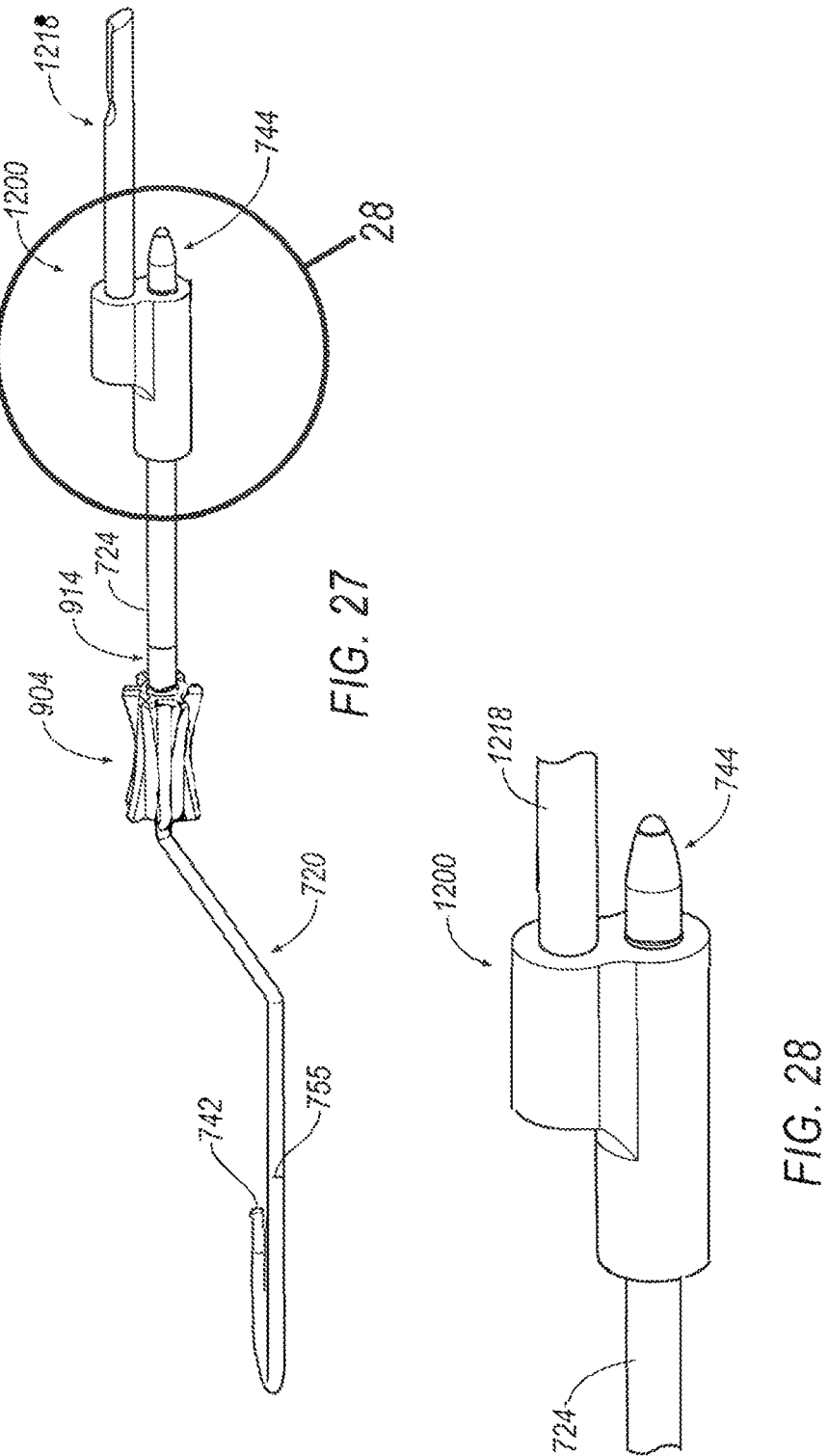
FIG. 27 is a perspective view of the rotational brake of FIGS. 20-21 with a Budde adapter assembly.
FIG. 28 is an enlarged view of encircled area 28 of FIG. 27.
Figures 29A, 29B, 29C:
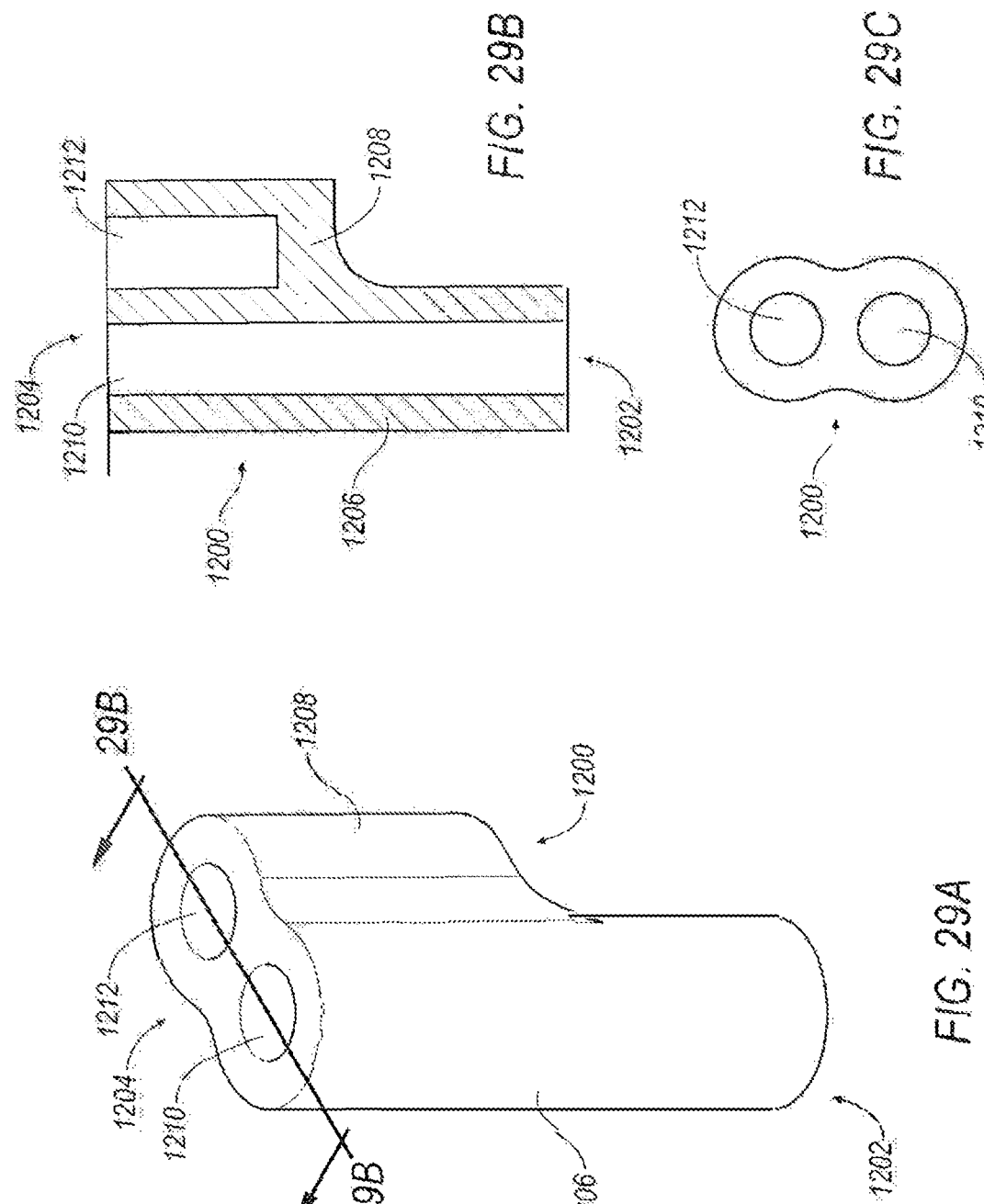
FIG. 29A is a perspective view of the Budde adapter assembly.
FIG. 29B is a cross-sectional view of the Budde adapter assembly of FIG. 29A, taken along lines 29B-29B in FIG. 29A.
FIG. 29C is a top plan view of the Budde adapter assembly of FIG. 29A.
Figures 30A, 30B, 30C, 30D:
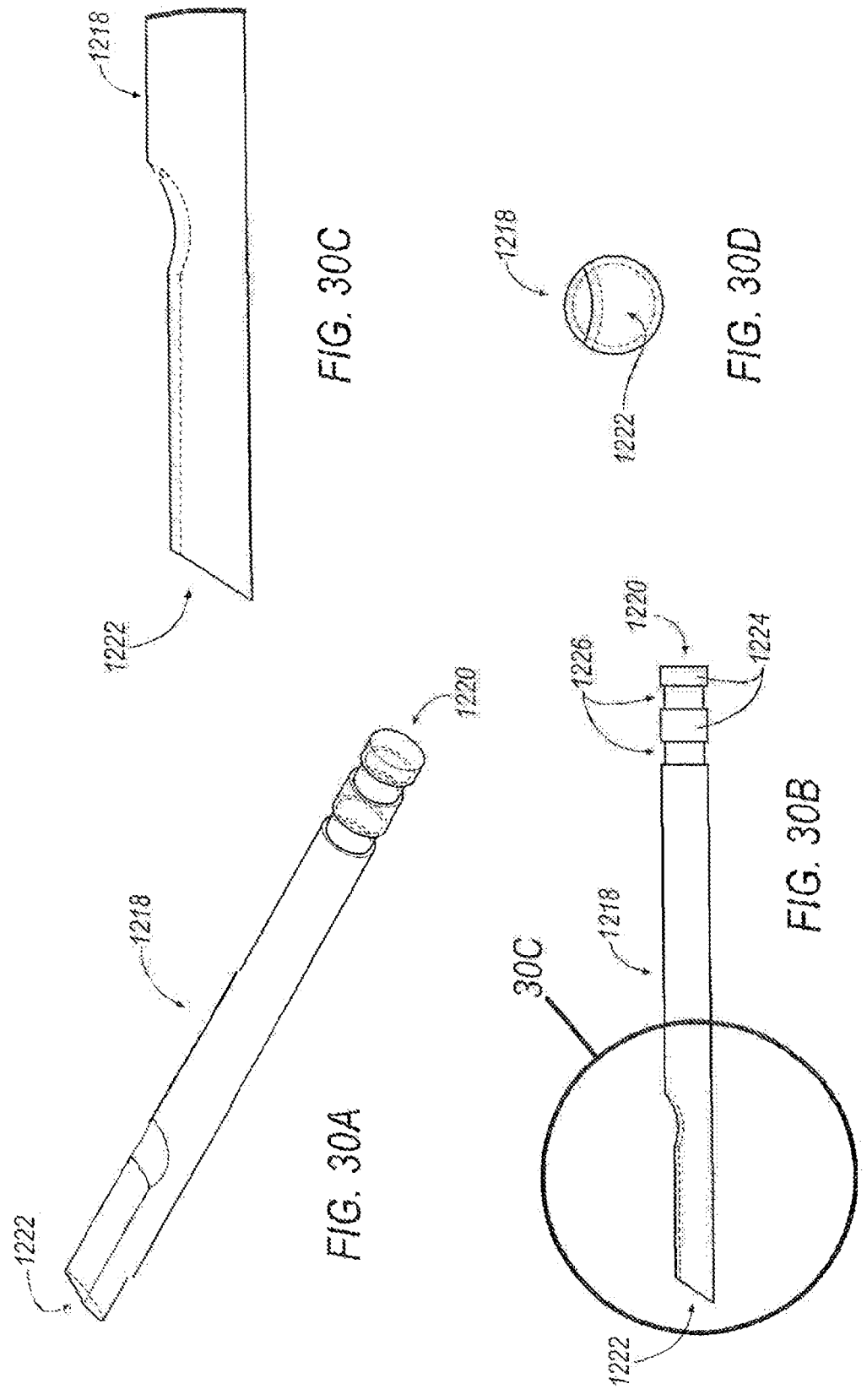
FIG. 30A is a perspective view of support shaft for connecting to the Budde adapter assembly.
FIG. 30B is a side elevational view of the support shaft of FIG. 30A.
FIG. 30C is an enlarged view of encircled area 30C of FIG. 30B.
FIG. 30D is a distal end view of the support shaft of FIG. 30A.

Referring to FIGS. 27-29, rotation brake 900 is shown with a Budde adapter 1200 that is configured to attach to a Budde Halo Retractor System. As best seen in FIGS. 29A-29C, the Budde adapter 1500 is defined by a distal end 1202 and a proximal end 1204. A body portion 1206 and a mounting area 1208 is disposed therebetween. The mounting area 1208 extends from the proximal end 1204, but tends before reaching the distal end 1202 of the body portion 1206. The body portion 1206 is formed as a mounting sleeve and includes a mounting channel 1210 therethrough. The mounting area 1208 includes a support groove 1212. Support groove 1212 does not extend through the mounting area 1208.

In operation, a proximal end of the engagement barrel 724 is inserted into the mounting channel 1210 of the Budde adapter 1000. The ferrule 744 is secured to the distal end of body portion 722 to fixedly secure the Budde adapter 1000 to the engagement barrel 724. A support shaft 1218 is provided that connects to the Budde Halo system.

The support shaft 1218 is defined by a first end 1220 and a second end 1222. The first end 1220 is configured to be received within the support groove 1212. In one exemplary arrangement, the first end 1220 is formed with at least one support ring 1224 that is separated by annular recesses 1226. When inserted within the support groove 1212, the support rings 1224 frictionally engage sidewalls of the support grove 1212 to secure the support shaft 1218 to the Budde adapter 1218. The second end 1222 further comprises a relieved section 1228 with a recess 1230 therein. The recess 1230 is adapted to be received within a section of the Budde Halo system.

An alternative rotation brake 1300 is illustrated in FIGS. 31-34. While rotation brake 1300 is illustrated as being used with holding arrangement 720, it is understood that rotation brake 1300 may also be used with holding arrangement 750, as well.

Rotation brake 1300 comprises stopper ferrules 744 that are affixed to the body section 722 of the holding arrangement 720, on either side of the engagement barrel 724. A collar element 1302 is disposed over and fixed to the ferrule 744 that is distal of the engagement barrel 724. An insert member 1304 is slidably disposed over the engagement barrel 724 and is configured to be moved freely over the engagement barrel 724, as will be explained in further detail below.

Figure 33:
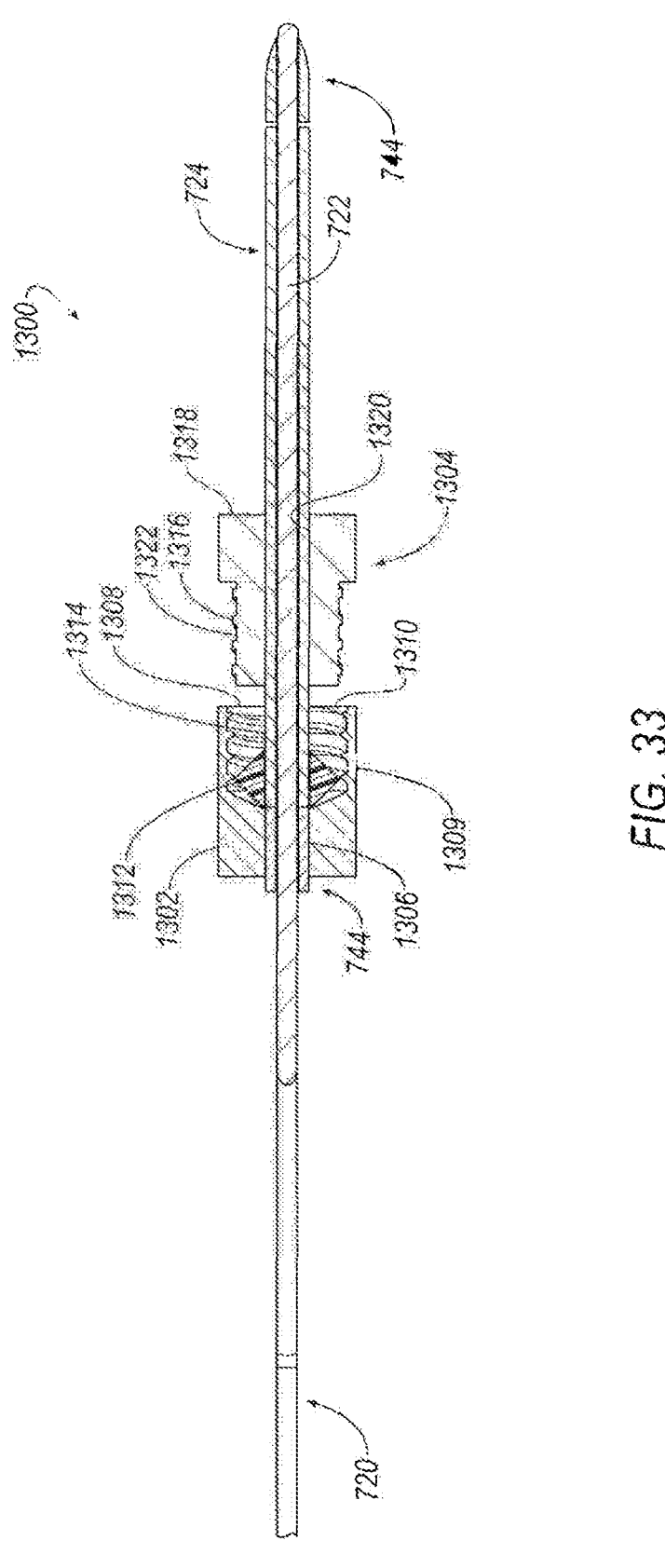
FIG. 33 is a cross-sectional view of the rotational brake of FIG. 31 in an unlocked position.

Referring to FIG. 33, the collar element 1302 further comprises a fixing portion 1306, a channel portion 1308 and a proximal opening 1310. The fixing portion 1306 is fixedly connected to the distally positioned (with respect to the engagement barrel 724) ferrule 744. The channel portion 1308 includes a connection arrangement. A distal end face 1309 of the channel portion 1308 defines an end of the channel portion 1308. In one exemplary arrangement, the distal end face 1309 is converges toward the ferrule 744 such that the distal end face 1309 is angled inwardly toward a center axis extending through the channel portion 1308. Also disposed within the channel portion 1308 is a selectively compressible insert 1312. In one exemplary arrangement, the selectively compressible insert is constructed of silicon. The selectively compressible insert 1312 further includes a channel 1314 therein. The channel 1314 is sized to receive the engagement barrel 724 therein. In one exemplary arrangement, the selectively compressible insert 1312 is configured as a double conical piece, arranged such that the tips of the conical sections converge to a point above the selectively compressible insert 1312. When in the unlocked position, as is demonstrated in FIGS. 31 and 33, the selectively compressible insert 1312 is fixed to the engagement barrel 724. The engagement barrel 724 is free to rotate about the body portion 722 in this position.

The insert member 1304 is defined by an engagement section 1316 and a grip portion 1318. A mounting channel 1320 extends through both the engagement section 1316 and the grip portion 1318. In one arrangement the mounting channel 1320 is sized to be slightly larger than the outer diameter of the engagement barrel 727 such that the insert member 1304 is freely moveable over the engagement barrel 727. The outer surface 1322 of the engagement section 1316 includes a connection arrangement that is complementary to the connection arrangement of the channel portion 1308 of the collar element 1302. In one exemplary arrangement, the connection arrangements are threaded arrangements. However, it is understood that other connection arrangements are also contemplated, such as a keyed connection.

Figure 31:
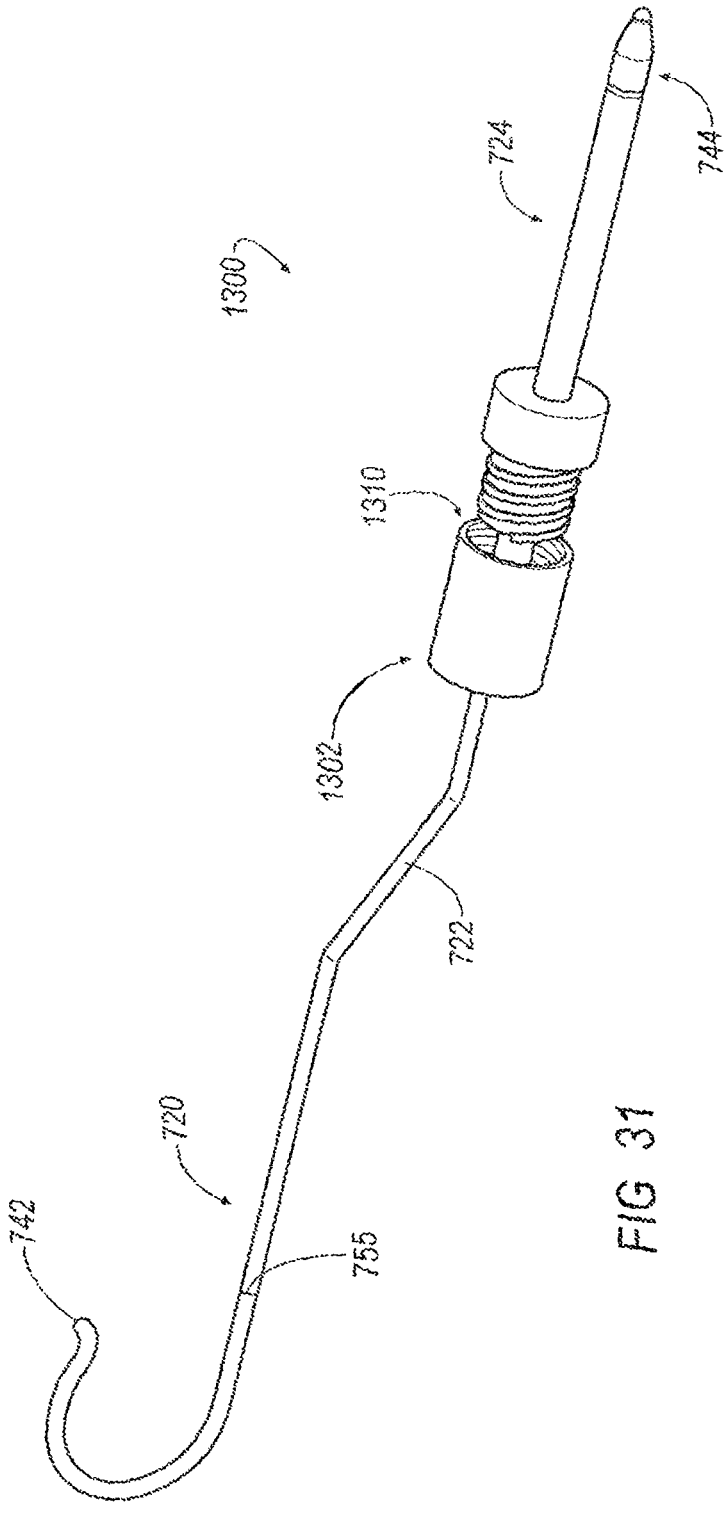
FIG. 31 is a perspective view of the holding arrangement of FIG. 16A with a further alternative rotational brake thereon in an unlocked position.

To move the rotational brake 1300 from the unlocked position (as shown in FIGS. 31 and 33) to the locked position (FIG. 32), the insert member 1304 is slid over the engagement barrel in the distal direction, represented by arrow D in FIG. 33. In this manner, the engagement section 1316 is received within the opening 1310 and disposed within the channel portion 1308, with the respective connection arrangements of the insert member 1304 and the collar element 1302 engaged with one another. Because the selectively compressible insert 1312 is disposed within the channel portion 1308, as the engagement section 1316 moves toward the end of the channel portion 1308, the selectively compressible insert 1312 is compressed against the distal end face 1309 of the channel portion 1308. In this manner, the selectively compressible insert 1312 frictionally grips the engagement barrel 724. The angled arrangement of the distal end face 1309 assists in this gripping engagement. Because the connection arrangements of the insert member 1304 and collar element 1302 frictionally engage with one another, the insert member 1304 effectively locks the selectively compressible insert 1312 to the engagement barrel 727, thereby preventing the engagement barrel 727 from rotating with respect to the body portion 722. To unlock the rotational brake 1300, the grip portion 1318 is grasped and disengaged from the collar member 1302. In one exemplary arrangement, as the connection arrangements in the channel 1308 and the outer surface 1322 of the engagement section 1316 are threaded arrangements, disengaging the insert member 1304 from the collar member 1302 involves rotating the insert member 1304. Once the connection arrangements are disengaged, the insert member is pulled in the proximal direction (i.e., opposite direction as direction D) such that the insert member 1304 slides over the engagement barrel 727, away from the fixed collar member 1302.

Figure 32:
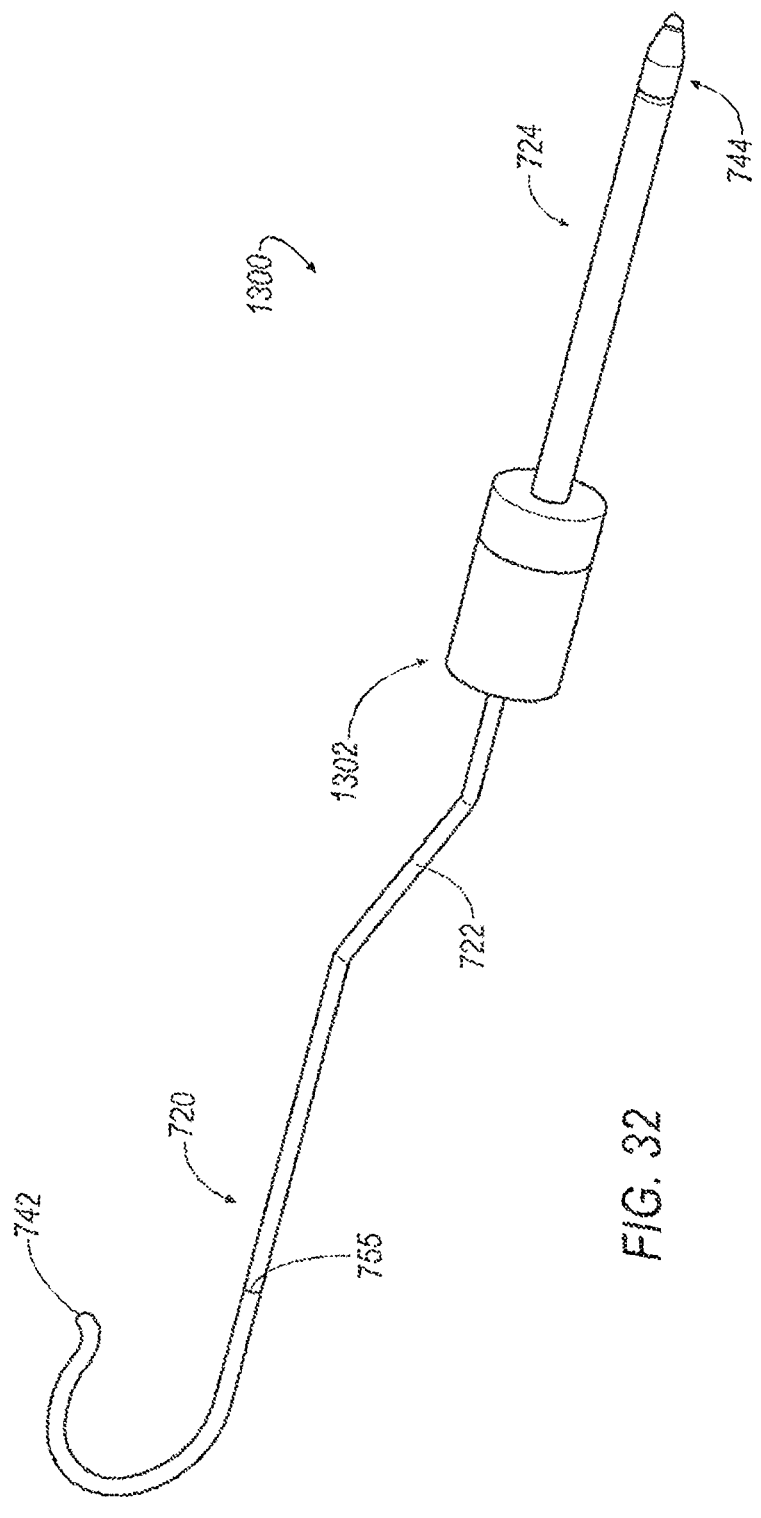
FIG. 32 is a perspective view of the rotational brake of FIG. 31 in a locked position.
Figure 34A:
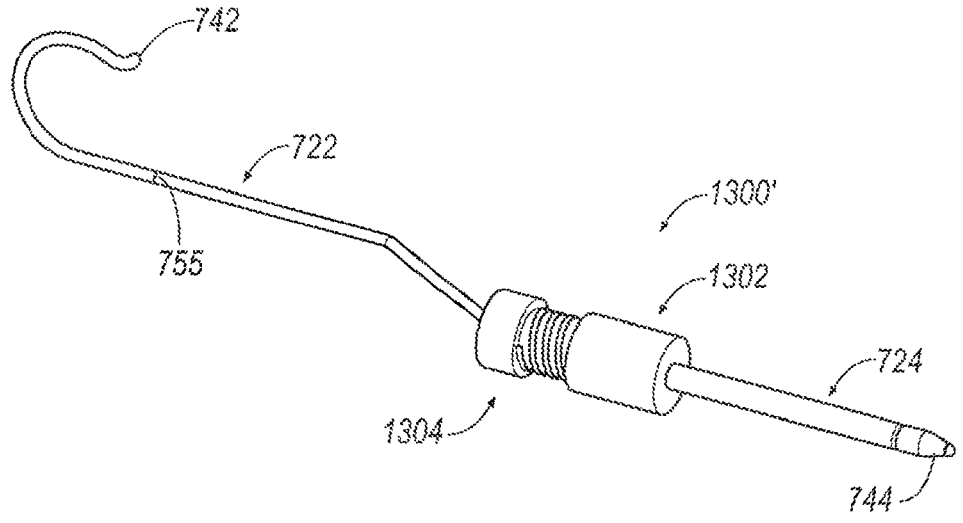
FIG. 34A is a perspective view of an alternative arrangement of the rotational brake of FIG. 31 in an unlocked position.
Figure 34B:
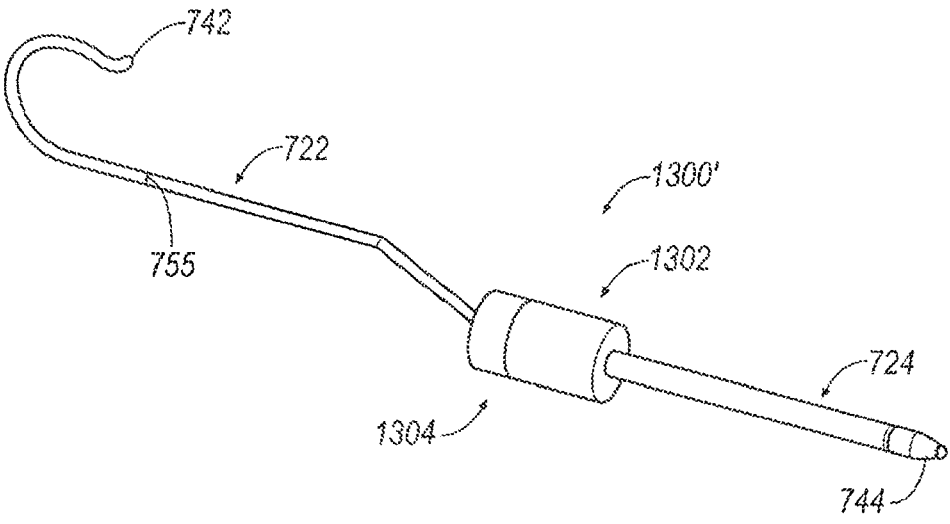
FIG. 34B is a perspective view of the rotational brake of FIG. 32 in a locked position.

While the embodiment shown in FIGS. 31-33 illustrate that the collar member 1302 is fixed to the distal ferrule 744 and the insert member 1304 is moveable over the engagement barrel 727, in another exemplary arrangement, illustrated in FIGS. 34A-34B, this arrangement is reversed. More specifically, the insert member 1304 is fixedly connected to the body section 722, distal of the distal ferrule 744. The collar member 1302 is slidingly engaged over the engagement barrel 727, as is the selectively compressible insert 1312. As the collar member 1302 is moved in the distal direction to engage with the insert member 1304, the selectively compressible insert 1312 moves with the collar member 1302. Due to its placement distal to, but adjacent, the distal ferrule 744, the engagement section 1316 will compress the selectively compressible insert 1312 such that it will engage around the distal ferrule 744. With this action, the engagement barrel 727 will be prevented from rotating with respect to the body portion 722.

Once a cytoreductive resection of area of interest 500 has been completed, the process then proceeds to step 436. In step 436 a decision is made to either remove outer sheath 102 or to leave outer sheath 102 in position. More specifically, for some therapy applications, removal of outer sheath 102 may be more effective than leaving outer sheath in place to deliver the therapy. If the decision is made to remove outer sheath 102, after removal of outer sheath 102, the process 400 proceeds to step 438.

As one of ordinary skill in the art may appreciate, the natural elasticity of brain tissue will maintain access or a corridor to area of interest 500 for period of time. In step 438, while the corridor is still intact after removal of outer sheath 102, in one exemplary arrangement, a delivery device may be inserted into the corridor to deliver irrigation to the surgical site. In some instances, a syringe may be inserted into the corridor to deliver an irrigating fluid, such as saline directly to the surgical site. In another exemplary configuration, a drainage catheter (which is configured with a plurality of small openings at its distal end) is delivered into the corridor such that the distal end of the catheter is placed at or adjacent the surgical site. Irrigating fluid is then introduced into the proximal end (such, as for example, by operatively attaching a syringe barrel to the proximal end), to deliver the irrigating fluid to the surgical site. The irrigating fluid flushes out debris and assists in the brain tissue's natural tendency to close back in on itself. Once the surgical site has been irrigated, it may also be desirable to deliver certain therapies directly to the surgical site, thereby avoiding therapy delivery and uptake issues traditionally encountered by systemic approaches. For example, certain therapies that may be provided in liquid form may be directly injected through the corridor, just prior to the tissue closing back in on itself. Because the corridor is closing, the therapy will be held in place at the surgical site, thereby increasing its effectiveness at the site and surrounding tissue.

In step 442, area of interest/surgical site 500 is irrigated to again remove any debris from the area. Irrigation may be performed in the same manner as discussed in step 438, except through outer sheath 102. Once irrigation is complete, the process proceeds to step 444.

In step 444 a therapy is delivered to area of interest 500. In one exemplary configuration, intraoperative radiotherapy (IORT) may be employed, so as to deliver therapy directly to area of interest 500 through outer sheath 102. In one exemplary configuration, an implantable therapy may be applied to area of interest 500. Example of an implantable therapy include: bioabsorbable radiation pellets, wafers or mesh, such as, for example, those manufactured by Nano-Rad LLC. Other examples include, but are not limited to, titanium capsules or seeds with radiation contents, bioabsorbable gels or foams that contain radioactive, chemotherapy or immunotherapy agents.

In another exemplary configuration, a balloon catheter may be used to perform brachytherapy following the removal of diseased tissue at area of interest 500. For example, a balloon catheter may be inserted through outer sheath 102 and delivered to area of interest, and then the balloon catheter may be inserted with a predetermined amount of radioactive solution followed by the delivery of radiation to the surrounding tissues. A commercially available catheter that may be used includes the GliaSite balloon catheter, with an Iotrex radioactive solution. Use of a balloon catheter may provide a more targeted delivery of liquid radiation, thereby reducing impact on brain tissues surrounding the diseased tissue.

In another exemplary arrangement, an electron beam driven X-ray source may be provided. One such exemplary configuration is the Zeiss INTRABEAM®. The electrons are generated and accelerated in a main unit and travel via an electron beam drift tube which is surrounded by a conical applicator sheath such that its tip lies at an epicenter of an applicator sphere to provide a point source of low energy X-rays at the tip. With this configuration, a nearly isotropic field of low energy is emitted.

In operation, the applicator sheath is inserted through outer sheath 102 and into the surgical cavity at area of interest 500. An intraoperative ultrasound may be performed to determine the distance of the applicator surface to the skin, to avoid significant skin doses. The applicator sheath may be secured into place by the surgeon using subcutaneous sutures around the neck of the sphere, similar to that described above in connection with outer sheath 102.

In another exemplary arrangement, a photodynamic therapy may be used, whereby a predetermined chemical composition may provided to the patient and the chemical composition may be selectively activated by a predetermine wavelength, thereby achieving a therapeutic reaction. For example, in one exemplary configuration, illuminating ring 300 may be turned on to achieve the therapeutic reaction. In another exemplary configuration, a light source, such as, for example, a fiber optic bundle, may be directed through outer sheath 102, either directly through outer sheath 102 or through delivery sleeve 800.

In yet another exemplary configuration, external beam high frequency ultrasound or interstitial high frequency ultrasound may also be delivered through outer sheath and directly to area of interest 500. Other applicable methodologies of delivering therapy are also contemplated.

After surgery and therapy on the target tissue is complete, the process proceeds to step 446. In this step, the instruments used for surgery and/or therapy are removed from outer sheath 102. As the target tissue is removed, brain tissue will naturally fill the void formed by removing area of interest 500 so that healthy brain tissue underlying the now removed target tissue is adjacent the end of outer sheath 102. Outer sheath 102 is then gently removed and the brain tissue will naturally fill and reclaim the space formerly occupied by the abnormality and outer cannula 102, aided by the irrigation of area of interest 500. Moreover, as the brain tissue reclaims the space formerly occupied by the abnormality and outer cannula 102, implanted therapies, such as, for example, bioabsorbable radiation pellets, wafers or mesh, will be held in place at area of interest 500 to provide effective treatment, all delivered and unencumbered by the limitations normally encountered attempting to cross the blood brain barrier. While this process may take several minutes, it is relatively atraumatic. Once outer sheath 102 has been removed, the process continues to step 448, whereby the dura, skull and scalp are then closed in a known manner and the process ends. In the exemplary cases whereby a treatment device may be implanted, full reclaiming of the space is delayed due to the implant until implant is explanted or absorbed.

Because the location of the area of interest will vary from patient to patient, in one exemplary arrangement, it is contemplated that surgical access system 100 will be provided as part of a kit. More specifically, it is contemplated that a set of multiple obturators 104 may be provided that have different lengths and/or diameters. The set may be provided in a container that is configured be sterilized, with obturators 104 secured therein. It is also contemplated that a set of manipulation tools 700/700' may also be provided with the kit, and that manipulation tools 700/700' may be positioned within the container for selective sterilization. Outer sheath 102 may be provided with the kit, in various lengths and diameters that correspond to the lengths and diameters of obturators 104 provided in the kit. However, in one exemplary arrangement, outer sheaths 104 are provided separately as single use devices, in sterilized pouches.

While the above-described system provides the advantage of creating direct access to an area of interest, including an area of interest in the subcortical space, thereby permitting debulking of the area of interest to reduce the biological load of the abnormal tissue, as well as delivery of therapy in-situ (without the encumbrance and limitations encountered with systemic therapy delivery), for certain diseases, additional subsequent therapy may be warranted for increased therapeutic benefits.

More specifically, to be able to define an effective subsequent treatment therapy cocktail that will be effective on newly evolved strain of cells and tissue or disease that "morphs", the abnormal tissue at the area of interest requires imaging to define the area of interest, needs to be accessed, requires interrogation (sampling with or without a cytoreductive debulking of the area) to determine an appropriate therapeutic cocktail for the newly evolved cells and tissue. This process may be required to be repeated at a specific time or at a variety of time intervals for the live of the patient to assure the appropriate management or cure of the disease.

In the case of functional diseases of the brain such as a Alzheimer's, Parkinson's, epilepsy, bi-polar, depression, etc., the cells and affected tissues may not change or morph after the initial treatment but it may be useful to subsequently, image, access, interrogate the tissue (sample or debulk) the same or another area of interest after the initial delivery of a therapy to determine the effectiveness of the previous application to determine the response of the tissues to the treatment regimen to determine the need for subsequent treatment regimens and the nature of the therapeutic treatment required for the subsequent therapy.

It will be appreciated that the surgical access system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A selectively lockable holding assembly for a surgical access assembly, comprising: a body portion;
  an engagement barrel;
  a retaining member at a distal end of the body portion;
  wherein the engagement barrel is positioned on the body portion and configured to be selectively rotated about the body portion; and
  a rotation brake mounted on the engagement barrel, wherein the rotation brake is selectively operable to lock the engagement barrel against rotation with respect to the body
  portion, wherein the rotation brake comprises a leg, and a selectively turnable brake lever having a main body section and opposing finger tabs extending outwardly therefrom, wherein sloped members are disposed on a top surface of the main body section, a groove is disposed between the sloped members, and the opposing finger tabs are rotatable to cause the sloped members to engage against the leg.

2. The holding assembly of claim 1, further comprising a Sugita adapter mounted to the engagement barrel.

3. The holding assembly of claim 2, wherein the Sugita adapter further comprises a body portion and a mounting area, wherein the mounting area further comprises a mounting sleeve.

4. The holding assembly of claim 3, wherein the mounting sleeve further comprises a mounting channel therethrough that receives the engagement barrel.

5. The holding assembly of claim 1, further comprising a Budde adapter mounted to the engagement barrel.

6. The holding assembly of claim 5, wherein the Budde adapter includes a body portion formed as a mounting sleeve and including a mounting channel therethrough that receives the engagement barrel.

7. The holding assembly of claim 6, further comprising a mounting area that includes a support groove, wherein the support groove does not extend through the mounting area and receives a support shaft therein.

8. The holding assembly of claim 7, wherein the support shaft is defined by a first end and second end and wherein the first end is formed with at least one support ring and an annular recess, wherein the support ring frictionally engages sidewalls of the support groove to secure the support shaft to the Budde adapter.

9. The holding assembly of claim 1, wherein the retaining member further includes a treated section that is configured to reduce glare.

10. A selectively lockable holding assembly for a surgical access assembly, comprising:
   a body portion;

an engagement barrel;
a retaining member at a distal end of the body portion;
wherein the engagement barrel is positioned on the body portion and configured to be selectively rotated about the body portion; and
a rotation brake mounted on the engagement barrel and receiving the body portion, wherein the rotation brake is selectively operable to frictionally grip the body portion to lock the engagement barrel against rotation with respect to the body portion, wherein the rotation brake comprises a leg, and a selectively turnable brake lever having a main body section and opposing finger tabs extending outwardly therefrom, wherein sloped members are disposed on a top surface of the main body section, a groove is disposed between the sloped members, and the opposing finger tabs are rotatable to cause the sloped members to engage against the leg.

11. The holding assembly of claim 10, further comprising a Sugita adapter mounted to the engagement barrel.

12. The holding assembly of claim 11, wherein the Sugita adapter further comprises a body portion and a mounting area, wherein the mounting area further comprises a mounting sleeve.

13. The holding assembly of claim 12, wherein the mounting sleeve further comprises a mounting channel therethrough that receives the engagement barrel.

14. The holding assembly of claim 10, further comprising a Budde adapter mounted to the engagement barrel.

15. The holding assembly of claim 14, wherein the Budde adapter includes a body portion formed as a mounting sleeve and including a mounting channel therethrough that receives the engagement barrel.

16. The holding assembly of claim 15, further comprising a mounting area that includes a support groove, wherein the support groove does not extend through the mounting area and receives a support shaft therein.

* * * * *